US012083179B2

(12) United States Patent
Clayton et al.

(10) Patent No.: US 12,083,179 B2
(45) Date of Patent: *Sep. 10, 2024

(54) COLON CLEANSING COMPOSITIONS AND METHOD OF USE

(71) Applicant: NORGINE BV, Amsterdam (NL)

(72) Inventors: Lucy Clayton, Uxbridge (GB); Alasdair Cockett, Uxbridge (GB); Mark Christodoulou, Uxbridge (GB); Ian Davidson, Uxbridge (GB); Lynn Farrag, Uxbridge (GB); Marc Halphen, London (GB); Leighton Jones, Uxbridge (GB); Vanik Petrossian, Woburn, MA (US); Peter Stein, Amsterdam Zuid-Oost (NL); David Tisi, Woburn, MA (US); Alex Ungar, Wigton (GB); Jeffrey Worthington, Woburn, MA (US)

(73) Assignee: NORGINE BV, Amsterdam (NL)

( * ) Notice: Subject to any disclaimer, the term of this patent is extended or adjusted under 35 U.S.C. 154(b) by 108 days.

This patent is subject to a terminal disclaimer.

(21) Appl. No.: 17/384,227

(22) Filed: Jul. 23, 2021

(65) Prior Publication Data

US 2021/0346503 A1 Nov. 11, 2021

Related U.S. Application Data

(63) Continuation of application No. 16/028,819, filed on Jul. 6, 2018, which is a continuation of application No. 15/454,132, filed on Mar. 9, 2017, now Pat. No. 10,016,504, which is a continuation of application No. 15/141,054, filed on Apr. 28, 2016, now Pat. No. 9,707,297, which is a continuation of application No. 14/657,495, filed on Mar. 13, 2015, now Pat. No. 9,326,969, which is a continuation of application No. 14/223,127, filed on Mar. 24, 2014, now Pat. No. 8,999,313, which is a continuation of application No. PCT/EP2013/068738, filed on Sep. 10, 2013.

(60) Provisional application No. 61/787,366, filed on Mar. 15, 2013, provisional application No. 61/699,488, filed on Sep. 11, 2012.

(51) Int. Cl.

| | | |
|---|---|---|
| A61K 47/26 | (2006.01) |
| A61K 9/00 | (2006.01) |
| A61K 9/08 | (2006.01) |
| A61K 31/047 | (2006.01) |
| A61K 31/375 | (2006.01) |
| A61K 31/765 | (2006.01) |
| A61K 31/77 | (2006.01) |
| A61K 33/04 | (2006.01) |
| A61K 33/14 | (2006.01) |
| A61K 47/02 | (2006.01) |
| A61K 47/10 | (2017.01) |
| A61K 47/12 | (2006.01) |

(52) U.S. Cl.
CPC ............ *A61K 47/26* (2013.01); *A61K 9/0053* (2013.01); *A61K 9/0095* (2013.01); *A61K 9/08* (2013.01); *A61K 31/047* (2013.01); *A61K 31/375* (2013.01); *A61K 31/765* (2013.01); *A61K 31/77* (2013.01); *A61K 33/04* (2013.01); *A61K 33/14* (2013.01); *A61K 47/02* (2013.01); *A61K 47/10* (2013.01); *A61K 47/12* (2013.01)

(58) Field of Classification Search
CPC .................................. A61P 1/10; A61K 47/26
See application file for complete search history.

(56) References Cited

U.S. PATENT DOCUMENTS

| | | |
|---|---|---|
| 2,187,467 A | 1/1940 | Stuart |
| 2,427,692 A | 9/1947 | Ruskin |
| 2,481,353 A | 9/1949 | Schnabel |
| 2,694,719 A | 11/1954 | Opplt |
| 3,211,614 A | 10/1965 | Embring et al. |
| 5,274,001 A | 12/1993 | Borody |
| 5,281,606 A | 1/1994 | Guzzi et al. |
| 5,411,745 A | 5/1995 | Oshlack et al. |
| 5,540,945 A | 7/1996 | Ikushima et al. |
| 5,858,403 A | 1/1999 | Borody et al. |
| 6,121,250 A | 9/2000 | Nishiyama et al. |
| 6,162,464 A | 12/2000 | Jacob et al. |
| 6,444,198 B1 | 9/2002 | Daggy et al. |

(Continued)

FOREIGN PATENT DOCUMENTS

| | | |
|---|---|---|
| AU | 2011101324 A4 | 11/2011 |
| CN | 1150021 A | 5/1997 |

(Continued)

OTHER PUBLICATIONS

Notice of Reasons for Rejection issued in Application No. JP 2020-015456, mailed Dec. 8, 2021.

(Continued)

*Primary Examiner* — Gina C Justice
(74) *Attorney, Agent, or Firm* — BakerHostetler; Toni-Junell Herbert

(57) ABSTRACT

The invention provides a colon cleansing solution comprising:

a) 300 to 800 mmol per litre ascorbate anion provided by a mixture of:

(i) ascorbic acid and (ii) one or more salts of ascorbic acid the components (i) and (ii) being present in a molar ratio of from 1:4.5 to 1:7.0; and b) 10 to 200 g per litre polyethylene glycol.

The invention also provides methods and kits associated with, or making use of the solutions, and compositions for the preparation of the solutions.

20 Claims, 2 Drawing Sheets

(56) References Cited

U.S. PATENT DOCUMENTS

| | | | |
|---|---|---|---|
| 6,592,901 B2 | 7/2003 | Durig et al. | |
| 6,946,149 B2 | 9/2005 | Cleveland | |
| 7,658,914 B2 | 2/2010 | Barras et al. | |
| 8,999,313 B2* | 4/2015 | Clayton | A61K 31/375 514/474 |
| 9,326,969 B2* | 5/2016 | Clayton | A61K 31/765 |
| 9,707,297 B2* | 7/2017 | Clayton | A61K 31/77 |
| 10,016,504 B2* | 7/2018 | Clayton | A61K 47/12 |
| 2004/0171691 A1 | 9/2004 | Tang et al. | |
| 2005/0079216 A1 | 4/2005 | Petereit et al. | |
| 2005/0129781 A1 | 6/2005 | Skiendzielewski et al. | |
| 2005/0152989 A1 | 7/2005 | Pelham et al. | |
| 2005/0226906 A1 | 10/2005 | Moneymaker et al. | |
| 2006/0029570 A1 | 2/2006 | Aronson et al. | |
| 2007/0298100 A1 | 12/2007 | Barras et al. | |
| 2008/0193523 A1 | 8/2008 | Heim et al. | |
| 2008/0260682 A1 | 10/2008 | Rose et al. | |
| 2009/0062387 A1 | 3/2009 | Caswell et al. | |
| 2009/0258090 A1 | 10/2009 | Cleveland | |
| 2009/0232943 A1 | 12/2009 | Johnson et al. | |
| 2009/0324736 A1 | 12/2009 | Johnson et al. | |
| 2010/0178360 A1 | 7/2010 | Deviere et al. | |
| 2010/0255122 A1 | 10/2010 | Garren et al. | |
| 2011/0189091 A1 | 8/2011 | Bachwich | |
| 2012/0135090 A1 | 5/2012 | Seldon et al. | |
| 2012/0195980 A1 | 8/2012 | Shaver | |
| 2013/0102661 A1 | 4/2013 | Chan | |
| 2013/0121916 A1 | 5/2013 | Baroni et al. | |
| 2013/0136806 A1 | 5/2013 | Zanarotti et al. | |
| 2013/0149390 A1 | 6/2013 | Gorelick et al. | |
| 2013/0156871 A1 | 6/2013 | Keller | |
| 2013/0304016 A1 | 11/2013 | Kouno et al. | |

FOREIGN PATENT DOCUMENTS

| | | | |
|---|---|---|---|
| CN | 1093259 | 4/1998 | |
| CN | 1371688 | 10/2002 | |
| CN | 1813674 | 8/2006 | |
| CN | 101450074 | 6/2009 | |
| CN | 101496589 | 8/2009 | |
| CN | 101766563 | 7/2010 | |
| CN | 102805752 A | 5/2012 | |
| CN | 102600201 | 7/2012 | |
| CN | 102772427 A | 11/2012 | |
| CN | 102805753 A | 12/2012 | |
| CN | 103550212 | 2/2014 | |
| CN | 103550249 A | 2/2014 | |
| DE | 3807712 A | 2/1989 | |
| DE | 10239161 | 3/2004 | |
| DE | 202010016398 U1 | 12/2010 | |
| EP | 0436061 | 7/1991 | |
| EP | 0441786 | 10/1995 | |
| EP | 2322190 A1 | 5/2011 | |
| GB | 2471954 | 1/2011 | |
| GB | 2471954 A * | 1/2011 | A61K 31/198 |
| IN | 1995MA00189 | 2/2005 | |
| IN | 00090MA1995 A | 4/2010 | |
| IN | 00458CH2005 | 1/2011 | |
| JP | 6295194 | 5/1987 | |
| JP | 1-125319 A | 5/1989 | |
| JP | 1-132527 | 5/1989 | |
| JP | 2630423 | 11/1989 | |
| JP | 3-168067 | 7/1991 | |
| JP | 4-112830 A | 4/1992 | |
| JP | H04112830 A | 4/1992 | |
| JP | 2557111 | 9/1996 | |
| JP | 11-228423 A | 8/1999 | |
| JP | 2002-265372 A | 9/2002 | |
| JP | 2003-73260 A | 3/2003 | |
| JP | 3439559 B2 | 6/2003 | |
| JP | 3457012 | 8/2003 | |
| JP | 2004-323456 | 11/2004 | |
| JP | 2004-323479 | 11/2004 | |
| JP | 2006507281 A | 3/2006 | |
| JP | 3850891 | 9/2006 | |
| JP | 2012-207002 | 10/2012 | |
| RU | 2178292 C1 | 4/2001 | |
| WO | WO1987/00754 | 2/1987 | |
| WO | WO1989/05659 | 6/1989 | |
| WO | WO2000/49414 | 8/2000 | |
| WO | WO2002/00043 | 1/2002 | |
| WO | WO2003/037298 | 5/2003 | |
| WO | 2004037292 A1 | 5/2004 | |
| WO | WO2004/037292 | 5/2004 | |
| WO | WO2005/049049 | 6/2005 | |
| WO | WO2005/120501 | 12/2005 | |
| WO | WO2007/037803 | 4/2007 | |
| WO | WO2007/044681 | 4/2007 | |
| WO | WO2009/052256 | 4/2009 | |
| WO | WO2009056114 A2 | 5/2009 | |
| WO | WO2010/123901 | 10/2010 | |
| WO | WO2011/007153 | 1/2011 | |
| WO | WO2011/107007 A1 | 9/2011 | |
| WO | WO2012/059725 A1 | 5/2012 | |
| WO | WO2012059724 A1 | 5/2012 | |
| WO | WO2012/104617 A1 | 8/2012 | |
| WO | WO2012/120027 | 9/2012 | |
| WO | WO2012/123720 | 9/2012 | |
| WO | WO2013/039477 | 3/2013 | |
| WO | WO2013/059881 | 5/2013 | |
| WO | WO2013/119002 | 8/2013 | |

OTHER PUBLICATIONS

Adams et al., "Bisacodyl Reduces the Volume of Polyethylene Glycol Solution Required for Bowel Preparation", Dis. Colon Recutm, 37(3): 229-233 (1994).

Agus et al., "Stromal Cell Oxidation: A Mechanism by Which Tumors Obtain Vitamin C", Cancer Research, 59: 4555-4558 (1999).

Agus et al., Vitamin C Crosses the Blood-Brain Barrier in the Oxidized Form Through the Glucose Transporters, J. Clin. Invest., 100(11): 2842-2848 (1997).

Auer et al., "Relative hyperoxaluria, crystalluria and haematuria after megadose ingestion of vitamin C", Eur. J. Clin. Invest., 28: 695-700 (1998).

Auer et al., "The Effect of Ascorbic Acid Ingestion on the Biochemical and Physico-chemical Risk Factors Associated with Calcium Oxalate Kidney Stone Formation", Clin. Chem. Lab. Med., 36(3): 143-148 (1998).

Barkun et al., "Commonly used preparations for colonoscopy: Efficacy, tolerability and safety—A Canadian Association of Gastroenterology position paper", Can. J. Gastroenterol., 20(11): 699-710 (2006).

Blanchard et al., "Pharmacokinetic perspectives on megadose of ascorbic acid", Am. J. Clin. Nutr., 66: 1165-1171 (1997).

Bokemeyer, B. "Koloskopievorbereitung in der ambulanten Gastroenterologie", Verdauungskranheiten, 18: 17-24 (2000).

Calabria et al., "Effect of vitamin C supplements on urinary oxalate and pH in calcium stone-forming patients", Kidney International, 63: 1066-1071 (2003).

Cho et al., "A Prospective Randomized Trial Comparing Divided Dose of Polyethylene Glycol (PEG) Solution With Stimulant Laxative Plus Low Dose PEG Solution For Colon Cleansing", Endoscopy, 37(Suppl. I) A275 (2005).

Doward et al., "Development and validation of the Bowel Cleansing Impact Review (BOCLIR)", Frontline Gastroenterology, 4: 112-119 (2013).

Duconge et al., "Pharmacokinetics of Vitamin C: insights into the oral and intravenous administration of ascorbate", PRHSJ, 27(1): 7-19 (2008).

Graumlich et al., "Pharmacokinetic Model of Ascorbic Acid in Healthy Male Volunteers During Depletion and Repletion", Pharmaceutical Research, 14(9): 1133-1139 (1997).

Gruss et al., "Pharmacokinetic Modelling of a Healthy Volunteer Study for the Assessments of the Ascorbic Acid Effects in PEG+E Containing Gut Cleansing Solutions", Gastrointest. Endosc., 67(5): AB324-AB325 (2008).

(56) References Cited

OTHER PUBLICATIONS

Gruss et al., Pharmacokinetic Modelling of a Healthy Volunteer Study for the Assessments of the Ascorbic Acid Effects in PEG+E Containing Gut Cleansing Solutions Poster (2008).

Halphen et al., "Validation of the Harefield Cleansing Scale: a tool for the evaluation of bowel cleansing quality in both research and clinical practice", Gastrointestinal Endoscopy, 78(1): 121-131 (2013).

Hathcock et al., "Vitamins E and C are safe across a broad range of intakes", Am. J. Clin. Nutr., 81: 736-745 (2005).

Hawes et al., A consensus document on bowel preparation before colonoscopy: Prepared by a Task Force From The American Society of Colon and Rectal Surgeons (ASCRS), the American Society for Gastrointestinal Endoscopy (ASGE), and the Society of American Gastrointestinal and Endoscopic surgeons (SAGES),63(7): 894-909 (2006).

Hickey et al., "Pharmacokinetics of oral vitamin C", Journal of Nutritional & Environmental Medicine, 17(3): 169-177 (2008).

Hornig et al., "Absorption of Large, Single, Oral Intakes of Ascorbic Acid", Internat. J. Vit. Nutr. Res., 50: 309-314 (1980).

Jackson et al., "Screening for Vitamin C in the Urine: Is it Clinically Significant?", Journal of Orthomolecular Medicine, 20(4): 259-261 (2005).

Jacob et al., Biochemical indices of human vitamin C status 1-3, Am. J. Clin. Nutr., 46: 818-826 (1987).

Kallner et al., "Steady-state turnover and body pool of ascorbic acid in man", Am. J. Clin. Nutr., 32: 530-539 (1979).

Lamarche et al., "Vitamin C-Induced Oxalate Nephropathy", International Journal of Nephrology, 1-4 (2011).

Levine et al., "Vitamin C pharmacokinetics in healthy volunteers: Evidence for a recommended dietary allowance", Proc. Natl. Acad. Sci. USA, 93: 3704-3709 (1996).

Levine et al., "Vitamin C: A Concentration-Function Approach Yields Pharmacology and Therapeutic Discoveries", American Society for Nutrition Adv. Nutr., 78-88 (2011).

Lykkesfeldt, "Cancer Epidemiology Biomarkers & Prevention", Cancer Epidemiology, Biomarkers and Prevention, 16: 2513-2516 (2007).

Malo et al., "Glucose Modulates Vitamin C Transport in Adult Human Small Intestinal Brush Border Membrane Vesicles", American Society for Nutritional Sciences, 63-69 (1999).

Mamula et al., "Colonoscopy preparation", Gastrointestinal Endoscopy, 69(7): 1201-1209 (2009).

Massey et al., "Ascorbate Increases Human Oxaluria and Kidney Stone Risk", American Society for Nutritional Sciences 1673-1677 (2005).

May, J., "The SLC23 family of ascorbate transporters: ensuring that you get and keep your daily dose of vitamin C", British Journal of Pharmacology, 164: 1793-1801 (2011).

May et al., "Nitric Oxide Mediates Tightening of the Endothelial Barrier by Ascorbic Acid", Biochem. Biophys. Res. Commun., 404(2); 701-705 (2011).

Mouly et al., "Effects of the Addition of High-Dose Vitamin C to Polyethylene Glycol Solution for Colonic Cleansing: A Pilot Study in Healthy Volunteers", Current Therapeutic Research, 66(6): 286-500 (2005).

MOVIPREP, Summary of Product Characteristics as revised Jan. 18, 2011.

Ohno et al., "High-dose Vitamin C (Ascorbic Acid) Therapy in the Treatment of Patients with Advanced Cancer", Anticancer Search, 29: 809-816 (2009).

Owaki et al., "Method for Pretreatment with Magcorol P Solutions", Therapeutic Research, 14: (Suppl. 2): 189-191 (1993).

Padayatty et al., "Vitamin C Pharmacokinetics: Implications for Oral and Intravenous Use", Annals of Internal Medicine, 140(7): 533-538 (2004).

Parente et al., "Bowel preparation before colonoscopy in the era of mass screening for colo-rectal cancer: A practical approach", Digestive and Liver Disease, 41: 87-95 (2009).

Park et al., "Efficacy and Tolerability of Split-Dose Magnesium Citrate: Low-Volume (2 Liters) Polyethylene Glycol vs. Single- or Split-Dose Polyethlene Glycol Bowel Preparation for Morning Colonoscopy", Am. J. Gastroenterol., 105: 1319-1326 (2010).

Piotrovskij et al., "The Use Of A Nonlinear Absorption Model in the Study of Ascorbic Acid Bioavailability in Man", Biopharmaceutics and Drug Disposition, 14: 429-442 (1993).

Puxty et al., "Golytely: A New Approach To Faecal Impaction in Old Age", Age and Ageing, 15: 182-184 (1986).

Ralli et al., "The Mechanism of the Excretion of Vitamin C by the Human Kidney", Journal of Clinical Investigation, 19(5): 765-770 (1940).

Riordan et al., Clinical and Experimental Experiences with Intravenous Vitamin C, Journal of Orthomolecular Medicine, 15(4): 201-213 (2000).

Schanz et al., "Bowel Preparation for Colonoscopy with Sodium Phosphate Solution versus Polyethylene Glycol-Based Lavage: A Multicenter Trial", Diagnostic and Therapeutic Endoscopy, 2008: 1-6 (2008).

Vitamin and Mineral Requirements in Human Nutrition, Second Edition, 2004 Report of a Joint FAO/WHO Expert Consultation, Bangkok, Thailand, Sep. 21 to 30, 1998.

Wexner et al., "ASGE/ASCRS/SAGES Guidelines for Bowel Preparation Prior to Colonoscopy" (2006).

Wexner et al., "Guideline Summary NGC-5139", A Consensus Document on Bowel Preparation Before Colonoscopy, (2011).

Smith, Lendon H., "Clinical Guide to the Use of Vitamin C", 2004.

Hawes et al., Gastrointestinal Endoscopy, 63(7): 894-909 (2006).

Arora et al., "Use of Powder PEG-3350 as a Sole Bowel Preparation: Clinical Case Series of 245 Patients", Gastroenterology & Hepatology, 4(7): 489-492 (2008).

Marmo, Riccardo et al., "Effective bowel cleansing before colonoscopy: a randomized study of split-dosage versus non-split dosage regimens of high-volume versus low-volume polyethylene glycol solutions", Gastrointestinal Endoscopy, vol. 72, Issue 2: 313-320 (2010).

Bitoun, A. et al., Results of a prospective randomised multicentre controlled trial comparing a new 2-L ascorbic acid plus polyethylene glycol and electrolyte solution vs. sodium phosphate solution in patients undergoing elective colonoscopy, Aliment Pharmacol Ther 24, 1631-1642 (2006).

Chiu, Han-Mo, M.D., et al., The Impact of Colon Preparation Timing on Colonoscopic Detection of Colorectal Neoplasms—A Prospective Endoscopist-Blinded Randomized Trial, Am J Gastroenterol 101: 2719-2725 (2006).

Church, James M., M.D., Effectiveness of Polyethylene Glycol Antegrade Gut Lavage Bowel Preparation for Colonoscopy— Timing is the Keyl, Dis Colon Rectum 41: 1223-1225 (1998).

\* cited by examiner

COLON CLEANSING COMPOSITIONS AND METHOD OF USE

CROSS-REFERENCE TO RELATED APPLICATIONS

This application is a continuation of U.S. application Ser. No. 16/028,819, filed Jul. 6, 2018, which is a continuation of U.S. application Ser. No. 15/454,132, filed Mar. 9, 2017, now U.S. Pat. No. 10,016,504, which is a continuation of U.S. application Ser. No. 15/141,054, filed Apr. 28, 2016, now U.S. Pat. No. 9,707,297, which is a continuation of U.S. application Ser. No. 14/657,495, filed Mar. 13, 2015, now U.S. Pat. No. 9,326,969, which is a continuation of U.S. application Ser. No. 14/223,127, filed Mar. 24, 2014, now U.S. Pat. No. 8,999,313, which application is a continuation of international (PCT) application no. PCT/EP2013/068738, filed Sep. 10, 2013, and designating the US, which claims priority to U.S. provisional patent application nos. 61/699,488, filed Sep. 11, 2012, and 61/787,366, filed Mar. 15, 2013.

FIELD OF THE INVENTION

The present invention relates to a method of cleansing the colon using colon cleansing solutions, and compositions and kits associated therewith. Colon cleansing compositions are also known as lavage solutions, bowel cleansers, purgatives or colonic evacuants.

1. BACKGROUND

Colon or bowel cleansing is important before numerous surgical or diagnostic procedures, including colonoscopy, barium enema examination, sigmoidoscopy and colon surgery. Such procedures are often carried out on an outpatient basis and thus it is desirable that the colon cleansing be carried out by the patient at home, prior to arrival at the hospital or surgery where the procedure is to take place. It is therefore important that patient compliance is good without medical supervision if satisfactory colon cleansing is to be achieved prior to the procedure.

Intestinal lavage, in which a large volume of an aqueous electrolyte solution containing sodium sulphate and polyethylene glycol is ingested, is one of the most common methods for colon cleansing. These osmotically active agents are non-absorbable or only poorly absorbable and thus retain water in the bowel, resulting in copious diarrhoea and cleansing of the colon.

For effective cleansing, many of these compositions must be ingested in quantities of between 2 to 4 litres. The unpleasant taste of these compositions combined with the large volumes required to be ingested often contributes to nausea or vomiting, resulting in poor patient compliance and failure to consume the full volume of solution. Poor patient compliance can lead to inadequate preparation of the colon which can, in turn, lead to cancellation or repetition of the colonoscopy becoming necessary or, worse, non-detection of lesions or polyps indicative of cancer risk.

A number of improved colon cleansing compositions are described in WO 2004/037292. A colon cleansing composition according to WO 2004/037292 that comprises polyethylene glycol 3350, sodium sulphate, an ascorbate component, electrolytes, sweetener and flavouring is commercialised as a powder for oral solution under the tradename MOVIPREP® (registered trademark of Velinor AG, a member of the Norgine group of companies). The MOVIPREP solution is effective despite being taken in a substantially lower volume than other colon cleansing solutions. Typically, only 2 litres of the solution need to be taken by an adult patient (along with additional clear fluid), a significant benefit when compared to taking 4 litres of previous solutions.

A recent advance in colon cleansing agents is provided by the product marketed as SUPREP by Braintree Laboratories, Inc. SUPRPEP contains 17.5 g sodium sulphate, 3.13 g potassium sulphate and 1.6 g magnesium sulphate and it is taken in a volume of 16 US fluid ounces (473 ml). A treatment comprises two doses of that solution.

Various regimens for the timing of ingestion of colon cleansing solutions are mentioned in the literature and in patient information leaflets that accompany colon cleansing products. For example, the MOVIPREP solution mentioned above may be taken (optionally with additional clear liquids also being taken) in the evening before the examination or procedure, or the MOVIPREP solution may be taken in a "split-dose" regimen, with approximately half of the cleansing solution being taken the evening before the examination or procedure ("first dose"), and the remainder being taken the following morning ("second dose"). Similarly, the SUPREP product mentioned above is recommended to be taken as first dose in the evening before the examination procedure, accompanied by an additional quart of water (946 ml), followed by a second dose in the morning of the procedure.

An alternative to the lavage solutions described above is provided by low volume hypertonic salt solutions. Examples include Fleet's phosphosoda product and sodium picosulphate solutions. These are very concentrated salt solutions and patients need ingest only a small volume of them (around 100 ml). However, these products have been associated with a hypo-osmolar state and electrolyte imbalance in subjects, particularly hyponatremia. They are particularly counter-indicated in subjects with kidney problems.

Despite the advances that have been made, all lavage-type colon cleansing products on the market continue to require a subject to ingest a large volume of solution (2 litres in the case of the MOVIPREP solution). Many subjects find the ingestion of a large volume unpleasant or difficult and poor patient compliance thus remains a problem. There remains a need for alternative colon cleansing solutions that are effective when ingested in small volumes, but do not cause electrolyte imbalances in subjects. There also remains a need for colon cleansing solutions that are more pleasant to subjects to ingest, whilst retaining good cleansing effectiveness.

2. SUMMARY OF THE INVENTION

The invention provides, in a first aspect, a colon cleansing solution comprising:
a) 300 to 800 mmol per litre ascorbate anion provided by a mixture of:
  (i) ascorbic acid and
  (ii) one or more salts of ascorbic acid
  the components (i) and (ii) being present in a molar ratio of from 1:4.5 to 1:7.0; and
b) 10 to 200 g per litre polyethylene glycol.

The solution of the invention has a surprisingly palatable taste. The particular ratio of ascorbic acid to salt of ascorbic acid enables the salty taste of ascorbate salt to be balanced by sourness from acid to a palatable extent, whilst at the same time not reducing the osmotic effect of the ascorbate component or making the solution too sour. The solution is highly effective as a colon cleansing solution when ingested in a lower volume than many prior art solutions, and it has a good tolerability profile.

Figure 1:
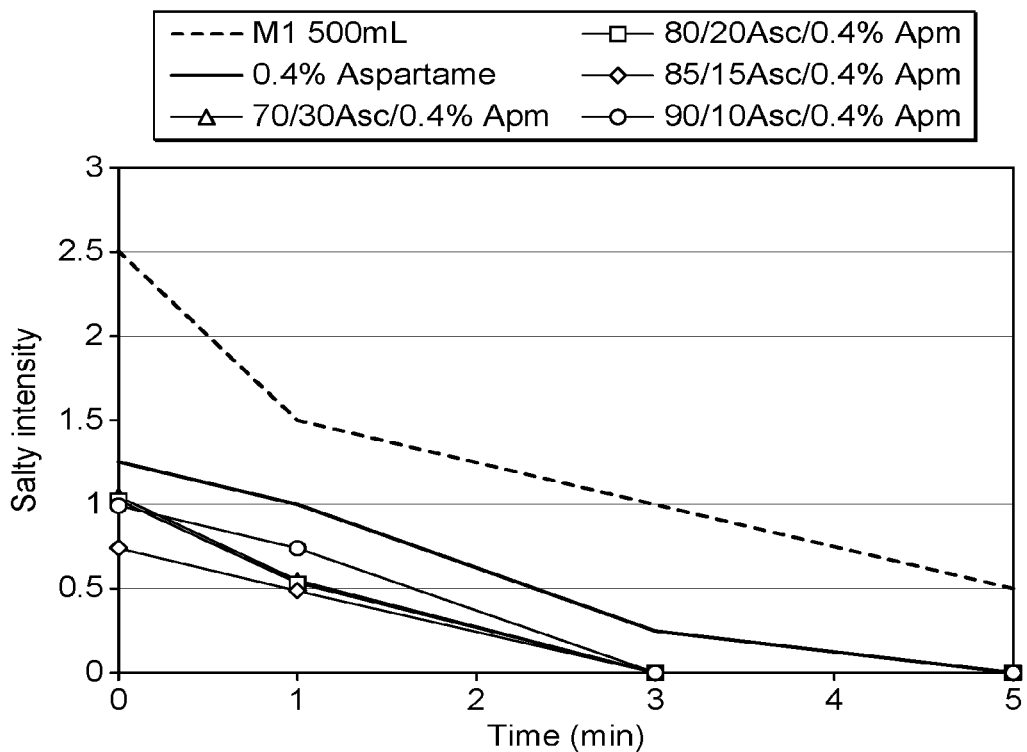
FIG. 1 is a graph showing the results of the taste testing of the solutions set forth in Table 1 herein.

3. DETAILED DESCRIPTION a) Contents of Solutions

The solutions of the invention are aqueous solutions. The mixture of ascorbic acid and one or more salts of ascorbic acid will, for convenience, be referred to herein as the "ascorbate component". Suitable salts of ascorbic acid include alkali metal salts and alkaline earth metal salts. For example, a salt may be selected from sodium, potassium, magnesium and calcium salts. For example, preferred salts of ascorbic acid include sodium ascorbate, potassium ascorbate, magnesium ascorbate and calcium ascorbate. The molar ratio between (i) the ascorbic acid and (ii) the one or more salts of ascorbic acid is the molar ratio of the ascorbate moieties; for example, magnesium ascorbate comprises two moles of ascorbate per mole of salt; for the ratio purposes, it is the number of moles of ascorbate that is counted. Particularly preferred salts of ascorbic acid are magnesium ascorbate and sodium ascorbate, for example sodium ascorbate. In one embodiment, the solution comprises ascorbic acid and sodium ascorbate (and preferably no further ascorbate).

Preferably, the molar ratio of the components (i) and (ii) is from 1:4.75 to 1:6.75; more preferably from 1:5.0 to 1:6.0; for example from 1:5.40 to 1:5.80; for example 15:85.

The solution of the invention preferably comprises ascorbate anion in a concentration of: 300-700 mmol per litre, for example 350-650 mmol per litre, for example 450-600 mmol per litre.

A solution of the invention may comprise 50 to 140 g/litre of ascorbate component. For example, a solution of the invention comprises 60 to 140 g/litre, for example 80 to 130 g/litre, for example 80 to 120 g/litre, for example 100 to 120 g/litre of ascorbate component.

Ascorbic acid has a molecular weight of 176 g/mol. Sodium ascorbate has a molecular weight of 198 g/mol. Accordingly, a mixture of ascorbic acid and sodium ascorbate in a molar ratio of from 1:4.5 to 1:7.0 has ascorbic acid and sodium ascorbate present in a weight ratio of 1:5.063 to 1:7.875. For example, the weight ratio can be 1:5.344 to 1:7.594; more preferably from 1:5.625 to 1:6.75; for example from 1:6.075 to 1:6.525, for example 1:6.38. For example, a solution of the invention may comprise from 6 to 25 g/litre of ascorbic acid and 50 to 120 g/litre of sodium ascorbate, for example 12 to 20 g/litre of ascorbic acid and 80 to 120 g/litre of sodium ascorbate (with the ratio between them being as mentioned above). For example, a solution of the invention may comprise from 14 to 16 g g/litre of ascorbic acid and 92 to 100 g/litre of sodium ascorbate.

Potassium ascorbate has a molecular weight of 214 g/mol. Accordingly, a mixture of ascorbic acid and potassium ascorbate in a molar ratio of from 1:4.5 to 1:7.0 has ascorbic acid and potassium ascorbate present in a weight ratio of 1:5.471 to 1:8.511. For example, the weight ratio can be 1:5.776 to 1:8.208; more preferably from 1:6.080 to 1:7.295; for example from 1:6.565 to 1:7.052, for example 1:6.896. For example, a solution of the invention may comprise from 6 to 25 g/litre of ascorbic acid and 50 to 125 g/litre of potassium ascorbate, for example 6 to 12 g/litre of ascorbic acid and 80 to 120 g/litre of potassium ascorbate.

Magnesium ascorbate has a molecular weight of 374.5 g/mol and each mole of magnesium ascorbate provides two moles of ascorbate. Accordingly, a mixture of ascorbic acid and magnesium ascorbate in a molar ratio of from 1:4.5 to 1:7.0 (of ascorbate anion) has ascorbic acid and magnesium ascorbate present in a weight ratio of 1:4.794 to 1:7.457. For example, the weight ratio can be 1:5.061 to 1:7.191; more preferably from 1:5.326 to 1:6.397 for example from 1:5.753 to 1:6.179, for example 1:6.042. For example, a solution of the invention may comprise from 6 to 25 g/litre of ascorbic acid and 45 to 120 g/litre of magnesium ascorbate, for example 6 to 12 g/litre of ascorbic acid and 75 to 115 g/litre of magnesium ascorbate.

Depending on the pH of the solution, some ascorbate anion may be protonated and thus exist as free ascorbic acid in solution. At the pH of solutions that would typically be administered, only a very minor proportion of ascorbate is protonated. In calculations of concentrations of "ascorbate anion" herein, the concentration of "ascorbate anion" is taken as the total concentration of all ascorbate anion present, including the proportion that is protonated.

The cleansing solution comprises polyethylene glycol. The polyethylene glycol (PEG) may, for example, have an average molecular weight of 2000 to 8000, for example 2500 to 4500 Da, for example 2680 to 4020 Da, for example 3000 to 4000 Da. For example, the PEG may be PEG 3350 or PEG 4000 as defined in national pharmacopeias. PEG8000 may also be used. Further examples of suitable PEGs recognized in some national pharmacopeias include Macrogols, for example Macrogol 3350 or Macrogol 4000.

The cleansing solution comprises 10 to 200 g per litre of PEG. Preferably, the solution comprises 20 to 160 g per litre of PEG, more preferably 40 to 120 g per litre, for example 60 to 100 g per litre, for example 75 to 85 g per litre, for example 80 g per litre.

The cleansing solution may additionally comprise one or more of:
   c) one or more electrolytes;
   d) one or more alkali metal or alkaline earth metal sulphates;
   e) one or more flavouring agents;
   f) one or more sweeteners.

The cleansing solution may comprise one or more electrolytes. Electrolytes include salts of sodium, potassium, calcium and magnesium, particularly sodium and potassium; and salts of chloride, iodide, bicarbonate and carbonate, particularly chloride. Preferred electrolytes are sodium chloride and potassium chloride. In an embodiment, the solution is essentially free from sodium bicarbonate, for example essentially free from any bicarbonate.

For example, the solution may comprise sodium chloride at a concentration of 1 to 10 g per litre. For example, sodium chloride may be present at a concentration of 3 to 8 g per litre, for example 4 to 7 g per litre; for example 6.0 to 6.8 g per litre; for example 5.6 g per litre or 6.4 g per litre.

For example, the solution may comprise potassium chloride at a concentration of 1 to 10 g per litre. For example, potassium chloride may be present at a concentration of 1 to 7 g per litre, for example 1.5 to 5 g per litre, for example 1.5 to 3 g per litre, for example 2.0 to 2.8 g per litre; for example 2.4 g per litre or 2.6 g per litre.

In an embodiment, the solution comprises sodium chloride and potassium chloride. They can be present in the amounts mentioned immediately above. For example, sodium chloride may be present at a concentration of 4 to 7 g per litre and potassium chloride may be present at a concentration of 1.5 to 3 g per litre.

The cleansing solution may comprise one or more alkali metal sulphates, alkaline earth metal sulphates or a mixture thereof (herein referred to as a "sulphate component"). An alkali metal or alkaline earth metal sulphate may, for example, be selected from sodium sulphate, potassium sulphate and magnesium sulphate. The solution may comprise more than one of sodium sulphate, potassium sulphate and magnesium sulphate, for example all three. Preferably, the sulphate component is or includes sodium sulphate.

For example, the solution may comprise a sulphate component at a concentration of 2 to 20 g per litre, for example 5 to 15 g per litre, for example 8 to 15 g per litre, for example 10 to 14 g per litre, for example 12 g per litre. The one or more sulphate salts may be provided in any pharmaceutically acceptable form: they may each be anhydrous, or be in a hydrated form. The weights mentioned herein refer to the weight of the sulphate salt excluding any water of hydration.

In an alternative preferred embodiment, the solution does not comprise a sulphate component; that is to say that the solution is essentially free from alkali metal sulphates and alkaline earth metal sulphates; in particular essentially free from sodium sulphate, potassium sulphate and magnesium sulphate.

Herein, the term "essentially free from" a component means that the named component is present at a level that is below the level that has any functional effect in the solution of the invention in its use; for example, the named component may be at a level that is below the level at which it has a measurable clinical effect. For example, it may mean that the component is present at a level of less than 0.1 g per litre; for example less than 0.03 g per litre; for example less than 0.01 g per litre, for example less than 0.003 g per litre, for example less than 0.001 g per litre.

In the solutions of the invention described herein, the quantities of the individual components recited do not include any solutes that may be present in the water used to prepare the solutions, for example, in hard water areas there may be significant amounts of Ca' and Mg' carbonates, bicarbonates or sulphates present in tap water.

The cleansing solution preferably includes a flavouring agent. A flavouring for use in compositions of the invention should preferably mask saltiness, be relatively sweet but not excessively so, and be stable in the composition. A flavouring makes the solutions more palatable and thus aids patient compliance. Preferred flavourings include lemon e.g. Ungerer Lemon (available from Ungerer Limited, Sealand Road, Chester, England CH1 4LP), strawberry e.g. Ungerer Strawberry, grapefruit e.g. Ungerer Grapefruit flavouring powder, blackcurrant e.g. Ungerer Blackcurrant, pineapple e.g. IFF (International Flavours and Fragrances) Pineapple flavouring powder, orange eg Firmenich Orange, vanilla/lemon and lime e.g. IFF Vanilla and Givaudin Roure Lemon and Lime Flav-o-lok, fruit punch eg Ungerer fruit punch, citrus punch, mango, and berry. Those and further suitable flavourings are available from International Flavours and Fragrances Inc. (Duddery Hill, Haverhill, Suffolk, CB9 8LG, England), Ungerer & Company (Sealand Road, Chester, England CH1 4LP) or Firmenich (Firmenich UK Ltd., Hayes Road, Southall, Middlesex UB2 5NN). More preferred flavourings are lemon, kiwi, strawberry, grapefruit, orange, fruit punch and mango. Citrus flavour, orange grapefruit flavour and orange flavour are particularly preferred.

The amount of flavouring required depends on the nature and strength of the flavouring in question. Typically, it is 0.05 to 4.5 g per litre, for example 0.05 to 2.0 g per litre, for example 0.2 to 1.8 g per litre, for example 1.0 to 1.8 g per litre, for example 3.0 to 4.5 g per litre, for example 0.3 g per litre or 1.2 g per litre, for example 3.2 or 4.2 g per litre.

The cleansing solution preferably includes a sweetener. Sugar-based sweeteners are generally not suited for colon cleansing compositions because the delivery of unabsorbed sugars to the colon provides a substrate for bacteria. Such sugars may be metabolised by the bacteria to form explosive gases such as hydrogen and methane. The presence of explosive gases in the colon can be highly dangerous when electrical apparatus is to be used during colonoscopy or other procedures. Preferred sweeteners include aspartame, acesulfame potassium (acesulfame K), sucralose and saccharine, and/or combinations thereof. For example, compositions of the invention may comprise one or both of aspartame and acesulfame potassium (acesulfame K). For example, compositions of the invention may comprise one or both of sucralose and acesulfame potassium (acesulfame K). In a preferred embodiment, the solution comprises aspartame or sucralose, for example aspartame.

Alternatively, compositions of the invention can be essentially free from added sweeteners, for example to minimize the number of different components in the compositions.

A souring agent (for example citric acid) may be present as a taste enhancer. A souring agent is a component that imparts a sourness to a composition. Other souring agents include malic acid, acetic acid, tartaric acid, gluconodeltalactone, phosphoric acid, succinic acid, phytic acid, lactic acid or salts thereof. The souring agent (for example citric acid) may be provided in an encapsulated form. The encapsulation provides a coating that isolates the souring agent from other components and from air and moisture prior to its use. Several encapsulated forms of citric acid, or other souring agents, are commercially available. For example, the encapsulation may be with a water-soluble coating.

The amount of sweetener required depends on the nature and strength of the sweetener being considered. Typically, it is 0.10 to 4 g per litre. For example, the sweetener may be aspartame at 0.5 to 4 g per litre, for example 2.5 to 4.0 g per litre, for example 3.0 g per litre, for example 3.86 g per litre. Those quantities of aspartame are particularly suitable when used with orange flavouring, for example orange flavouring at 0.2 to 1.8 g per litre, for example 1.0 to 1.8 g per litre, for example 0.3 g per litre, 0.875 g per litre or 1.2 g per litre. For example, the sweetener may be aspartame at 1.0 to 2.5 g per litre, for example 1.5 to 2.0 g per litre, for example 1.75 g per litre.

The invention thus provides a colon cleansing solution comprising:
  a) 300 to 800 mmol per litre ascorbate anion provided by a mixture of
    (i) ascorbic acid and
    (ii) one or more salts of ascorbic acid
    the components (i) and (ii) being present in a molar ratio of from 1:4.5 to 1:7.0;
  b) 10 to 200 g per litre PEG.
  c) one or more electrolytes;
  d) optionally one or more alkali metal or alkaline earth metal sulphates;
  e) optionally one or more flavouring agents; and
  f) optionally one or more sweeteners.

It will be apparent to the reader of this specification, that the term "comprising" and grammatical variations thereof, in relation to embodiments of the invention described, may be substituted in all cases (unless the context dictates otherwise) with the term "consisting essentially of" or "consisting of". In the case of a solution that "consists of" or "consists essentially of" the stated components, the balance is in each case made up of water.

In particular, the invention provides a colon cleansing solution comprising:
a) 300 to 800 mmol per litre ascorbate anion provided by a mixture of
   (i) ascorbic acid and
   (ii) one or more salts of ascorbic acid
   the components (i) and (ii) being present in a molar ratio of from 1:4.5 to 1:7.0;
b) 10 to 200 g per litre PEG having an average molecular weight of 3000 to 4000 Da;
c) sodium chloride and potassium chloride;
d) optionally sodium sulphate;
e) optionally one or more flavouring agents; and
f) optionally one or more sweeteners.

Each of c) and d) may be present in the concentrations described above. Each of e) and f) may be as described above and/or be in the concentrations described above.

In particular, the invention provides a colon cleansing solution comprising:
a) 300 to 800 mmol per litre ascorbate anion provided by a mixture of
   (i) ascorbic acid and
   (ii) one or more salts of ascorbic acid
   the components (i) and (ii) being present in a molar ratio of from 1:4.5 to 1:7.0;
b) 10 to 200 g per litre PEG having an average molecular weight of 3000 to 4000 Da;
c) sodium chloride and potassium chloride;
e) one or more flavouring agents; and
f) one or more sweeteners.

In one embodiment, one or more components of c), d) (when present), e) and f) are present in the solution. In an alternative presentation, some or all of components c), d) (when present), e) and f) may be provided separately from the solution, for example in a tablet or capsule. For example, components c) and d) may be provided in tablet form. In an embodiment, the solution may comprise a) the ascorbate component and b) PEG, and optional flavouring and sweetener (e) and f)), and a tablet or capsule may comprise c) the one or more electrolytes (optionally with d), the one or more alkali metal or alkaline earth metal sulphates), again with optional flavouring and sweetener (e) and f). The flavouring and sweeteners need not be the same in the tablet or capsule as in the solution.

In one embodiment, the invention provides a colon cleansing solution comprising:
a)
   (i) 12 to 20 g per litre ascorbic acid and
   (ii) 80 to 120 g per litre sodium ascorbate
   the components (i) and (ii) being present in a weight ratio of from 1:5063 to 1:7.875;
b) 60 to 100 g per litre PEG having an average molecular weight of 3000 to 4000 Da;
c) 3 to 8 g per litre sodium chloride and 1 to 7 g per litre potassium chloride;
e) one or more flavouring agents; and
f) one or more sweeteners.

In an embodiment, the solution consists essentially of those components; that is to say that it does not contain any further components in significant quantities. The solution may, for example, not contain any sulphate.

For example, the invention provides a colon cleansing solution consisting essentially of:
a)
   (i) 14 to 16 g per litre ascorbic acid and
   (ii) 92 to 100 g per litre sodium ascorbate
b) 75 to 85 per litre PEG having an average molecular weight of 3000 to 4000 Da;
c) 6.0 to 6.8 g per litre sodium chloride and 2.0 to 2.8 g per litre potassium chloride;
e) one or more flavouring agents; and
f) one or more sweeteners.

For example, the invention provides a colon cleansing solution consisting essentially of:
a)
   (i) 15.08 g per litre ascorbic acid and
   (ii) 96.22 g per litre sodium ascorbate
b) 80 g per litre PEG having an average molecular weight of 3000 to 4000 Da;
c) 6.4 g per litre sodium chloride and 2.4 g per litre potassium chloride;
e) one or more flavouring agents; and
f) one or more sweeteners.

For example, the flavouring and sweetener may be 1.20 g per litre orange flavour and 3.86 g per litre aspartame. For example, the flavouring and sweetener may be 3.20 g per litre citrus flavour and 1.75 g per litre aspartame. For example, the flavouring and sweetener may be 4.20 g per litre orange grapefruit flavour and 1.75 g per litre aspartame.

Preferably, the colon cleansing solution is hyper-osmotic. That is to say that it has a higher osmotic strength than blood in the human body. It may, for example have a measured osmolality in the range 500 to 2000 mOsmol/kg. For example, the osmolality may be in the range 700 to 1800 mOsmol/kg. For example, the solutes in 500 ml of the solution may have a measured V(350) value of from 1000 to 2000 ml, for example from 1300 to 2000 ml, for example from 1400 to 1900 ml, and be in a volume of 400 to 600 ml, for example 500 ml. The V(350) value is the volume of water that is required to provide a solution with an osmolality of 350 mOsmol/kg, the total volume being the final volume after a volume water has been added to a solution having an initial volume.

Osmolality can be measured in various ways. In general, either freezing point depression or vapour-pressure alteration is used. For example, an Advanced Instruments, Inc Model 3250 osmometer (a freezing point depression device) can be used. Vapour pressure measurement can also be used, for example using an ELITech Group Vapro 5600 device. Osmolality values cited herein are preferably taken to be values measured using a freezing point depression osmometer, for example using an Advanced Instruments, Inc Model 3250 osmometer following standard operating procedure.

The invention provides a colon cleansing solution comprising:
a) 300 to 800 mmol per litre ascorbate anion provided by a mixture of
   (i) ascorbic acid and
   (ii) one or more salts of ascorbic acid
   the components (i) and (ii) being present in a molar ratio of from 1:4.5 to 1:7.0; and
b) 10 to 200 g per litre PEG having an average molecular weight of 3000 to 4000 Da;
and 500 ml of the solution having a V(350) osmolality value of from 1300 to 2300 ml.

For example, 500 ml of the solution may have a V(350) osmolality value of from 1500 to 2100 ml, for example from 1700 to 2000 ml, for example from 1800 to 1900 ml.

b) Additional Optional Contents of Solutions

Unless it is stated otherwise, the solutions of the invention may include one or more additional optional components:

(i) Antioxidants

In general it is not necessary for the solutions to include preservatives or anti-oxidants. Nevertheless, low levels of anti-oxidants or preservatives may be used if required.

(ii) Laxatives

In general, the solutions described herein are effective without the need for any additional active ingredients. Nevertheless, a further active ingredient may be included if required. For example, a laxative may be present, for example a stimulant laxative. For example, bisacodyl, castor oil, senna or bisoxatin may be used. An example of a colon cleansing solution containing bisoxatin is known from WO2013001315.

(iii) Contrast Media

For certain uses, one or more contrast media can be included in a solution of the invention. Examples of contrast media include barium or iodine products, diatrizoate (marketed, for example, as HYPAQUE 50), metrizoate (marketed, for example, as ISOPAQUE 370), ioxalgate (marketed, for example, as HEXABRIX), iopamidol (marketed, for example, as ISOVUE 370), iohexol (marketed, for example, as OMNIPAQUE 350), ioxilan (marketed, for example, as OXILAN 350), iopramide (marketed, for example, as ULTRAVIST 370), iodixanol (marketed, for example, as VISIPAQUE 320) and/or a diatrizoic acid or its anionic form diatrizoate (also known as amidotrizoic acid, or 3,5-diacetamido-2,4,6-triiodobenzoic acid; marketed, for example, as HYPAQUE). Alternatively, the solution of the invention may be used in conjunction with (e.g., simultaneously, before or after) administration of a contrast agent or contrast media.

(iv) Dyes and Stains.

For certain uses (eg fluorescence endoscopy), one or more dyes or stains that are markers of particular mucosal pathology can be included in a solution of the invention. Stains may be selective. For example, hexaminolevulinate may be used, for example as its HCl salt (marketed as CYSVIEW). Other markers of colonic or rectal mucosal pathology can be used. For example methylene blue, which can stain the normal mucosa yet polyps do not stain and become more clearly visible.

Further dyes and stains that may be mentioned include: Curcumin, Riboflavin, Riboflavin-5'-phosphate, Tartrazine, Quinoline Yellow, Sunset Yellow, FCF Orange, Yellow S, Cochineal, Carminic acid, Carmines, Azorubine, Carmoisine, Ponceau 4R, Cochineal Red A, Allura Red AC, Patent Blu EV, Indigotine, Indigo carmine, Brilliant Blue FCF, Chlorophylls and chlorophyllins, Copper complexes of chlorophylls and chlorophyllins, Green S, Plain caramel, Brilliant Black BN, Black PN, Vegetable carbon, Brown HT, Carotenes, Lutein, Beetroot Red, betanin, Anthocyanins, Calcium carbonate, Titanium dioxide, Iron oxides and hydroxides, Amaranth, Brown F, Erythrosine, Lithol Rubine B and/or Red 2G. Further dyes and stains that may be mentioned include: acid fuchsine, Alba red, Alizarin cyanine green F, Alizurol purple S5, Allura Red AC, Alphazurine FGBrilliant lake red R, Dibromofluorescein, Diiodofluorescein, Eosine, Erythrosine yellowish Na, Fast green FCF, Flaming red, Fluorescein, Helindone pink CN, Indanthrene blue, Lake bordeaux B, Lithol rubin B Ca, Naphthol yellow 5, Orange II, Phloxine B, Ponceau 5X, Pyranine concentrated, Quinizarinegreen 5S, Tetrabromo-fluorescein, Tetrachlorotetrabromo fluorescein, Toney red, Uranine, Alcian Blue, Anazolene Sodium, Brilliant Green, Cantaxanthin, Carthamin, Citrus Red 2, Evan's Blue, Fast Green FCF, Indocyanine Green, Methyl Blue, Methylene Blue, N-(p-Methoxyphenyl)-p-phenylenediamine, Ponceau 3R, Ponceau SX, Pyranine, Rhodamine B, Saunders Red, Sudan Black B, Sulphan Blue, Tolonium Chloride, and/or Vital Red or equivalents or any combination thereof.

Alternatively, the solution of the invention may be used in conjunction with (e.g., simultaneously, before or after) administration of a dye or stain. A dye or a stain may be provided in slow or delayed release form, for example delayed release methylene blue (for example MMX format of colonic-released methylene blue) may be mentioned.

(v) Surfactants

A surfactant may be included in a solution of the invention. A surfactant may assist in avoiding the persistence of bubbles in the colon. Such bubbles can interfere with the visualisation of features of the colon during colonoscopy. Surfactants that may be mentioned include simethicone (or any mixture of polydimethylsiloxane and silica gel), dimethicone. Bowel cleansing solutions containing simethicone are described in WO2009052256.

(vi) Lubricants

A lubricant may be included in a solution of the invention. The inclusion of a lubricant can help with a colonoscope insertion and facilitation within the performance of the colonoscopy. Suitable lubricants include glycerol or silicone.

(vii) Biofilm-Disrupting Compounds

A biofilm disrupting compound may be included in a solution of the invention. A compound that disrupts biofilms may assist in separating an adherent polysaccharide DNA—containing layer, the so-called "biofilm" from the colonic mucosa. Removal of that layer may assist in achieving a cleaner and/or more easily visualized or stained mucosa.

Biofilm-disrupting components or agents that may be mentioned include enzymes such as deoxyribonuclease (DNase), N-acetylcysteine, alginate lyase, glycoside hydrolase dispersin B; Quorum-sensing inhibitors e.g., ribonucleic acid III inhibiting peptide, Salvadora persica extracts, Competence-stimulating peptide, Patulin and penicillic acid; peptides—cathelicidin-derived peptides, small lytic peptide, PTP-7 (a small lytic peptide, see e.g., haridia (2011) J. Microbiol. 49(4):663-8, Epub 2011 Sep. 2), Nitric oxide, neo-emulsions; ozone, lytic bacteriophages, lactoferrin, xylitol hydrogel, synthetic iron chelators, cranberry components, curcumin, silver nanoparticles, Acetyl-11-keto-P-boswellic acid (AKBA), barley coffee components, probiotics, sinefungin, S-adenosylmethionine, S-adenosyl-homocysteine, Delisea furanones, N-sulfonyl homoserine lactones and/or macrolide antibiotics or any combination thereof.

Alternatively, the solution of the invention may be used in conjunction with (e.g., simultaneously, before or after) administration of a biofilm-disrupting compound. A biofilm-disrupting compound may be administered towards the end of ingestion of the solution of the invention, or shortly after completion of ingestion of the solution of the invention, so as to disrupt the biofilm most just before the colonoscopy.

(viii) Organic Acids

Some of the osmotic load of the solution of the invention may be provided by an organic acid or salts of an organic acid other than ascorbic acid. For example, citric acid and/or salts thereof may replace some or all of the ascorbate in solutions of the invention. Throughout this description, ascorbic acid may be replaced with citric acid. A salt of ascorbate may be replaced with the salt of citrate. Sodium citrate, potassium citrate and magnesium citrate are particularly preferred.

c) Uses of Solutions of the Invention

The solutions of the invention find use in cleansing the colon or bowel. They are also useful in the treatment of faecal impaction or constipation.

When carrying out a bowel cleansing treatment, a subject typically takes a single dose or a split dose of cleansing solution. In a split-dose treatment, typically two doses are taken separated by a time interval, for example an overnight interval. Alternatively, in a split-dose treatment two doses may be taken on the same day, for example during the day before a therapeutic or surgical procedure, or during the day of a therapeutic or surgical procedure. Each dose in a split dose treatment is smaller than the dose in the single dose treatment. In a split dose treatment, the two doses may each have the same composition, or they may be different.

For a single dose treatment, the solution of the invention may be ingested in a volume of 700 to 1500 ml. For example, the subject may ingest from 750 ml to 1300 ml of the solution, for example 800 to 1200 ml, for example 900 to 1100 ml, for example 1000 ml. For example 33 or 34 US fluid ounces may be ingested. In an embodiment, the subject may ingest some additional clear fluid. The additional clear fluid may be ingested after ingesting the solution. Alternatively, the additional clear fluid may be co-administered with the intake of the solution of the invention. By "co-administered" is meant the coordinated ingestion of a solution of the invention with clear fluid; that is to say that the subject ingests some of the solution of the invention but not necessarily the whole dose, then some clear fluid and then more solution of the invention.

For a split dose treatment, the solution of the invention may be taken as one or both of the doses, each dose having a volume of 200 to 1000 ml. For example, the subject may ingest (as one of the doses) 300 ml to 1000 ml of the solution, for example 300 ml to 900 ml, for example 300 ml to 800 ml, for example 400 ml to 700 ml, for example 400 to 600 ml, for example 450 to 550 ml, for example 500 ml. For example 16 or 17 US fluid ounces may be ingested.

The combined volume of the first and second doses is preferably less than 2 litres. Preferably, it is 1750 ml or less, for example 1500 ml or less, for example 1250 ml or less. For most adult subjects, a combined volume of more than 500 ml is used, for example more than 750 ml. For example, a combined volume of from 500 ml to 1750 ml is used, for example from 750 ml to 1500 ml, for example from 1000 ml to 1500 ml, for example 1000 ml or 1250 ml. For example the first dose may have a volume of 500 ml (for example a volume of 16 or 17 US fluid ounces) or 750 ml (for example a volume of 25 or 26 US fluid ounces) and the second dose may have a volume of 500 ml (for example a volume of 16 or 17 US fluid ounces).

In an embodiment, the subject may ingest some additional clear fluid with each or either dose of colon cleansing solution. The additional clear fluid may be taken after ingesting a dose of the solution. Alternatively, the additional clear fluid may be co-administered with the intake of a dose of the solution of the invention; that is to say that the subject ingests some of the solution of the invention but not necessarily the whole dose, then some clear fluid and then more solution of the invention.

In the method, there is typically a time interval between ingesting the first dose and ingesting the second dose. Generally, the time interval is at least 4 hours, for example 6 hours or more, for example 8 hours or more. Typically, the time interval is less than 15 hours. The time interval between starting to take the first dose and starting to take the second dose may be, for example, the time between an evening and the following morning, for example 12 to 16 hours, for example 14 hours. For example, the subject may sleep (for example overnight) between taking the first and second doses.

Alternatively, the time interval between ingesting the first dose and ingesting the second dose can be at least 10 minutes, for example from 10 minutes to 4 hours, for example from 30 minutes to 4 hours, for example from 30 minutes to two hours. For example, the subject may ingest the first and second colon doses the evening before a surgical or diagnostic procedure. The time interval between ingesting the first solution and ingesting the second solution can be determined by the time it takes for the subject to experience a bowel movement. For example the subject takes the second dose when the first bowel movement has occurred after completing ingestion of the first solution. Alternatively, the subject ingests the second dose when the first bowel movement has occurred even if ingestion of the first dose is not complete.

During the ingestion of the first or second dose, or during the time interval between the ingestion of the first dose and the second dose, the subject may additionally take a stimulant laxative (also known as a prokinetic agent). A stimulant laxative can assist in bringing about good cleansing. Examples of stimulant laxatives include contact laxatives, for example bisacodyl, castor oil, senna or bisoxatin. Examples of stimulant laxatives also include additional osmotic agents for example magnesium salts, for example magnesium citrate. If a stimulant laxative is included in the regimen, the length of the time interval can be shortened. For example, it may be 10 minutes to 15 hours, for example 1 to 15 hours, for example 1 to 12 hours, for example 2 to 10 hours.

During the time interval between the administration of the first dose and the second dose, it is very likely that the subject will experience a bowel movement. Advantageously, the subject waits until the bowel movement has occurred before taking the second dose.

In a split dose treatment, the solution of the invention may be taken for one or for both of the doses. Preferably, the solution of the invention is taken as the second solution. For example, the subject may ingest 300 ml to 1000 ml of the solution of the invention as the second solution, for example 300 ml to 900 ml, for example 300 ml to 800 ml, for example 400 ml to 700 ml, for example 400 to 600 ml, for example 450 to 550 ml, for example 500 ml. For example 16 or 17 US fluid ounces may be ingested.

The first solution may be a solution of different constitution from the second solution. Thus, in a preferred embodiment of a split dose bowel cleansing treatment, a subject takes a dose of an initial cleansing solution, optionally followed by some additional clear fluid. After an interval, the subject then takes a dose of the solution of the invention, optionally followed by some additional clear fluid.

The volume of clear fluid that a subject ingests after the first or second dose may be in a range with a lower limit of 100 ml, 200 ml, 300 ml, 400 ml or 500 ml. Preferably, the lower limit is 300 ml, 400 ml or 500 ml. The volume may be in a range with an upper limit of 1200 ml, 1100 ml, 1000 ml, 900 ml or 800 ml. For example the volume may be in the range 100 ml to 1200 ml, for example 200 ml to 1100 ml, for example 300 ml to 1000 ml, for example 500 ml to 900 ml, for example 1000 ml, for example 875 ml, for example 500 ml to 800 ml. For example the volume may be in the range 300 ml to 900 ml, for example 400 ml to 800 ml, for example 500 ml to 800 ml. The additional clear fluid may be ingested in a volume of at least 500 ml. For example it may be at least 16 or 17 US fluid ounces. The instructions provided to the subject may suggest that the additional clear fluid is ingested over a period of approximately one hour, for example in 150 to 200 ml fractions every 15 to 20 minutes. The additional clear fluid may be taken after taking a dose of the solution. Alternatively, the additional clear fluid may be co-administered with the intake of a dose of the solution of the invention; for example, the subject may ingest clear fluid between fractions of the solution of the invention; for example the subject may ingest a cup of the solution of the invention, followed by a cup of clear fluid, followed by further cups of the solution of the invention.

A clear fluid for taking as the additional clear fluid, or for use as the clear fluid when making up a solution, may be any fluid that allows inspection of colonic output. The clear fluid should also not impede inspection of the colon during the colonoscopy. Typically the clear fluid is a water-based beverage, including, for example, water, lemonade, cola drinks, cordial drinks, clear fruit juices and even clear alcohol-containing beverages, for example beer. It is desirable that the clear fluid does not contain substantial amounts of or essentially any dietary fibre, as such fibre interferes with the cleansing of the colon according to the present invention. Accordingly, fruit juices, for example orange juice and kiwi juice, and fruit "squashes" should be strained before use. Clear fruit cordials, for example lime cordial or tea (for example green tea), are generally suitable. In view of the desirability of avoiding drinks containing glucose, so as to reduce the risk of explosive concentrations of hydrogen or methane building up in the gut, "diet" drinks containing no or low sugar are especially suitable, for example liquid drinks for diabetics, diet Coke®, diet lemonade, dietary carbonated drinks or dietary cordials. The most preferred clear fluid is water.

The method of the invention may be used to cleanse the colon prior to carrying out a diagnostic, therapeutic or surgical procedure on the colon, rectum or anus or elsewhere in the abdomen in a subject. The subject is most preferably a human. The diagnostic or surgical procedure may, for example, be colonoscopy (such as cap-assisted colonoscopy and/or narrow-band colonoscopy), barium enema examination, sigmoidoscopy (for example flexible sigmoidoscopy) or colon surgery. The method of the invention may be a method of cleansing the colon prior to a surgical or diagnostic procedure comprising administering the first solution and then after a time interval administering the second solution prior to said procedure.

The solutions, compositions and kits described herein also find use in the treatment of constipation and faecal impaction. They also find use in the treatment of severe bacterial infections of the bowel. The invention thus provides solutions, compositions and kits as described herein for use in the treatment of constipation or faecal impaction, or in the treatment of severe bacterial infections of the bowel. The invention also provides methods of treating constipation or faecal impaction, or in the treating severe bacterial infections of the bowel comprising administration of solutions as described herein.

As mentioned above, the solutions of the invention find use in cleansing the colon. The invention provides, in a further aspect, a solution in water of:

a) 300 to 800 mmol per litre ascorbate anion provided by a mixture of
 (i) ascorbic acid and
 (ii) one or more salts of ascorbic acid
the components (i) and (ii) being present in a molar ratio of from 1:4.5 to 1:7.0; and
b) optionally 10 to 200 g per litre polyethylene glycol, for use in cleansing the colon of a mammal The solution for use in cleansing the colon of a mammal preferably comprises ascorbate anion in a concentration of: 300-700 mmol per litre, for example 350-650 mmol per litre, for example 450-600 mmol per litre. As set out above, the ascorbate anion is provided by a mixture of ascorbic acid and one or more salts of ascorbic acid. Preferred forms of the ascorbate component are as set out above in section 3a).

In a preferred embodiment, PEG is present. Preferred forms of the PEG and preferred amounts thereof are as set out above in section 3a).

The solution for use in cleansing the colon of a mammal may additionally comprise one or more of:
 c) one or more electrolytes;
 d) one or more alkali metal or alkaline earth metal sulphates;
 e) one or more flavouring agents;
 f) one or more sweeteners.

For example, the solution for use in cleansing the colon of a mammal additionally comprises elements c), e) and f) from that list.

Preferred electrolytes and preferred amounts thereof are as set out above in section 3a).

Preferred alkali metal or alkaline earth metal sulphates and preferred amounts thereof are as set out above in section 3a).

Preferred flavouring agents and preferred amounts thereof are as set out above in section 3a).

Preferred sweeteners and preferred amounts thereof are as set out above in section 3a).

For example, the solution in water comprises:
a) 150 to 400 mmol ascorbate anion, provided by a mixture of
 (i) ascorbic acid and
 (ii) one or more salts of ascorbic acid
the components (i) and (ii) being present in a molar ratio of from 1:4.5 to 1:7.0; and
b) optionally 5 to 100 g PEG.

In particular, the invention provides a solution comprising:
a) 150 to 400 mmol ascorbate anion, provided by a mixture of
 (i) ascorbic acid and
 (ii) one or more salts of ascorbic acid
the components (i) and (ii) being present in a molar ratio of from 1:4.5 to 1:7.0;
b) 5 to 100 g PEG having an average molecular weight of 3000 to 4000 Da;
c) sodium chloride and potassium chloride;
d) optionally sodium sulphate;
e) optionally one or more flavouring agents; and
f) optionally one or more sweeteners
for use in cleansing the colon of a mammal Each of c) and d) may be as described above and/or be present in the amounts described above in section 3a). Each of e) and f) may be as described above and/or be in the amounts described above section 3a).

In particular, the invention provides a solution consisting essentially of:
a)
(i) 14 to 16 g per litre ascorbic acid and
(ii) 92 to 100 g per litre sodium ascorbate
b) 75 to 85 per litre PEG having an average molecular weight of 3000 to 4000 Da;
c) 6.0 to 6.8 g per litre sodium chloride and 2.0 to 2.8 g per litre potassium chloride;
e) one or more flavouring agents; and
f) one or more sweeteners,
for use in cleansing the colon of a mammal Each of c) and d) may be as described above and/or be present in the amounts described above in section 3a). Each of e) and f) may be as described above and/or be in the amounts described above section 3a).

For example, the invention provides a solution consisting essentially of:
a)
(i) 15.08 g per litre ascorbic acid and
(ii) 96.22 g per litre sodium ascorbate
b) 80 g per litre PEG having an average molecular weight of 3000 to 4000 Da;
c) 6.4 g per litre sodium chloride and 2.4 g per litre potassium chloride;
e) one or more flavouring agents; and
f) one or more sweeteners,
for use in cleansing the colon of a mammal For example, the flavouring and sweetener may be 1.20 g per litre orange flavour and 3.86 g per litre aspartame. For example, the flavouring and sweetener may be 3.20 g per litre citrus flavour and 1.75 g per litre aspartame. For example, the flavouring and sweetener may be 4.20 g per litre orange grapefruit flavour and 1.75 g per litre aspartame.

As mentioned above, a bowel cleansing treatment typically involves a subject taking a single dose or a split dose of cleansing solution. The volume of solution that a subject takes in a single dose treatment is described hereinabove. The subject may take some additional clear fluid after taking the solution as described hereinabove. The volume of solution that a subject takes in a split dose treatment is described hereinabove. The subject may take some additional clear fluid after each or either dose the solution as described hereinabove.

d) Compositions for Preparing Doses of Solutions

The invention further provides a composition (for example a dry composition, for example a powder) for the preparation of a solution of the invention. A composition can be in a quantity for the preparation of a dose of the solution, for example a 500 ml dose (for example a 16 or 17 US fluid ounce dose). The invention provides a composition for admixture with water, wherein the composition is optionally presented in two or more parts and comprises:
a) 150 to 400 mmol ascorbate anion provided by a mixture of:
(i) ascorbic acid and
(ii) one or more salts of ascorbic acid
the components (i) and (ii) being present in a molar ratio of from 1:4.5 to 1:7.0; and
b) 5 to 100 g polyethylene glycol.

For example, the components may be in dry powder, granular or other dry form. They may alternatively be in the form of concentrates or slurries. Components may be in the same or different physical forms. For example, the composition is a dry composition, for example a dry powder composition. For example, one or both of components a) and b) are dry powders. In a dry powder, it is possible for one or more components to be a salt hydrate.

As set out above in section 3a), the ascorbate anion is provided by a mixture of ascorbic acid and one or more salts of ascorbic acid. Preferred forms of the ascorbate component are as set out above in relation to solutions of the invention.

The composition of the invention preferably comprises ascorbate anion in an amount of 150 to 350 mmol, for example 175-325 mmol, for example 225-300 mmol.

Ascorbic acid has a molecular weight of 176 g/mol and sodium ascorbate has a molecular weight of 198 g/mol. Accordingly, the 150 to 400 mmol ascorbate anion can be provided by 3.3 to 12.8 g ascorbic acid and 24.3 to 69 g sodium ascorbate, for example 5.0 to 10 g ascorbic acid and 40 to 60 g sodium ascorbate; for example 6.0 to 10 g ascorbic acid and 40 to 60 g sodium ascorbate; for example 7.0 to 8.0 g ascorbic acid and 44 to 52 g sodium ascorbate; for example 7.0 to 8.0 g ascorbic acid and 46 to 50 g sodium ascorbate.

Potassium ascorbate has a molecular weight of 214 g/mol. Accordingly, the 150 to 400 mmol ascorbate anion can be provided by 3.3 to 12.8 g ascorbic acid and 26 to 75 g potassium ascorbate, for example 5.0 to 10 g ascorbic acid and 45 to 65 g potassium ascorbate; for example 7.0 to 8.0 g ascorbic acid and 47 to 56 g sodium ascorbate.

Magnesium ascorbate has a molecular weight of 374.5 g/mol and each mole of magnesium ascorbate provides two moles of ascorbate. Accordingly, the 150 to 400 mmol ascorbate anion can be provided by 3.3 to 12.8 g ascorbic acid and 23 to 65 g magnesium ascorbate, for example 5.0 to 10 g ascorbic acid and 38 to 57 g magnesium ascorbate; for example 7.0 to 8.0 g ascorbic acid and 42 to 49 g magnesium ascorbate.

In solid form, ascorbic acid is typically made up of protonated free ascorbic acid. In calculations of concentrations of "ascorbate anion" herein, the number of moles of "ascorbate anion" is taken as the total concentration of all ascorbate anion present, including the proportion that is protonated.

The weight of the ascorbate component may be 20 to 85 g, for example 25 to 75 g, for example 20 to 60 g, for example 50 to 60 g.

In an embodiment, the ascorbate component comprises (or consists essentially of) sodium ascorbate and ascorbic acid. For example, they may be present in a total amount and in a weight ratio as mentioned immediately above.

Preferred forms of the PEG are as set out above in section 3a), in relation to solutions of the invention. The composition comprises 5 to 100 g of PEG. Preferably, the composition comprises 10 to 80 g of PEG, more preferably 20 to 60 g, for example 30 to 50 g, for example 37.5 to 42.5 g, for example 40 g of PEG.

The composition may additionally comprise one or more of:
c) one or more electrolytes;
d) one or more alkali metal or alkaline earth metal sulphates;
e) one or more flavouring agents; and
f) one or more sweeteners.

Preferred electrolytes are as set out above in section 3a), in relation to solutions of the invention. For example, the composition may comprise sodium chloride in an amount of 0.5 to 5 g, for example 1.5 to 4 g, for example 2.0 to 3.5 g, for example 2.8 g or 3.2 g. For example, the composition may comprise potassium chloride in an amount of 0.5 to 5 g, for example 0.5 to 3.5 g, for example 0.75 to 2.5 g, for example 0.75 to 1.5 g, for example 1.0 to 1.4 g, for example 1.2 g or 1.3 g. In an embodiment, the composition is essentially free from sodium bicarbonate, for example essentially free from any bicarbonate.

Preferred alkali metal or alkaline earth metal sulphates are as set out above in section 3a), in relation to solutions of the invention. For example, the composition may comprise a sulphate component in an amount of 1 to 10 g, for example 2.5 to 7.5 g, for example 4 to 7.5 g, for example 5 to 7 g, for example 6 g. The one or more sulphate salts may be provided in any pharmaceutically acceptable form: they may each be anhydrous, or be in a hydrated form. The weights mentioned herein refer to the weight of the sulphate salt excluding any water of hydration. A hydrate form may be present in the dry powder composition, and that composition is still considered "dry" herein. In an alternative preferred embodiment, the composition does not comprise a sulphate component; that is to say that the composition is essentially free from alkali metal sulphates and alkaline earth metal sulphates; in particular essentially free from sodium sulphate, potassium sulphate and magnesium sulphate.

Preferred flavouring agents are as set out above in section 3a), in relation to solutions of the invention. For example the amount of flavouring agent may be 0.025 to 2.25 g, for example 0.025 to 1.0 g, for example 0.1 to 0.9 g, for example 0.5 to 0.9 g, for example 1.5 to 2.25 g, for example 0.15 g or 0.6 g, for example 1.6 or 2.1 g.

Preferred sweeteners are as set out above in section 3a), in relation to solutions of the invention. The amount of sweetener required depends on the nature and strength of the sweetener being considered. For example the amount of sweetener may be 0.05 to 2 g, for example 0.25 to 2 g, for example 1.25 to 2 g, for example 1.5 g, for example 1.93 g. Those quantities of aspartame are particularly suitable when used with orange flavouring, for example orange flavouring at 0.1 to 0.9 g, for example 0.5 to 0.9 g, for example 0.15 g, 0.4375 g or 0.6 g. For example, the sweetener may be aspartame at 0.5 to 1.25 g, for example 0.75 to 1.0 g, for example 0.875 g.

In particular, the invention provides a composition comprising:
  a) 150 to 400 mmol ascorbate anion provided by a mixture of:
    (i) ascorbic acid and
    (ii) one or more salts of ascorbic acid
  the components (i) and (ii) being present in a molar ratio of from 1:4.5 to 1:7.0;
  b) 5 to 100 g PEG having an average molecular weight of 3000 to 4000 Da.
  c) sodium chloride and potassium chloride;
  d) optionally sodium sulphate;
  e) optionally one or more flavouring agents;
  f) optionally one or more sweeteners.

Each of c) and d) may be present in the amounts described above. Each of e) and f) may be as described above and/or be in the amounts described above.

In one embodiment, the invention provides a composition comprising:
  a)
    (i) 6.0 to 10 g ascorbic acid and
    (ii) 40 to 60 g sodium ascorbate
    the components (i) and (ii) being present in a weight ratio of from 1:5063 to 1:7.875;
  b) 30 to 50 g PEG having an average molecular weight of 3000 to 4000 Da;
  c) 1.5 to 4 g sodium chloride and 0.5 to 3.5 g potassium chloride;
  e) one or more flavouring agents; and
  f) one or more sweeteners.

In one embodiment, the invention provides a composition comprising:
  a)
    (i) 7.43 g ascorbic acid and
    (ii) 48.11 g sodium ascorbate
  b) 40 g PEG having an average molecular weight of 3000 to 4000 Da;
  c) 3.20 g sodium chloride and 1.20 g potassium chloride;
  e) one or more flavouring agents; and
  f) one or more sweeteners.

For example, the flavouring and sweetener may be 0.60 g orange flavour and 1.93 g aspartame. For example, the flavouring and sweetener may be 1.60 g citrus flavour and 0.875 g aspartame. For example, the flavouring and sweetener may be 2.10 g orange grapefruit flavour and 0.875 g aspartame.

In an embodiment, the composition consists essentially of those components; that is to say that it does not contain any further components in significant quantities. The composition may, for example, not contain any sulphate.

One or more of components a) to f) may be presented in solid form, or in semi-solid form (for example in gel form).

In one embodiment, the one or more components of c), d) (when present), e) and f) are present in the composition for making up a solution. In an alternative presentation, some or all of components c), d) (when present), e) and f) may be provided separately from the composition for making up the solution, for example in a tablet or capsule. In an embodiment, there may be provided the ascorbate component and PEG, and optional flavouring and sweetener, in a form for admixture with water, and a tablet or capsule comprising the one or more electrolytes and/or the one or more alkali metal or alkaline earth metal sulphates, again with optional flavouring and sweetener. The flavouring and sweeteners need not be the same in the tablet or capsule as in the composition for admixture with water.

In some embodiments, it is desirable to package the ascorbate and the PEG components separately from each other.

In an embodiment, the composition can be provided to the subject with a plurality of flavouring agents (each optionally with one or more sweeteners), each separately packaged. The subject can then select a preferred flavouring (or flavouring and sweetener combination) according to his or her taste. The subject also has the choice of not using any flavouring or sweetener at all.

It will be apparent to the reader that all compounds and compositions described herein are of a nature and quality suitable for mammalian (especially human) consumption. For example, they are of pharmaceutical grade. The pharmaceutically acceptable compositions described herein may be provided in packaged form with instructions for use.

e) Compositions for Preparing Solutions

In a further aspect, the invention provides a composition comprising the following components in the following weight ratios:
  a) ascorbate anion 0.82 to 4.0 parts provided by a mixture of:
    (i) ascorbic acid and
    (ii) one or more salts of ascorbic acid
  the components (i) and (ii) being present in a molar ratio of from 1:4.5 to 1:7.0; and
  b) polyethylene glycol 1.0 part.

As mentioned above, for example, the components may be in dry powder, granular or other dry form. They may alternatively be in the form of concentrates or slurries. Components may be in the same or different physical forms. For example, the composition is a dry composition, for example a dry powder composition. For example, one or both of components a) and b) are dry powders.

As set out above, the ascorbate anion is provided by a mixture of ascorbic acid and one or more salts of ascorbic acid. Preferred forms of the ascorbate component are as set out above in section 3a) in relation to solutions of the invention.

Preferred forms of the PEG are as set out above in section 3a) in relation to solutions of the invention. The composition of the invention preferably comprises ascorbate anion in a weight ratio to PEG of 0.82 to 3.0:1. More preferably, the weight ratio is 0.9 to 2.0:1, for example 1.0 to 1.5:1, for example 1.2 to 1.3:1. As set out above, the ascorbate anion is provided by ascorbic acid and a salt of ascorbic acid in a ratio of 1:4.5 to 1:7.0. The molar ratio of the ascorbic acid and the one or more salts of ascorbic acid is from 1:4.75 to 1:6.75; more preferably from 1:5.0 to 1:6.0; for example from 1:5.40 to 1:5.80; for example 15:85. The salt of ascorbic acid can be sodium ascorbate. A mixture of ascorbic acid and sodium ascorbate in a molar ratio of from 1:4.5 to 1:7.0 has ascorbic acid and sodium ascorbate present in a weight ratio of 1:5.063 to 1:7.875. A more preferred ratio is 1:5.344 to 1:7.594; more preferably from 1:5.625 to 1:6.75; for example from 1:6.075 to 1:6.525, for example 1:6.38.

In a composition in which the weight ratio of ascorbate anion to PEG is 0.82 to 3.0:1, and in which the ascorbate anion is provided by ascorbic acid and a sodium ascorbate in a molar ratio of 1:4.5 to 1:7.0, the weight ratio of ascorbic acid:sodium ascorbate:PEG is 0.1031 to 0.5486:0.7591-2.970:1. For example, the weight ratio can be 0.12 to 0.30:0.9 to 1.9:1; more preferably 0.15 to 0.25:1.0 to 1.5:1; for example 0.185 to 0.190:1.15 to 1.25:1; for example 0.1885:1.203:1.

The composition may additionally comprise one or more of:
c) one or more electrolytes;
d) one or more alkali metal or alkaline earth metal sulphates;
e) one or more flavouring agents;
f) one or more sweeteners.

Preferred electrolytes are as set out above in section 3a) in relation to solutions of the invention. For example, the composition may comprise sodium chloride in a weight ratio to PEG of 0.005 to 0.5:1, for example 0.01 to 0.3:1, for example 0.03 to 0.2:1, for example 0.04 to 0.15:1, for example 0.05 to 0.1:1, for example 0.06 to 0.09:1. For example, the composition may comprise potassium chloride in a weight ratio to PEG of 0.005 to 0.30:1, for example 0.01 to 0.20:1, for example 0.01 to 0.10:1, for example 0.02 to 0.04:1.

For example, the invention provides a composition comprising the following components in the following weight ratios:
a) ascorbate anion: 0.82 to 4.0 parts;
b) polyethylene glycol: 1.0 part;
c1) sodium chloride: 0.005 to 1.0 parts; and
c2) potassium chloride: 0.005 to 1.0 parts;
the ascorbate anion being provided by
(i) ascorbic acid and
(ii) one or more salts of ascorbic acid
the components (i) and (ii) being present in a molar ratio of from 1:4.5 to 1:7.0.

The composition is preferably essentially free from sodium bicarbonate. For example, it is essentially free from any bicarbonate.

Preferred alkali metal or alkaline earth metal sulphates are as set out above in section 3a) in relation to solutions of the invention. For example, the composition may comprise a sulphate component (for example sodium sulphate) in a weight ratio to PEG of 0.01 to 0.50:1, For example, the composition may comprise a sulphate component (for example sodium sulphate) in a weight ratio to PEG of 0.02 to 0.25:1, for example 0.03 to 0.22:1, for example 0.05 to 0.20:1, for example 0.10 to 0.20:1.

In an embodiment, the composition does not comprise a sulphate component; that is to say that the composition is essentially free from alkali metal sulphates and alkaline earth metal sulphates; in particular essentially free from sodium sulphate, potassium sulphate and magnesium sulphate.

Preferred flavouring agents are as set out above in section 3a) in relation to solutions of the invention. For example the composition may comprise a flavouring agent in a weight ratio to PEG of 0.0005 to 0.050:1, for example 0.001 to 0.025:1, for example 0.0025 to 0.020:1.

Preferred sweeteners are as set out above in section 3a) in relation to solutions of the invention. For example the composition may comprise a sweetener in a weight ratio to PEG of 0.0005 to 0.1:1, for example 0.001 to 0.075:1, for example 0.002 to 0.050:1.

In particular, the invention provides a composition comprising the following components in the following weight ratios:
a) ascorbate anion: 0.82 to 4.0 parts
b) PEG having an average molecular weight of 3000 to 4000 Da: 1.0 part.
c) sodium chloride and potassium chloride;
d) optionally sodium sulphate;
e) optionally one or more flavouring agents; and
f) optionally one or more sweeteners;
the ascorbate anion being provided by
(i) ascorbic acid and
(ii) one or more salts of ascorbic acid
the components (i) and (ii) being present in a molar ratio of from 1:4.5 to 1:7.0.

Each of c) and d) may be present in the weight ratios to PEG described above. Each of e) and f) may be as described above and/or be in the weight ratios to PEG described above.

In one embodiment, the invention provides a composition comprising the following components in the following weight ratios:
a)
(i) ascorbic acid: 0.12 to 0.30 parts; and
(ii) sodium ascorbate: 0.9 to 1.9 parts
the components (i) and (ii) being present in a weight ratio of from 1:5063 to 1:7.875;
b) PEG having an average molecular weight of 3000 to 4000 Da: 1 part
c) sodium chloride 0.05 to 0.10 parts and litre potassium chloride 0.02 to 0.04 parts;
e) one or more flavouring agents: 0.001 to 0.075 parts; and
f) one or more sweeteners: 0.002 to 0.050 parts.

For example, the composition may comprise the following components in the following weight ratios:
a)
(i) ascorbic acid: 0.189 parts; and
(ii) sodium ascorbate: 1.20 parts
b) PEG having an average molecular weight of 3000 to 4000 Da: 1 part c) sodium chloride 0.08 parts and litre potassium chloride 0.03 parts;
e) one or more flavouring agents: 0.001 to 0.075 parts; and
f) one or more sweeteners: 0.002 to 0.050 parts.

For example, the flavouring and sweetener may be 0.015 parts orange flavour and 0.048 parts aspartame. For example, the flavouring and sweetener may be 0.040 parts citrus flavour and 0.022 parts aspartame. For example, the flavouring and sweetener may be 0.053 parts orange grapefruit flavour and 0.022 parts aspartame.

In an embodiment, the composition consists essentially of those components; that is to say that it does not contain any further components in significant quantities. The composition may, for example, not contain any sulphate.

Preferred compositions of the invention are dry compositions, for example dry powder compositions.

In a further aspect, the invention provides a composition comprising the following components in the following weight ratios:
(i) ascorbic acid: 1 part and
(ii) one or more salts of ascorbic acid: 5.063 to 7.875 parts The salt of ascorbic acid can be sodium ascorbate. A mixture of ascorbic acid and sodium ascorbate in a molar ratio of from 1:4.5 to 1:7.0 has ascorbic acid and sodium ascorbate present in a weight ratio of 1:5.063 to 1:7.875. A more preferred ratio is 1:5.344 to 1:7.594; more preferably from 1:5.625 to 1:6.75; for example from 1:6.075 to 1:6.525, for example 1:6.38.

f) Methods of Preparing Solutions and Compositions

The invention further provides a method of preparing a solution of the invention comprising combining the components of the solution with water. The method comprises the step of combining the components with water and admixing. Some or all of the components may be in physical association with each other before the water is added. In some embodiments, the components of the composition are provided in more than one part; that is to say that they are packaged separately. All of the components may be combined with each other before combining with water. For example, if flavouring agent and sweetener are packaged separately from other components, they may be combined with the other components before combining with water. One or some of the components may be combined with water and admixed in a first step and then some or all of the remaining components may be added in a second step. For example, the components may be in dry form, for example in powder form.

As set out above in section 3d), the invention provides a composition (for example a dry composition, for example a powder) for the preparation of a solution of the invention. The invention further provides a method of preparing a composition of the invention comprising combining the components of the composition. For example, the method may be a method of preparing a composition of the invention in powder form. As set out in section 3d) above, the components for the preparation of a solution of the invention may be presented in two or more parts. The invention thus further provides a method of preparing a composition of the invention comprising combining some, but not all of the components of the composition. The invention thus provides a method comprising blending a mixture of:
(i) ascorbic acid: 1 part and
(ii) one or more salts of ascorbic acid: 5.063 to 7.875 parts The salt of ascorbic acid can be sodium ascorbate. A mixture of ascorbic acid and sodium ascorbate in a molar ratio of from 1:4.5 to 1:7.0 has ascorbic acid and sodium ascorbate present in a weight ratio of 1:5.063 to 1:7.875. A more preferred ratio is 1:5.344 to 1:7.594; more preferably from 1:5.625 to 1:6.75; for example from 1:6.075 to 1:6.525, for example 1:6.38.

The method may comprise blending a mixture of:
(i) ascorbic acid and
(ii) one or more salts of ascorbic acid
the components (i) and (ii) being present in a molar ratio of from 1:4.5 to 1:7.0.

Preferred salts of ascorbic acid are as set out above in section 3a). Preferred ratios of components (i) and (ii) are as set out above in section 3a).

The method may further comprise blending a mixture of:
a) ascorbate anion: 0.82 to 4.0 parts;
b) polyethylene glycol: 1.0 part;
c1) sodium chloride: 0.005 to 1.0 parts; and
c2) potassium chloride: 0.005 to 1.0 parts;
the ascorbate anion being provided by
(i) ascorbic acid and
(ii) one or more salts of ascorbic acid
the components (i) and (ii) being present in a molar ratio of from 1:4.5 to 1:7.0.

The components may be weighed out and added together before blending, or the components may be added into a blend mixture in any desired order.

Blending of the compositions in bulk may, for example, be carried out on a 100 Kg, 500 Kg or 1000 Kg scale. After blending, the composition is divided into smaller portions for packaging into dosage amounts. The invention thus provides a method comprising the step of dividing bulk composition as set out in section 3e) above into smaller portions. The invention also provides a method comprising the step of filling containers with individual dosage amounts of bulk composition as set out in section 3e). The invention thus provides a method comprising the step of filling a container with a composition as set out in section 3d). The composition as set out in section 3d) may be presented in two or more parts. The method may thus comprise the step of filling a container with some but not all of the components of a composition as set out in section 3d).

4. ALTERNATIVE SOLUTIONS

The invention also provides a colon cleansing solution does not contain any ascorbic acid. The invention thus provides, in a second aspect, a colon cleansing solution comprising:
a) 360 to 440 mmol per litre ascorbate anion provided by one or more salts of ascorbic acid
b) 10 to 200 g per litre polyethylene glycol;
the solution being essentially free from ascorbic acid.

The solution of the invention has advantageous properties. The solution of the invention has a surprisingly palatable taste and it is highly effective as a colon cleansing solution with a good tolerability profile.

5. DETAILED DESCRIPTION a) Contents of Solutions

The solutions of the invention are aqueous solutions. Suitable salts of ascorbic acid include alkali metal salts and alkaline earth metal salts. For example a salt may be selected from sodium, potassium, magnesium and calcium salts. For example, preferred salts of ascorbic acid include sodium ascorbate, potassium ascorbate, magnesium ascorbate and calcium ascorbate. Particularly preferred salts of ascorbic acid are magnesium ascorbate and sodium ascorbate, for example sodium ascorbate. In one embodiment, the solution comprises sodium ascorbate and no further ascorbate.

The solution of the invention preferably comprises ascorbate anion in a concentration of: 370-430 mmol per litre, for example 380-420 mmol per litre, for example 400-410 mmol per litre.

A solution of the invention may comprise 72 to 88 g/litre of ascorbate salt. For example, a solution of the invention comprises 75 to 85 g/litre, for example 78 to 82 g/litre, for example 80 g/litre.

Sodium ascorbate has a molecular weight of 198 g/mol. Accordingly, a solution of the invention may comprise sodium ascorbate at 71.3-87.1 g per litre, for example 73.3-85.1 g per litre for example 75.2-83.2 g per litre, for example 79.2-80.2 g per litre.

Potassium ascorbate has a molecular weight of 214 g/mol. Accordingly, a solution of the invention may comprise potassium ascorbate at 77.0-94.2 g per litre, 79.2-92.0 g per litre, for example 81.3-89.9 g per litre, for example 85.6-86.7 g per litre.

Magnesium ascorbate has a molecular weight of 374.5 g/mol and each mole of magnesium ascorbate provides two moles of ascorbate. Accordingly, a solution of the invention may comprise magnesium ascorbate at 67.4-82.4 g per litre, for example 69.3-80.5 g per litre, for example 71.2-78.6 g per litre, for example 74.9-75.8 g per litre.

Depending on the pH of the solution, some ascorbate anion may be protonated and thus exist as free ascorbic acid in solution. At the pH of solutions that would typically be administered, only a minor proportion of ascorbate is protonated. In calculations of concentrations of "ascorbate anion" herein, the concentration of "ascorbate anion" is taken as the total concentration of all ascorbate anion present, including the proportion that is protonated.

The cleansing solution comprises polyethylene glycol. The polyethylene glycol (PEG) may be as described above in section 3a). The cleansing solution comprises 10 to 200 g per litre of PEG. Preferably, the solution comprises 20 to 160 g per litre of PEG, more preferably 40 to 120 g per litre, for example 60 to 100 g per litre, for example 75 to 85 g per litre, for example 80 g per litre.

The cleansing solution may additionally comprise one or more of:
c) one or more electrolytes;
d) one or more alkali metal or alkaline earth metal sulphates;
e) one or more flavouring agents;
f) one or more sweeteners.

The cleansing solution may comprise one or more electrolytes. Electrolytes include salts of sodium, potassium, calcium and magnesium, particularly sodium and potassium; and salts of chloride, iodide, bicarbonate and carbonate, particularly chloride. Preferred electrolytes are sodium chloride and potassium chloride. In an embodiment, the solution is essentially free from sodium bicarbonate, for example essentially free from any bicarbonate.

For example, the solution may comprise sodium chloride at a concentration of 1 to 10 g per litre. For example, sodium chloride may be present at a concentration of 3 to 8 g per litre, for example 4 to 7 g per litre; for example 4.5 to 5.5 g per litre; for example 5.0 g per litre or 5.6 g per litre.

For example, the solution may comprise potassium chloride at a concentration of 1 to 10 g per litre. For example, potassium chloride may be present at a concentration of 1 to 7 g per litre, for example 1.5 to 5 g per litre, for example 1.5 to 3 g per litre, for example 1.7 to 2.8 g per litre; for example 1.8 g per litre or 2.6 g per litre.

In an embodiment, the solution comprises sodium chloride and potassium chloride. They can be present in the amounts mentioned immediately above. For example, sodium chloride may be present at a concentration of 4 to 7 g per litre and potassium chloride may be present at a concentration of 1.5 to 3 g per litre.

The cleansing solution may comprise one or more alkali metal sulphates, alkaline earth metal sulphates or a mixture thereof (herein referred to as a "sulphate component"). The sulphate component and the quantity thereof may be as described above in section 3a).

In an alternative preferred embodiment, the solution does not comprise a sulphate component; that is to say that the solution is essentially free from alkali metal sulphates and alkaline earth metal sulphates; in particular essentially free from sodium sulphate, potassium sulphate and magnesium sulphate.

In the solutions of the invention described herein, the quantities of the individual components recited do not include any solutes that may be present in the water used to prepare the solutions, for example, in hard water areas there may be significant amounts of $Ca^{2+}$ and $Mg^{2+}$ carbonates, bicarbonates or sulphates present in tap water.

The cleansing solution preferably includes a flavouring agent. The flavouring may be as described above in section 3a). Lemon/lime flavour and orange flavour are particularly preferred.

The amount of flavouring required depends on the nature and strength of the flavouring in question. Typically, it is 0.05 to 4.5 g per litre, for example 0.05 to 2.0 g per litre, for example 0.5 to 1.8 g per litre, for example 2.5 to 4.5 g per litre, for example 0.6 g per litre or 1.6 g per litre, for example 3.2 or 4.3 g per litre.

The cleansing solution preferably includes a sweetener. The sweetener may be as described above in section 3a).

Alternatively, compositions of the invention can be essentially free from added sweeteners, for example to minimize the number of different components in the compositions.

A souring agent (for example citric acid) may be present as a taste enhancer. A souring agent is a component that imparts a sourness to a composition. Other souring agents include malic acid, acetic acid, tartaric acid, gluconodeltalactone, phosphoric acid, succinic acid, phytic acid, lactic acid or salts thereof. The souring agent (for example citric acid) may be provided in an encapsulated form. The encapsulation provides a coating that isolates the souring agent from other components and from air and moisture prior to its use. Several encapsulated forms of citric acid, or other souring agents, are commercially available. For example, the encapsulation may be with a water-soluble coating.

The amount of sweetener required depends on the nature and strength of the sweetener being considered. Typically, it is 0.10 to 4 g per litre. For example, the sweetener may be aspartame at 0.5 to 4 g per litre, for example 2.5 to 4.0 g per litre, for example 2.0 g per litre, for example 2.2 g per litre or 3.25 g per litre. Those quantities of aspartame are particularly suitable when used with orange flavouring, for example orange flavouring at 0.2 to 1.8 g per litre, for example 0.5 to 1.8 g per litre, for example 0.6 g per litre or 1.6 g per litre or 3.25 g per litre.

The invention thus provides a colon cleansing solution comprising:
a) 360 to 440 mmol per litre ascorbate anion provided by one or more salts of ascorbic acid;
b) 10 to 200 g per litre PEG;
c) one or more electrolytes;

d) optionally one or more alkali metal or alkaline earth metal sulphates;
e) optionally one or more flavouring agents; and
f) optionally one or more sweeteners;
the solution being essentially free from ascorbic acid.

In particular, the invention provides a colon cleansing solution comprising:
a) 360 to 440 mmol per litre ascorbate anion provided by one or more salts of ascorbic acid;
b) 10 to 200 g per litre PEG having an average molecular weight of 3000 to 4000 Da;
c) sodium chloride and potassium chloride;
d) optionally sodium sulphate;
e) optionally one or more flavouring agents; and
f) optionally one or more sweeteners;
the solution being essentially free from ascorbic acid.

Each of c) and d) may be present in the concentrations described above. Each of e) and f) may be as described above and/or be in the concentrations described above.

In particular, the invention provides a colon cleansing solution comprising:
a) 360 to 440 mmol per litre ascorbate anion provided by one or more salts of ascorbic acid;
b) 10 to 200 g per litre PEG having an average molecular weight of 3000 to 4000 Da;
c) sodium chloride and potassium chloride;
e) one or more flavouring agents; and
f) one or more sweeteners;
the solution being essentially free from ascorbic acid.

In one embodiment, the one or more components of c), d) (when present), e) and f) are present in the solution. In an alternative presentation, some or all of components c), d) (when present), e) and f) may be provided separately from the solution, for example in a tablet or capsule. In an embodiment, the solution may comprise a) the ascorbate component and b) PEG, and optional flavouring and sweetener (e) and f)), and a tablet or capsule may comprise c) the one or more electrolytes and/or d) the one or more alkali metal or alkaline earth metal sulphates, again with optional flavouring and sweetener (e) and f)). The flavouring and sweeteners need not be the same in the tablet or capsule as in the solution.

In one embodiment, the invention provides a colon cleansing solution comprising:
a) 71.3 to 87.1 g per litre sodium ascorbate
b) 60 to 100 g per litre PEG having an average molecular weight of 3000 to 4000 Da;
c) 3 to 8 g per litre sodium chloride and 1 to 7 g per litre potassium chloride;
e) one or more flavouring agents; and
f) one or more sweeteners.

In an embodiment, the solution consists essentially of those components; that is to say that it does not contain any further components in significant quantities. The solution may, for example, not contain any sulphate.

In particular, the invention provides a solution consisting essentially of:
a) 75 to 85 g per litre sodium ascorbate
b) 75 to 85 per litre PEG having an average molecular weight of 3000 to 4000 Da;
c) 4.5 to 5.5 g per litre sodium chloride and 1.5 to 2.3 g per litre potassium chloride;
e) one or more flavouring agents; and
f) one or more sweeteners.

For example, the invention provides a colon cleansing solution consisting essentially of:
a) 80 g per litre sodium ascorbate
b) 80 g per litre PEG having an average molecular weight of 3000 to 4000 Da;
c) 5.0 g per litre sodium chloride and 1.80 g per litre potassium chloride;
e) one or more flavouring agents; and
f) one or more sweeteners.

For example, the flavouring and sweetener may be 1.60 g per litre orange flavour and 2.20 g per litre aspartame. For example, the flavouring and sweetener may be 3.20 g per litre lemon/lime flavour and 3.25 g per litre aspartame. For example, the flavouring and sweetener may be 4.30 g per litre orange grapefruit flavour and 3.25 g per litre aspartame.

Preferably, the colon cleansing solution is hyper-osmotic. That is to say that it has a higher osmotic strength than blood in the human body. It may, for example have a measured osmolality in the range 500 to 2000 mOsmol/kg. For example, the osmolality may be in the range 700 to 1800 mOsmol/kg. For example, the solutes in 500 ml of the solution may have a measured V(350) value of from 1000 to 2000 ml, for example from 1300 to 1700 ml, for example from 1400 to 1600 ml, and be in a volume of 400 to 600 ml, for example 500 ml.

The invention provides a colon cleansing solution comprising:
a) 360 to 440 mmol per litre ascorbate anion provided by one or more salts of ascorbic acid
b) 10 to 200 g per litre polyethylene glycol;
the solution being essentially free from ascorbic acid, and 500 ml of the solution having a V(350) osmolality value of from 1000 to 2000 ml.

For example, 500 ml of the solution may have a V(350) osmolality value of from 1200 to 1800 ml, for example from 1400 to 1600 ml.

b) Additional Optional Contents of Solutions

The solutions of the invention may include additional optional components as set out above in section 3b).

c) Uses of Solutions of the Invention

Uses of solutions of the invention are as set out above in section 3c). The invention thus provides, in a further aspect a solution in water of:
a) 360 to 440 mmol per litre ascorbate anion provided by one or more salts of ascorbic acid; and
b) optionally 10 to 200 g per litre polyethylene glycol,
the solution being essentially free from ascorbic acid,
for use in cleansing the colon of a mammal The solution for use in cleansing the colon of a mammal preferably comprises ascorbate anion in a concentration of: 370-430 mmol per litre, for example 380-420 mmol per litre, for example 400-410 mmol per litre. As set out above, the ascorbate anion is provided by one or more salts of ascorbic acid. Preferred forms of the ascorbate component are as set out above in section 5a).

In a preferred embodiment, PEG is present. Preferred forms of the PEG and preferred amounts thereof are as set out above in section 5a).

The solution for use in cleansing the colon of a mammal may additionally comprise one or more of:
c) one or more electrolytes;
d) one or more alkali metal or alkaline earth metal sulphates;
e) one or more flavouring agents;
f) one or more sweeteners.

For example, the solution for use in cleansing the colon of a mammal additionally comprises elements c), e) and f) from that list.

Preferred electrolytes and preferred amounts thereof are as set out above in section 5a).

Preferred alkali metal or alkaline earth metal sulphates and preferred amounts thereof are as set out above in section 5a).

Preferred flavouring agents and preferred amounts thereof are as set out above in section 5a).

Preferred sweeteners and preferred amounts thereof are as set out above in section 5a).

For example, the solution in water comprises:
- a) 180 to 220 mmol ascorbate anion provided by one or more salts of ascorbic acid; and
- b) optionally 5 to 100 g PEG.

the solution being essentially free from ascorbic acid.

In particular, the invention provides a solution comprising:
- a) 180 to 220 mmol ascorbate anion provided by one or more salts of ascorbic acid;
- b) 5 to 100 g PEG having an average molecular weight of 3000 to 4000 Da;
- c) sodium chloride and potassium chloride;
- d) optionally sodium sulphate;
- e) optionally one or more flavouring agents; and
- f) optionally one or more sweeteners, the solution being essentially free from ascorbic acid for use in cleansing the colon of a mammal Each of c) and d) may be as described above and/or be present in the amounts described above in relation to solutions of the invention. Each of e) and f) may be as described above and/or be in the amounts described above in section 5a).

In particular, the invention provides a solution consisting essentially of:
- a) 75 to 85 g per litre sodium ascorbate
- b) 75 to 85 per litre PEG having an average molecular weight of 3000 to 4000 Da;
- c) 4.5 to 5.5 g per litre sodium chloride and 1.5 to 2.3 g per litre potassium chloride;
- e) one or more flavouring agents; and
- f) one or more sweeteners, for use in cleansing the colon of a mammal For example, the invention provides a solution consisting essentially of:
- a) 80 g per litre sodium ascorbate
- b) 80 g per litre PEG having an average molecular weight of 3000 to 4000 Da;
- c) 5.0 g per litre sodium chloride and 1.80 g per litre potassium chloride;
- e) one or more flavouring agents; and
- f) one or more sweeteners.

for use in cleansing the colon of a mammal

For example, the flavouring and sweetener may be 1.60 g per litre orange flavour and 2.20 g per litre aspartame. For example, the flavouring and sweetener may be 3.20 g per litre lemon/lime flavour and 3.25 g per litre aspartame. For example, the flavouring and sweetener may be 4.30 g per litre orange grapefruit flavour and 3.25 g per litre aspartame.

As mentioned above, a bowel cleansing treatment typically involves a subject taking a single dose or a split dose of cleansing solution. The volume of solution that a subject takes in a single dose treatment is described hereinabove in section 3c). The subject may take some additional clear fluid after taking the solution as described hereinabove.

The volume of solution that a subject takes in a split dose treatment is described hereinabove in section 3c). The subject may take some additional clear fluid after each or either dose the solution as described hereinabove.

d) Compositions for Preparing Doses of Solutions

The invention further provides a composition (for example a dry composition, for example a powder) for the preparation of a solution of the invention. A composition can be provided in a quantity for the preparation of a dose of the solution, for example a 500 ml dose. The invention provides a composition for admixture with water, wherein the composition is optionally presented in two or more parts and comprises:
- a) 180 to 220 mmol ascorbate anion provided by one or more salts of ascorbic acid; and
- b) 5 to 100 g polyethylene glycol;

the solution being essentially free from ascorbic acid.

For example, the components may be in dry powder, granular or other dry form. They may alternatively be in the form of concentrates or slurries. Components may be in the same or different physical forms. For example, the composition is a dry composition, for example a dry powder composition. For example, one or both of components a) and b) are dry powders.

As set out above in section 5a), the ascorbate anion may be provided by one or more salts of ascorbic acid. Preferred forms of the ascorbate component are as set out above in relation to solutions of the invention.

The composition of the invention preferably comprises ascorbate anion in an amount of: 185 to 215 mmol, for example 190 to 210 mmol, for example 200-205 mmol Sodium ascorbate has a molecular weight of 198 g/mol. Accordingly, the 180 to 220 mmol ascorbate anion can be provided by 35.6 to 43.6 g sodium ascorbate. For example, the sodium ascorbate may be present at a level of 36.6 to 42.6 g, for example 37.6 to 41.6 g, for example 39.6 to 40.6 g.

Potassium ascorbate has a molecular weight of 214 g/mol. Accordingly, the 180 to 220 mmol ascorbate anion can be provided by 38.5 to 47.1 g potassium ascorbate. For example, the potassium ascorbate may be present at a level of 39.6 to 46.0 g, for example 40.7 to 44.9 g, for example 42.8 to 43.9 g.

Magnesium ascorbate has a molecular weight of 374.5 g/mol and each mole of magnesium ascorbate provides two moles of ascorbate. Accordingly, the 180 to 220 mmol ascorbate anion can be provided by 33.7 to 41.2 g magnesium ascorbate. For example, the magnesium ascorbate may be present at a level of 34.6 to 40.3 g, for example 35.6 to 39.3 g, for example 37.5 to 38.4 g.

The weight of the ascorbate salt component may be 33 to 47 g, for example 35 to 45 g, for example 37 to 43 g.

In an embodiment, the ascorbate component consists essentially of sodium ascorbate alone. For example, it may be present in an amount as mentioned immediately above.

Preferred forms of the PEG are as set out in section 5a) above in relation to solutions of the invention. The composition comprises 5 to 100 g of PEG. Preferably, the composition comprises 10 to 80 g of PEG, more preferably 20 to 60 g, for example 30 to 50 g, for example 37.5 to 42.5 g, for example 40 g of PEG.

The composition may additionally comprise one or more of:
- c) one or more electrolytes;
- d) one or more alkali metal or alkaline earth metal sulphates;

e) one or more flavouring agents; and
f) one or more sweeteners.

Preferred electrolytes are as set out above in section 5a) in relation to solutions of the invention. For example, the composition may comprise sodium chloride in an amount of 0.5 to 5 g, for example 1.5 to 4 g, for example 2.0 to 3.5 g, for example 2.5 or 2.8 g. For example, the composition may comprise potassium chloride in an amount of 0.5 to 5 g, for example 0.5 to 3.5 g, for example 0.75 to 2.5 g, for example 0.75 to 1.5 g, for example 0.85 to 1.4 g, for example 0.9 or 1.3 g. In an embodiment, the composition is essentially free from sodium bicarbonate, for example essentially free from any bicarbonate.

Preferred alkali metal or alkaline earth metal sulphates are as set out above in relation to solutions of the invention. For example, the composition may comprise a sulphate component in an amount of 1 to 10 g, for example 2.5 to 7.5 g, for example 4 to 7.5 g, for example 5 to 7 g, for example 6 g. The one or more sulphate salts may be provided in any pharmaceutically acceptable form: they may each be anhydrous, or be in a hydrated form. The weights mentioned herein refer to the weight of the sulphate salt excluding any water of hydration. A hydrate form may be present in the dry powder composition, and that composition is still considered "dry" herein. In an alternative preferred embodiment, the composition does not comprise a sulphate component; that is to say that the solution is essentially free from alkali metal sulphates and alkaline earth metal sulphates; in particular essentially free from sodium sulphate, potassium sulphate and magnesium sulphate.

Preferred flavouring agents are as set out above in section 5a) in relation to solutions of the invention. For example the amount of flavouring agent may be 0.025 to 2.25 g, for example 0.025 to 1.0 g, for example 0.25 to 0.9 g, for example 1.25 to 2.25 g, for example 0.3 g or 0.8 g, for example 1.6 or 2.15 g.

Preferred sweeteners are as set out above in relation to solutions of the invention. For example the amount of sweetener may be 0.05 to 2 g. For example, the sweetener may be aspartame at 0.25 to 2 g, for example at 1.25 to 2.0 g, for example 1.0, 1.1 g or 1.625 g. Those quantities of aspartame are particularly suitable when used with orange flavouring, for example orange flavouring at 0.1 to 0.9 g, for example 0.25 to 0.9 g, for example 0.3, 0.8 g or 1.625 g.

In particular, the invention provides a composition comprising:
a) 180 to 220 mmol ascorbate anion provided by one or more salts of ascorbic acid;
b) 5 to 100 g PEG having an average molecular weight of 3000 to 4000 Da.
c) sodium chloride and potassium chloride;
d) optionally sodium sulphate;
e) optionally one or more flavouring agents;
f) optionally one or more sweeteners;
the solution being essentially free from ascorbic acid.

Each of c) and d) may be present in the amounts described above. Each of e) and f) may be as described above and/or be in the amounts described above.

In one embodiment, the invention provides composition comprising:
a) 35.65 to 43.55 g sodium ascorbate
b) 30 to 50 g PEG having an average molecular weight of 3000 to 4000 Da;
c) 1.5 to 4 g sodium chloride and 0.5 to 3.5 g potassium chloride;
e) one or more flavouring agents; and
f) one or more sweeteners.

In one embodiment, the invention provides a composition comprising:
a) 40 g sodium ascorbate
b) 40 g PEG having an average molecular weight of 3000 to 4000 Da;
c) 2.50 g sodium chloride and 0.90 g potassium chloride;
e) one or more flavouring agents; and
f) one or more sweeteners.

For example, the flavouring and sweetener may be 0.80 g orange flavour and 1.10 g aspartame. For example, the flavouring and sweetener may be 1.60 g lemon/lime flavour and 1.625 g aspartame. For example, the flavouring and sweetener may be 2.15 g orange grapefruit flavour and 1.625 g aspartame.

In an embodiment, the composition consists essentially of those components; that is to say that it does not contain any further components in significant quantities. The composition may, for example, not contain any sulphate.

One or more components a) to f) may be presented in solid form, or in semi-solid form (for example in gel form).

In one embodiment, the one or more components of c), d) e) and f) are present in the composition for making up a solution. In an alternative presentation, some or all of components c), d) e) and f) may be provided separately from the composition for making up the solution, for example in a tablet or capsule. In an embodiment, there may be provided the ascorbate component and PEG, and optional flavouring and sweetener, in a form for admixture with water, and a tablet or capsule comprising the one or more electrolytes and/or the one or more alkali metal or alkaline earth metal sulphates, again with optional flavouring and sweetener. The flavouring and sweeteners need not be the same in the tablet or capsule as in the composition for admixture with water.

In some embodiments, it is desirable to package the ascorbate and the PEG components separately from each other.

In an embodiment, the composition can be provided to the subject with a plurality of flavouring agents (each optionally with one or more sweeteners), each separately packaged. The subject can then select a preferred flavouring (or flavouring and sweetener combination) according to his or her taste. The subject also has the choice of not using any flavouring or sweetener at all.

It will be apparent to the reader that all compounds and compositions described herein are of a nature and quality suitable for mammalian (especially human) consumption. For example, they are of pharmaceutical grade. The pharmaceutically acceptable compositions described herein may be provided in packaged form with instructions for use.

e) Compositions for Preparing Solutions

In a further aspect, the invention provides a composition comprising the following components in the following weight ratios:
a) ascorbate anion 0.78 to 1.2 parts; and
b) polyethylene glycol 1.0 part;
the ascorbate anion being provided by one or more salts of ascorbic acid;
the composition being essentially free from ascorbic acid.

As mentioned above, for example, the components may be in dry powder, granular or other dry form. They may alternatively be in the form of concentrates or slurries. Components may be in the same or different physical forms. For example, the composition is a dry composition, for example a dry powder composition. For example, one or both of components a) and b) are dry powders.

As set out above, the ascorbate anion is provided by one or more salts of ascorbic acid. Preferred forms of the ascorbate component are as set out above in section 5a) in relation to solutions of the invention. Preferred salts are sodium, potassium and magnesium ascorbate, especially sodium ascorbate.

Preferred forms of the PEG are as set out above in section 5a) in relation to solutions of the invention. The composition of the invention preferably comprises ascorbate anion in a weight ratio to PEG of 0.80 to 1.0:1. More preferably, the weight ratio is 0.85 to 0.95:1, for example 0.86 to 0.90:1, for example 0.88:1.

The preferred ascorbate salt is sodium ascorbate. The composition of the invention preferably comprises sodium ascorbate and PEG in a weight ratio of 0.90 to 1.125:1. More preferably, the weight ratio is 0.956 to 1.069:1, for example 0.968 to 1.013:1, for example 0.99:1, for example 1:1.

The composition may additionally comprise one or more of:
c) one or more electrolytes;
d) one or more alkali metal or alkaline earth metal sulphates;
e) one or more flavouring agents;
f) one or more sweeteners.

Preferred electrolytes are as set out above in section 5a) in relation to solutions of the invention. For example, the composition may comprise sodium chloride in a weight ratio to PEG of 0.005 to 0.5:1, for example 0.01 to 0.3:1, for example 0.02 to 0.2:1, for example 0.03 to 0.15:1, for example 0.04 to 0.1:1, for example 0.05 to 0.08:1. For example, the composition may comprise potassium chloride in a weight ratio to PEG of 0.005 to 0.30:1, for example 0.01 to 0.20:1, for example 0.01 to 0.10:1, for example 0.02 to 0.04:1.

For example, the invention provides a composition comprising the following components in the following weight ratios:
a) ascorbate anion: 0.78 to 1.2 parts;
b) polyethylene glycol: 1.0 part;
c1) sodium chloride: 0.005 to 1.0 parts; and
c2) potassium chloride: 0.005 to 1.0 parts;
the ascorbate anion being provided by one or more salts of ascorbic acid;
the composition being essentially free from ascorbic acid.

The composition is preferably essentially free from sodium bicarbonate. For example, it is essentially free from any bicarbonate.

Preferred alkali metal or alkaline earth metal sulphates are as set out above in section 5a) in relation to solutions of the invention. For example, the composition may comprise a sulphate component (for example sodium sulphate) in a weight ratio to PEG of 0.01 to 0.50:1, For example, the composition may comprise a sulphate component (for example sodium sulphate) in a weight ratio to PEG of 0.02 to 0.25:1, for example 0.03 to 0.22:1, for example 0.05 to 0.20:1, for example 0.10 to 0.20:1.

In an alternative preferred embodiment, the composition does not comprise a sulphate component; that is to say that the composition is essentially free from alkali metal sulphates and alkaline earth metal sulphates; in particular essentially free from sodium sulphate, potassium sulphate and magnesium sulphate.

Preferred flavouring agents are as set out above in section 5a) in relation to solutions of the invention. For example the composition may comprise a flavouring agent in a weight ratio to PEG of 0.0005 to 0.05:1, for example 0.001 to 0.050:1, for example 0.003 to 0.030:1.

Preferred sweeteners are as set out above in section 5a) in relation to solutions of the invention. For example the composition may comprise a sweetener in a weight ratio to PEG of 0.0005 to 0.025:1, for example 0.001 to 0.050:1, for example 0.01 to 0.035:1.

In particular, the invention provides a composition comprising the following components in the following weight ratios:
a) ascorbate anion: 0.78 to 1.2 parts
b) PEG having an average molecular weight of 3000 to 4000 Da: 1.0 part.
c) sodium chloride and potassium chloride;
d) optionally sodium sulphate;
e) optionally one or more flavouring agents; and
f) optionally one or more sweeteners.
the ascorbate anion being provided by one or more salts of ascorbic acid;
the composition being essentially free from ascorbic acid.

Each of c) and d) may be present in the weight ratios to PEG described above. Each of e) and f) may be as described above and/or be in the weight ratios to PEG described above.

In one embodiment, the invention provides a composition comprising the following components in the following weight ratios:
a) sodium ascorbate: 0.90 to 1.125 parts
b) PEG having an average molecular weight of 3000 to 4000 Da: 1 part
c) sodium chloride 0.04 to 0.10 parts and litre potassium chloride 0.02 to 0.04 parts;
e) one or more flavouring agents: 0.001 to 0.075 parts; and
f) one or more sweeteners: 0.002 to 0.050 parts.

For example, the composition may comprise the following components in the following weight ratios:
a) sodium ascorbate: 1.0 parts
b) PEG having an average molecular weight of 3000 to 4000 Da: 1 part
c) sodium chloride 0.0625 parts and litre potassium chloride 0.0225 parts;
e) one or more flavouring agents: 0.001 to 0.075 parts; and
f) one or more sweeteners: 0.002 to 0.050 parts.

For example, the flavouring and sweetener may be 0.020 parts orange flavour and 0.0275 parts aspartame. For example, the flavouring and sweetener may be 0.040 parts lemon/lime flavour and 0.041 parts aspartame. For example, the flavouring and sweetener may be 0.054 parts orange flavour and 0.041 parts aspartame.

In an embodiment, the composition consists essentially of those components; that is to say that it does not contain any further components in significant quantities. The composition may, for example, not contain any sulphate.

Preferred compositions of the invention are dry compositions, for example dry powder compositions.

f) Methods of Preparing Solutions and Compositions

The invention further provides a method of preparing a solution of the invention comprising combining the components of the solution with water. The method comprises the step of combining the components with water and admixing. Some or all of the components may be in physical association with each other before the water is added. In some embodiments, the components of the composition are provided in more than one part; that is to say that they are packaged separately. All of the components may be combined with each other before combining with water. For example, if flavouring agent and sweetener are packaged separately from other components, they may be combined with the other components before combining with water. One or some of the components may be combined with water and admixed in a first step and then or all of the remaining components may be added in a second step. For example, the components may be in dry form, for example in powder form.

As set out above in section 5d), the invention provides a composition (for example a dry composition, for example a powder) for the preparation of a solution of the invention. The invention further provides a method of preparing a composition of the invention comprising combining the components of the composition. For example, the method may be a method of preparing a composition of the invention in powder form. The method may comprise blending a mixture of:
- a) ascorbate anion 0.78 to 1.2 parts; and
- b) polyethylene glycol 1.0 part;

the ascorbate anion being provided by one or more salts of ascorbic acid;
the composition being essentially free from ascorbic acid Preferred ascorbate salts are as set out above in section 5a). Preferred ratios of components a) and b) as as set out above in section 5a). Preferably the ascorbate anion is in a weight ratio to PEG of 0.80 to 1.0:1. More preferably, the weight ratio is 0.85 to 0.95:1, for example 0.86 to 0.90:1, for example 0.88:1.

The preferred ascorbate salt is sodium ascorbate. Preferably the sodium ascorbate and PEG are in a weight ratio of 0.90 to 1.125:1. More preferably, the weight ratio is 0.956 to 1.069:1, for example 0.968 to 1.013:1, for example 0.99:1, for example 1:1.

The method may further comprise blending a mixture of:
- a) ascorbate anion: 0.78 to 1.2 parts;
- b) polyethylene glycol: 1.0 part;
- c1) sodium chloride: 0.005 to 1.0 parts; and
- c2) potassium chloride: 0.005 to 1.0 parts;

the ascorbate anion being provided by one or more salts of ascorbic acid;
the composition being essentially free from ascorbic acid.

Preferred ratio amounts of sodium chloride to PEG and potassium chloride to PEG are as set out above in section 5e).

The components may be weighed out and added together before blending, or the components may be added into a blend mixture in any desired order.

Blending of the compositions in bulk may, for example, be carried out on a tonne scale. After blending, the composition is divided into smaller portions for packaging into dosage amounts. The invention thus provides a method comprising the step of dividing bulk composition as set out in section 5e) above into smaller portions. The invention also provides a method comprising the step of filling containers with individual dosage amounts of bulk composition as set out in section 5e). The invention thus provides a method comprising the step of filling a container with a composition as set out in section 5d). The composition as set out in section 5d) may be presented in two or more parts. The method may thus comprise the step of filling a container with some but not all of the components of a composition as set out in section 5d).

6. METHODS OF CLEANSING AND SOLUTIONS FOR USE IN THEM a) Split-Dose Colon Cleansing Treatments The solutions and compositions of the first and second aspects of the invention set out in sections 2 to 5 above find particular use in split dose colon cleansing treatments in which the subject takes two different agents (for example two different solutions): a first colon cleansing agent (for example solution), followed by a second colon cleansing agent (for example solution). Herein, the "second colon cleansing agent" means the agent that is taken chronologically second, after the "first colon cleansing agent". Preferably, the solution of the first or second aspect of the invention is the second colon cleansing agent. Alternatively, it may be the first agent. The invention thus provides, in a third aspect a method of cleansing the colon of a mammal comprising:
- the subject taking an effective amount of a first colon cleansing agent; and then
- the subject taking an effective amount of a second colon cleansing agent, the second colon cleansing agent being a solution of the first or second aspect of the invention described above. Preferably, the first colon cleansing agent is of different composition from the second colon cleansing agent. The first colon cleansing agent may be a colon cleansing solution. Alternatively, it may be a colon cleansing agent in solid form, for example in the form of a tablet, for example a PEG-containing tablet, or a bisacodyl-containing tablet. The first colon cleansing agent may, for example, contain a laxative, for example a stimulant laxative. For example, bisacodyl, castor oil, senna or bisoxatin may be used.

The invention also provides a method of cleansing the colon of a mammal comprising:
- the subject taking an effective amount of a first colon cleansing agent; and then
- the subject taking an effective amount of a second colon cleansing agent, the second colon cleansing agent being a solution comprising
- a) 300 to 800 mmol per litre ascorbate anion provided by a mixture of:
  - (i) ascorbic acid and
  - (ii) one or more salts of ascorbic acid the components (i) and (ii) being present in a molar ratio of from 1:4.5 to 1:7.0; and
- b) optionally 10 to 200 g per litre polyethylene glycol.

The invention also provides a method of cleansing the colon of a mammal comprising:
- the subject taking an effective amount of a first colon cleansing agent; and then
- the subject taking an effective amount of a second colon cleansing agent, the second colon cleansing agent being a solution comprising
- a) 360 to 440 mmol per litre ascorbate anion provided by one or more salts of ascorbic acid; and
- b) optionally 10 to 200 g per litre polyethylene glycol;

the solution being essentially free from ascorbic acid.

The method of the invention may be used to cleanse the colon prior to carrying out a diagnostic, therapeutic or surgical procedure on the colon, rectum or anus or elsewhere in the abdomen. The diagnostic or surgical procedure may, for example, be colonoscopy, barium enema examination, sigmoidoscopy or colon surgery. The method of the invention is generally finished less than 8 hours before carrying out the diagnostic, therapeutic or surgical procedure on the colon, rectum or anus or elsewhere in the abdomen. Preferably, it is finished less than 4 hours before.

The invention further provides a method of conducting a diagnostic or surgical procedure, for example, a colonoscopy, barium enema examination, sigmoidoscopy or colon surgery, comprising the steps of:
- a) cleansing the colon by a method of the invention, and then b) carrying out the diagnostic or surgical procedure.

The invention further provides a first colon cleansing agent, and a second colon cleansing agent, for use in a method of cleansing the colon comprising:
the subject taking an effective amount of a first colon cleansing agent;
the subject taking an effective amount of a second colon cleansing agent, the second colon cleansing agent being a solution of the first or second aspect of the invention described above.

The invention further provides a first colon cleansing agent, and a second colon cleansing agent, for use in a method of cleansing the colon comprising:
the subject taking an effective amount of a first colon cleansing agent;
the subject taking an effective amount of a second colon cleansing agent,
the second colon cleansing agent being a solution in water of:
a) 300 to 800 mmol per litre ascorbate anion provided by a mixture of
(i) ascorbic acid and
(ii) one or more salts of ascorbic acid
the components (i) and (ii) being present in a molar ratio of from 1:4.5 to 1:7.0; and
b) optionally 10 to 200 g per litre polyethylene glycol.

In an embodiment, the first agent is different from the second.

The invention further provides a first colon cleansing agent, and a second colon cleansing agent, for use in a method of cleansing the colon comprising:
the subject taking an effective amount of a first colon cleansing agent;
the subject taking an effective amount of a second colon cleansing agent,
the second colon cleansing agent being a solution in water of:
a) 360 to 440 mmol per litre ascorbate anion provided by one or more salts of ascorbic acid; and
b) optionally 10 to 200 g per litre polyethylene glycol.
the solution being essentially free from ascorbic acid.

In an embodiment, the first agent is different from the second. Further details of possible first colon cleansing agents are provided below in section 6b)

The second colon cleansing agent is preferably as described hereinabove in sections 2 to 5 in relation to solutions and uses of the first and second aspects of the invention. It is preferably used in a volume as described hereinabove in relation to solutions and uses of the invention as described hereinabove in sections 2 to 5.

The first and second colon cleansing agents may be provided in a kit. Further details of such kits are provided in section 8) below.

b) The "First" Colon Cleansing Agent

The first cleansing agent may be a solution, referred to as the first colon cleansing solution. The first colon cleansing solution may, for example, be a bowel content suspending agent. The first colon cleansing solution may comprise polyethylene glycol and/or an alkali metal sulphate, an alkaline earth metal sulphate or a mixture thereof. The first colon cleansing solution may be hyper-osmotic.

Preferably, the first colon cleansing solution comprises polyethylene glycol (PEG). The polyethylene glycol (PEG) may have an average molecular weight of 2000 to 8000, for example 2500 to 4500 Da, for example 2680 to 4020 Da, for example 3000 to 4000 Da. For example, the PEG may be PEG 3350 or PEG 4000 as defined in national pharmacopeias. PEG8000 may also be used. Further examples of suitable PEGs recognized in some national pharmacopeias include Macrogols, for example Macrogol 3350 or Macrogol 4000.

Preferably, the first colon cleansing solution comprises 70 to 250 g per litre of PEG. Preferably, the solution comprises 130 to 250 g per litre PEG, for example 90 to 200 g per litre of PEG, more preferably 100 to 200 g per litre, for example 120 to 150 g per litre, for example 133.3 g per litre; for example 150 to 250 g per litre, for example 175 to 225 g per litre, for example 200 g per litre.

Preferably, the first colon cleansing solution comprises one or more alkali metal sulphates, alkaline earth metal sulphates or a mixture thereof (herein referred to as a "sulphate component"). An alkali metal or alkaline earth metal sulphate may, for example, be selected from sodium sulphate, potassium sulphate and magnesium sulphate. The solution may comprise more than one of sodium sulphate, potassium sulphate and magnesium sulphate, for example all three. Preferably, the sulphate component is or includes sodium sulphate.

Preferably, the first colon cleansing solution comprises a sulphate component (for example sodium sulphate) at a concentration of 2 to 20 g per litre, for example 2 to 15 g per litre, for example 5 to 15 g per litre, for example 8 to 12 g per litre, for example 8 or 12 g per litre; for example 10 to 20 g per litre, for example 15 to 20 g per litre, for example 17 to 19 g per litre, for example 18 g per litre. For example, the first colon cleansing solution comprises 8.0 to 20 g per litre of one or more alkali metal sulphates, alkaline earth metal sulphates or a mixture thereof.

Accordingly, the first colon cleansing solution may comprise:
(i) 70 to 250 g per litre PEG having an average molecular weight of 2500 to 4500 Da.
(ii) 2.0 to 20 g per litre of one or more alkali metal sulphates, alkaline earth metal sulphates or a mixture thereof
(iii) optionally one or more electrolytes;
(iv) optionally one or more flavouring agents; and
(v) optionally one or more sweeteners.

The first colon cleansing solution may comprise one or more electrolytes. Electrolytes include salts of sodium, potassium, calcium and magnesium, particularly sodium and potassium; and salts of chloride, iodide, bicarbonate and carbonate, particularly chloride. Preferred electrolytes are sodium chloride and potassium chloride. In an embodiment, sodium bicarbonate is not included.

For example, the first colon cleansing solution may comprise sodium chloride at a concentration of 0.5 to 5.0 g per litre. For example, sodium chloride may be present at a concentration of 1.0 to 4.0 g per litre, for example 1.0 to 3.0 g per litre, for example 1.5 to 3.0 g per litre, for example 2.0 to 3.0 g per litre; for example 3.0 to 5.0 g per litre, for example 3.5 to 4.5 g per litre, for example 4.0 g per litre.

For example, the first colon cleansing solution may comprise potassium chloride at a concentration of 1 to 10 g per litre. For example, potassium chloride may be present at a concentration of 0.05 to 5.0 g per litre, for example 0.1 to 3.0 g per litre, for example 0.2 to 2.0 g per litre, for example 0.5 to 1.5 g per litre, for example 0.5 to 1.1 g per litre; for example 1.5 to 2.5 g per litre, for example 1.8 to 2.2 g per litre, for example 2.0 g per litre.

In an embodiment, the first colon cleansing solution comprises sodium chloride and potassium chloride. They can be present in the amounts mentioned immediately above. For example, sodium chloride may be present at a concentration of 1.0 to 3.0 g per litre and potassium chloride may be present at a concentration of 2.5 to 3.0 g per litre; for example, sodium chloride may be present at a concentration of 3.0 to 5.0 g per litre and potassium chloride may be present at a concentration of 0.5 to 1.1 g per litre.

In an embodiment, the first colon cleansing solution comprises sodium chloride and potassium chloride. They can be present in the amounts mentioned immediately above. For example, sodium chloride may be present at a concentration of 1.5 to 3.0 g per litre and potassium chloride may be present at a concentration of 0.2 to 2.0 g per litre; for example, sodium chloride may be present at a concentration of 3.0 to 5.0 g per litre and potassium chloride may be present at a concentration of 1.5 to 2.5 g per litre.

For example, the first colon cleansing solution comprises:
(i) 90 to 200 g per litre PEG having an average molecular weight of 2500 to 4500 Da.
(ii) 2.0 to 15 g per litre of one or more alkali metal sulphates, alkaline earth metal sulphates or a mixture thereof
(iii) 0.5 to 5.0 g per litre sodium chloride, and 0.05 to 5.0 g per litre potassium chloride;
(iv) optionally one or more flavouring agents; and
(v) optionally one or more sweeteners.

In an embodiment, the first colon cleansing solution may be a solution as commercialised under the tradename MOV-IPREP®.

The first colon cleansing solution preferably includes a flavouring agent. The first colon cleansing solution preferably includes a sweetener. Flavouring agents and sweeteners may be as described hereinabove.

For example, a flavouring for use in in the first colon cleansing solution should preferably mask saltiness, be relatively sweet but not excessively so, and be stable in the composition. A flavouring makes the solutions more palatable and thus aids patient compliance. Preferred flavourings include lemon e.g. Ungerer Lemon (available from Ungerer Limited, Sealand Road, Chester, England CH1 4LP) strawberry e.g. Ungerer Strawberry, grapefruit e.g. Ungerer Grapefruit flavouring powder, blackcurrant e.g. Ungerer Blackcurrant, pineapple e.g. IFF (International Flavours and Fragrances) Pineapple flavouring powder, orange eg Firmenich Orange, and vanilla/lemon and lime e.g. IFF Vanilla and Givaudin Roure Lemon and Lime Flav-o-lok, fruit punch eg Ungerer fruit punch, citrus punch, mango, and berry. Those and further suitable flavourings are available from International Flavours and Fragrances Inc. (Duddery Hill, Haverhill, Suffolk, CB9 8LG, England), Ungerer & Company (Sealand Road, Chester, England CH1 4LP) or Firmenich (Firmenich UK Ltd., Hayes Road, Southall, Middlesex UB2 5NN). More preferred flavourings are lemon, kiwi, strawberry grapefruit, fruit punch and mango. Fruit punch and mango are especially preferred flavours.

A particularly preferred flavouring is fruit punch flavour, for example at a level of 0.4 to 3.5 g per litre, for example 0.4 to 1.2 g per litre, for example 0.938, 1.0 or 3.18 g per litre.

The first cleansing solution preferably includes a sweetener. Preferred sweeteners include aspartame, acesulfame potassium (acesulfame K), sucralose and saccharine, and/or combinations thereof. For example, the solution may comprise one or both of aspartame and acesulfame potassium (acesulfame K). For example, it may comprise one or both of sucralose and acesulfame potassium (acesulfame K). In a preferred embodiment, the solution comprises aspartame or sucralose, for example sucralose. Preferred sweeteners include aspartame, acesulfame potassium (acesulfame K), sucralose and saccharine, and/or combinations thereof. For example, compositions of the invention may comprise one or both of aspartame and acesulfame potassium (acesulfame K). For example, compositions of the invention may comprise one or both of sucralose and acesulfame potassium (acesulfame K). In a preferred embodiment, the solution comprises aspartame or sucralose, for example aspartame.

Alternatively, compositions of the invention can be essentially free from added sweeteners, for example to minimize the number of different components in the compositions.

A souring agent (for example citric acid) may be present as a taste enhancer. A souring agent is a component that imparts a sourness to a composition. Other souring agents include malic acid, acetic acid, tartaric acid, gluconodeltalactone, phosphoric acid, succinic acid, phytic acid, lactic acid or salts thereof. It may be present at a level of from 0.1 to 3.0 g per litre, for example 0.3 to 2.0 g per litre, for example 0.5 to 2.0 g per litre, for example 0.75 g, 1.0 g, 1.06 g, 1.25 g or 1.5 g per litre. The souring agent (for example citric acid) may be provided in an encapsulated form. The encapsulation provides a coating that isolates the souring agent from other components and from air and moisture prior to its use. Several encapsulated forms of citric acid, or other souring agents, are commercially available. For example, the encapsulation may be with a water-soluble coating.

The amount of sweetener required depends on the nature and strength of the sweetener being considered. Typically, it is 0.10 to 4 g per litre. For example, the sweetener may be sucralose at 0.1 to 3.0 g per litre, for example 0.3 to 2.0 g per litre, for example 0.5 to 2.0 g per litre, for example 0.5 to 1.3 g per litre for example 0.63 g, 0.80 g, 1.0 g or 1.58 g per litre.

The first cleansing solution may include one or more further optional components. Such components may be as set out above in section 3b).

In an embodiment, the first colon cleansing solution has a volume of from 400 to 600 ml (for example 500 ml), and contains the quantities of solutes described in the section immediately above. For example the volume may be 16 or 17 US fluid ounces. For example, the invention provides colon cleansing solution comprising:
(i) 175 to 220 g per litre PEG having an average molecular weight of 2500 to 4500 Da.
(ii) 15 to 20 g per litre of one or more alkali metal sulphates, alkaline earth metal sulphates or a mixture thereof
(iii) 3.0 to 5.0 g per litre sodium chloride, and 1.5 to 2.5 g per litre potassium chloride;
(iv) optionally one or more flavouring agents; and
(v) optionally one or more sweeteners.

Such a solution has a smaller volume than cleansing solutions that are generally used.

In an embodiment, the first colon cleansing solution is provided in a volume of from 300 ml up to 1200 ml. For example, the first solution may have a volume in a range with a lower limit of 300 ml, 400 ml, 500 ml, 600 ml or 700 ml. Preferably, the lower limit is 500 ml, 600 ml or 700 ml. The volume may be in a range with an upper limit of 1200 ml, 1100 ml, 1000 ml, 900 ml or 800 ml. For example the volume may be in the range 400 ml to 1100 ml, for example 500 ml to 1000 ml, for example 600 ml to 900 ml, for example 700 ml to 800 ml. For example, the first colon cleansing solution is provided in a volume of 750 ml. For example the volume may be in the range 400 ml to 600 ml. For example, the first colon cleansing solution is provided in a volume of 500 ml. For example it may be in a volume of 16 or 17 US fluid ounces. The most appropriate volume will depend on the exact components of the solution and the amounts in which they are present. In general, for a solution of higher osmotic strength, a smaller volume will be required.

The first cleansing solution may, for example, have a measured osmolality in the range 200 to 2000 mOsmol/kg, 200 to 1500 mOsmol/kg. In a preferred embodiment, it is hyper-osmotic. It may, for example have a measured osmolality in the range 320 to 1500 mOsmol. For example, the measured osmolality of the first cleansing solution is in the range 330 to 1200 mOsmol/kg, for example 340 to 1000 mOsmol/kg, for example 350 to 800 mOsmol/kg, for example 350 to 700 mOsmol/kg. For example, the solutes in the solution may have a V(350) value of from 800 to 1600 ml, for example from 1000 to 1400 ml, for example from 1150 to 1250 ml, and be in a volume of 400 to 600 ml, for example 500 ml.

The invention further provides a composition optionally presented in two or more parts for the preparation of a first colon cleansing solution. For example the composition may comprise:
(i) 87.5 to 110 g PEG having an average molecular weight of 2500 to 4500 Da.
(ii) 7.5 to 10 g of one or more alkali metal sulphates, alkaline earth metal sulphates or a mixture thereof
(iii) 1.5 to 2.5 g sodium chloride and 0.75 to 1.25 g potassium chloride;
(iv) optionally one or more flavouring agents; and
(v) optionally one or more sweeteners.

For example the composition may comprise:
(i) 100 g PEG having an average molecular weight of 3000 to 4000 Da.
(ii) 9.0 g sodium sulphate
(iii) 2.0 g sodium chloride and 1.0 g potassium chloride;
(iv) optionally one or more flavouring agents; and
(v) optionally one or more sweeteners.

For example, the flavouring and sweetener may be 0.469 g fruit punch flavouring, 0.476 g sucralose and 0.792 g citric acid. For example, the flavouring and sweetener may be 0.500 g fruit punch flavouring, 0.40 g sucralose and 0.75 g citric acid. For example, the flavouring and sweetener may be 1.43 g mango flavouring, 0.79 g sucralose and 1.74 g citric acid. For example, the flavouring and sweetener may be 1.59 g fruit punch flavouring, 0.79 g sucralose and 1.74 g citric acid. Citric acid may optionally be packaged separately from the other components.

Particular first solutions S1 and S2, and particular second solutions T1 and T2 are described in the examples section below. In a preferred aspect of the present invention, there is provided a method of cleansing the colon of a subject comprising (or consisting essentially of):
administering to the subject a cleansing solution of S2 as set forth herein;
administering to the subject a cleansing solution of T1 as set forth herein.

In preferred embodiments of this aspect of the invention, the cleansing solution of S2 is administered to the subject before the cleansing solution of T1 is administered. It is particularly preferred that S2 is administered to the subject and then, following a time interval (such as disclosed herein), T1 is administered to the subject. In further preferred embodiments of this aspect of the invention, additional fluid (such as clear fluid) is administered to the subject in conjunction with S2 and/or T1. For example, additional clear fluid (such as 500 ml or thereabout, or 1000 ml or thereabout) is administered to the subject following administration of S2 and/or T1. Alternatively, additional clear fluid is administered to the subject during administration of S2 and/or T1. In typical embodiments, the cleansing solution of S2 and/or T1 is self-administered.

7. USE OF SWEETENER IN COLON CLEANSING SOLUTION

It has been found by the current inventors that a sulphate-containing colon cleansing solution that contains a souring agent (for example citric acid) and sucralose is particularly palatable.

The invention further provides, according to a fourth aspect, a colon cleansing solution comprising:
(i) 70 to 250 g per litre PEG having an average molecular weight of 2500 to 4500 Da;
(ii) 2.0 to 20 g per litre of one or more alkali metal sulphates, alkaline earth metal sulphates or a mixture thereof;
(iii 1) optionally 1.0 to 5.0 g per litre sodium chloride;
(iii 2) optionally 0.5 to 1.5 (for example 0.5 to 1.1) g per litre potassium chloride;
(iv) optionally one or more flavouring agents;
(v) sucralose; and
(vi) one or more souring agents.

Further, the invention provides a method for improving the palatability of a sulphate-containing colon cleansing solution comprising including in the solution 0.1 to 3.0 g per litre sucralose and 0.1 to 4.0 g per litre of souring agent, for example 0.1 to 3.0 g per litre of souring agent, for example citric acid. The invention provides a method for diminishing the poor taste of a sulphate-containing colon cleansing solution comprising including in the solution 0.1 to 3.0 g per litre sucralose and 0.1 to 4.0 g of souring agent, for example 0.1 to 3.0 g per litre of souring agent, for example citric acid.

It is postulated that the improved palatability is associated with a reduced perceived saltiness of the solutions. The invention thus provides a method for reducing the perceived saltiness of a sulphate-containing colon cleansing solution comprising including in the solution 0.1 to 3.0 g per litre sucralose and 0.1 to 4.0 g per litre of souring agent, for example 0.1 to 3.0 g per litre of souring agent, for example citric acid. "Reduction" here is taken to mean as compared with an equivalent solution without the sucralose and souring agent.

A souring agent may be selected from citric acid, malic acid, acetic acid, tartaric acid, gluconodeltalactone, phosphoric acid, succinic acid, phytic acid, lactic acid or salts thereof. For example, the souring agent may be citric acid. It may be present at a level of from 0.1 to 4.0 g per litre, for example 0.1 to 3.0 g per litre, for example 0.3 to 2.0 g per litre, for example 0.5 to 2.0 g per litre, for example 0.75 g, 1.0 g, 1.06 g, 1.25 g or 1.5 g per litre. For example, it may be at a level of 3.0 to 4.0 g per litre, for example 3.48 g per litre. Citric acid, or another souring agent, may be provided in an encapsulated form. The encapsulation provides a coating that isolates the souring agent from other components and from air and moisture prior to its use. Several encapsulated forms of citric acid, or other souring agents, are commercially available. For example, the encapsulation may be with a water-soluble coating.

The sucralose may, for example be present at a level of 0.1 to 3.0 g per litre, for example 0.3 to 2.0 g per litre, for example 0.5 to 2.0 g per litre, for example 0.5 to 1.3 g per litre for example 0.63 g, 0.80 g, or 1.0 g per litre. For example, it may be at a level of 1.58 g per litre.

When sucralose and citric acid are used, a particularly preferred flavouring is fruit punch flavour, for example at a level of 0.4 to 1.2 g per litre, for example 0.625 g per litre or 1.0 g per litre.

There is also provided a composition for the preparation of such a solution, for example by admixture with water. Preferred amounts of each of components (i) to (iv) in the solutions and compositions of the fourth aspect of the invention are as set out for the first colon cleansing solutions and first colon cleansing compositions hereinabove in section 6b).

A colon cleansing solution according to the fourth aspect of the invention may contain PEG, sulphate, sodium chloride, potassium chloride and flavouring in amounts and types as described hereinabove in relation to the first colon cleansing solution in section 6b).

A colon cleansing solution according to the fourth aspect of the invention may be used together with a solution of the first or second aspect of the invention as set out in sections 2 to 5. Alternatively, it may be used in combination with a different other colon cleansing solution, or used in a suitable volume on its own. If used on its own, it may be used in a single dose or in a split dose administration. The invention provides a method of cleansing the colon of a subject comprising administering a solution of the fourth aspect of the invention. The solution may be administered on its own or in combination with a further, different, solution.

8. KITS a) Kits Providing a Composition for the Preparation of a Solution of the Invention As set out above in section 2d), the invention provides a composition for admixture with water (for example a dry composition, for example a powder), wherein the composition is optionally presented in two or more parts and comprises the components of a solution of the invention. If the components are provided in two or more parts, they may be provided in a kit. The invention thus provides a kit comprising:
- a) 150 to 400 mmol ascorbate anion provided by a mixture of:
  - (i) ascorbic acid and
  - (ii) one or more salts of ascorbic acid
the components (i) and (ii) being present in a molar ratio of from 1:4.5 to 1:7.0; and
- b) 5 to 100 g polyethylene glycol.

The kit may further comprise additional components as set out in sections 3a), 3b) and 3d) above, and in the amounts set out there. For example, the kit may contain:
- a) 150 to 400 mmol ascorbate anion provided by a mixture of:
  - (i) ascorbic acid and
  - (ii) one or more salts of ascorbic acid
the components (i) and (ii) being present in a molar ratio of from 1:4.5 to 1:7.0;
- b) 5 to 100 g PEG having an average molecular weight of 3000 to 4000 Da.
- c) sodium chloride and potassium chloride;
- d) optionally sodium sulphate;
- e) optionally one or more flavouring agents;
- f) optionally one or more sweeteners.

Each of c) and d) may be present in the amounts described in section 3a) and 3d) above. Each of e) and f) may be as described above and/or be in the amounts described in section 3a) and 3d) above.

In one embodiment, the kit contains:
- a)
  - (i) 6.0 to 10 g ascorbic acid and
  - (ii) 40 to 60 g sodium ascorbate
  the components (i) and (ii) being present in a weight ratio of from 1:5063 to 1:7.875;
- b) 30 to 50 g PEG having an average molecular weight of 3000 to 4000 Da;
- c) 1.5 to 4 g sodium chloride and 0.5 to 3.5 g potassium chloride;
- e) one or more flavouring agents; and
- f) one or more sweeteners.

In an embodiment of a kit of the invention, the ascorbate component a) is packaged separately from the PEG component b). The remaining elements may be packaged together with the PEG component.

In an embodiment of a kit of the invention, the flavouring component e) or the sweetener component f) may be provided separately from other components. The kit may provide several alternative flavourings, allowing the subject to decide themselves which flavouring from a range of flavourings to use.

For example, the kit may contain:
- a)
  - (i) 7.54 g ascorbic acid and
  - (ii) 48.11 g sodium ascorbate
- b) 40 g PEG having an average molecular weight of 3000 to 4000 Da;
- c) 3.20 g sodium chloride and 1.20 g potassium chloride;
- e) one or more flavouring agents; and
- f) one or more sweeteners;
whereby component a) is packaged in a first compartment and components b), c) e) and f) are packaged in a second compartment.

One or more of the components may be in a dry powder form (for example the ascorbate component or the PEG component may be in dry powder form), whilst some of the remaining components (for example the sodium chloride or the potassium chloride) are in the form of a tablet or in a semi-solid (for example gel) form. In such an embodiment, the subject may be instructed to dissolve the powder components in water and drink it, and instructed to take the tablet or semi-solid form without dissolution. If a semi-solid form (for example gel) is present, the subject may be instructed to add it to water before ingesting it, or the subject may be instructed to take it as provided.

As set out above in section 5d), the invention provides a composition for admixture with water (for example a dry composition, for example a powder), wherein the composition is optionally presented in two or more parts and comprises the components of a solution of the invention. If the components are provided in two or more parts, they may be provided in a kit. The invention thus provides a kit comprising:
- a) 180 to 220 mmol ascorbate anion provided by one or more salts of ascorbic acid; and
- b) 5 to 100 g polyethylene glycol;
the kit being essentially free from ascorbic acid.

The kit may further comprise additional components as set out in sections 5a), 5b) and 5d) above, and in the amounts set out there. For example, the kit may contain:
- a) 180 to 220 mmol ascorbate anion provided by one or more salts of ascorbic acid;
- b) 5 to 100 g PEG having an average molecular weight of 3000 to 4000 Da.
- c) sodium chloride and potassium chloride;

d) optionally sodium sulphate;
e) optionally one or more flavouring agents;
f) optionally one or more sweeteners;
the kit being essentially free from ascorbic acid.

Each of c) and d) may be present in the amounts described in section 5a) and 5d) above. Each of e) and f) may be as described above and/or be in the amounts described in section 5a) and 5d) above.

In one embodiment, the kit contains:
a) 35.65 to 43.55 g sodium ascorbate
b) 30 to 50 g PEG having an average molecular weight of 3000 to 4000 Da;
c) 1.5 to 4 g sodium chloride and 0.5 to 3.5 g potassium chloride;
e) one or more flavouring agents; and
f) one or more sweeteners;
the kit being essentially free from ascorbic acid.

In an embodiment of a kit of the invention, the ascorbate component a) is packaged separately from the PEG component b). The remaining components may be packaged together with the PEG component.

In an embodiment of a kit of the invention, the flavouring component e) or the sweetener component f) may be provided separately from other components. The kit may provide several alternative flavourings, allowing the subject to decide themselves which flavouring from a range of flavourings to use.

For example, the kit may contain:
a) 40 g sodium ascorbate
b) 40 g PEG having an average molecular weight of 3000 to 4000 Da;
c) 2.50 g sodium chloride and 0.90 g potassium chloride;
e) one or more flavouring agents; and
f) one or more sweeteners;
whereby component a) is packaged in a first compartment and components b), c) e) and f) are packaged in a second compartment.

In a further embodiment, one or more of the components may be in a dry powder form (for example the ascorbate component or the PEG component may be in dry powder form), whilst some of the remaining components (for example the sodium chloride or the potassium chloride) are in the form of a tablet or in a semi-solid (for example gel) form. In such an embodiment, the subject may be instructed to dissolve the powder components in water and drink it, and instructed to take the tablet or semi-solid form without dissolution. If a semi-solid form (for example gel) is present, the subject may be instructed to add it to water before ingesting it, or the subject may be instructed to take it as provided.

It is convenient for the patient for a kit of the invention to be provided in the form of, for example, a box. In a kit of the invention the first and/or second parts may each contained in one or more containers. Examples of suitable containers include tubs, bags and sachets. A preferred container is a sachet.

In one embodiment, the composition of the invention can be provided in a multi-chambered container, for example of the type disclosed in WO2012/105524. A multi-chambered container may have a partition wall and two separate powders can be stored separated from each other. In addition, in a container of the type disclosed in WO2012/105524, a powdered medicine, which has been stored in a separated state, can be simply and readily mixed at the time of use to provide an aqueous solution.

For example, a multi-chambered container comprises a substantially flat pouch formed from a flexible film, a partition wall configured as a detachable seal detachably welding opposing inner surfaces of the pouch, and a pour port for infusion and discharge of a liquid, that is attached to the periphery of the pouch so as to open into one of the plurality of partitioned chambers. For example, the partition wall comprises a horizontal section which extends along a gusseted bottom section of the pouch and a perpendicular section which is curved from the horizontal section to a pouch upper section. The partition wall may, for example, be frangible. For example, a first partitioned chamber having a large capacity is formed on one side of the partition wall close to the bottom section of the pouch, a second partitioned chamber having a small capacity is formed on the other side of the partition wall, and the pour port opens into the first partitioned chamber.

b) Kits Providing Treatments According to the Invention

As set out above in section 6), the invention provides various split-dose treatments for colon cleansing in which the subject takes two different agents. The invention thus provides a kit comprising:
a first colon cleansing agent, and
a second colon cleansing agent,
the second colon cleansing agent being a solution of the first or second aspect of the invention described above.

The invention provides a kit comprising:
a first colon cleansing agent, and
a second colon cleansing agent,
the second colon agent solution being a solution in water of:
a) 300 to 800 mmol per litre ascorbate anion provided by a mixture of
  (i) ascorbic acid and
  (ii) one or more salts of ascorbic acid
the components (i) and (ii) being present in a molar ratio of from 1:4.5 to 1:7.0; and
b) optionally 10 to 200 g per litre polyethylene glycol.

The invention also provides a kit comprising:
a first colon cleansing agent, and
a second colon cleansing agent,
the second colon cleansing agent being a solution in water of:
a) 360 to 440 mmol per litre ascorbate anion provided by one or more salts of ascorbic acid; and
b) optionally 10 to 200 g per litre polyethylene glycol;
the solution being essentially free from ascorbic acid.

In an embodiment, the first agent is different from the second.

A kit of the invention may provide compositions for the preparation of the colon cleansing solutions. The invention thus further provides a kit comprising:
A) a first component, being a composition, optionally presented in two or more parts for the preparation of a first colon cleansing solution as described above by admixture with water; and
B) a second component, being a composition, optionally presented in two or more parts for the preparation of a second colon cleansing solution by admixture with water, the second colon cleansing solution being a solution as described hereinabove in relation to solutions and uses of the first or second aspects of the invention as set out in sections 2 to 5.

Preferably, the first solution is of different composition from the second.

Accordingly, a kit of the invention may comprise:
A) a first component, being a composition optionally presented in two or more parts for the preparation of a first colon cleansing solution comprising:

(i) 52.5 to 187.5 g PEG having an average molecular weight of 2500 to 4500 Da.
(ii) 1.5 to 15 g of one or more alkali metal sulphates, alkaline earth metal sulphates or a mixture thereof
(iii) optionally one or more electrolytes;
(iv) optionally one or more flavouring agents; and
(v) optionally one or more sweeteners, and B) a second component, being a composition optionally presented in two or more parts for the preparation of a second colon cleansing solution, comprising
a) 150 to 400 mmol ascorbate anion provided by a mixture of:
(i) ascorbic acid and
(ii) one or more salts of ascorbic acid
the components (i) and (ii) being present in a molar ratio of from 1:4.5 to 1:7.0; and
b) optionally 5 to 100 g polyethylene glycol,
the first solution being different from the second.

A kit of the invention may comprise:
A) a first component, being a composition optionally presented in two or more parts for the preparation of a first colon cleansing solution comprising:
(i) 52.5 to 187.5 g PEG having an average molecular weight of 2500 to 4500 Da.
(ii) 1.5 to 15 g of one or more alkali metal sulphates, alkaline earth metal sulphates or a mixture thereof
(iii) optionally one or more electrolytes;
(iv) optionally one or more flavouring agents; and
(v) optionally one or more sweeteners, and B) a second component, being a composition optionally presented in two or more parts for the preparation of a second colon cleansing solution, comprising
a) 360 to 440 mmol ascorbate anion provided one or more salts of ascorbic acid; and
b) optionally 5 to 100 g polyethylene glycol,
the solution being essentially free from ascorbic acid;
the first solution being different from the second.

The first component may be a composition for the preparation of a solution as set out in section 6b) above. The first component preferably comprises 97.5 to 187.5 g of PEG, for example 67.5 to 150 g of PEG, more preferably 75 to 150 g, for example 90 to 112.5 g, for example 100 g PEG.

Preferably, the first component comprises a sulphate component (for example sodium sulphate) in an amount of 1.5 to 11.25 g, for example 3.75 to 11.25 g, for example 6 to 9 g, for example 6 or 9 g. For example, the first component comprises 6.0 to 15 g of one or more alkali metal sulphates, alkaline earth metal sulphates or a mixture thereof. For example it comprises 9 g of sodium sulphate.

Preferably, the first component comprises sodium chloride in an amount of 0.375 to 3.75 g. For example, sodium chloride may be present in an amount of 0.75 to 3.0 g, for example 0.75 to 2.25 g, for example 1.125 to 2.25 g, for example 1.5 to 2.25 g, for example 2.0 g.

For example, the first component comprises potassium chloride in an amount of 0.75 to 7.5 g. For example, potassium chloride may be present in an amount of 0.0375 to 3.75 g, for example 0.075 to 2.25 g, for example 0.15 to 1.5 g, for example 0.375 to 1.125 g, for example 0.375 to 0.825 g, for example 1.0 g.

In an embodiment, the first component comprises sodium chloride and potassium chloride. They can be present in the amounts mentioned immediately above. For example, sodium chloride may be present in an amount of 1.125 to 2.25 g and potassium chloride may be present in an amount of 0.15 to 1.5 g; for example 2.0 g sodium chloride and 1.0 g potassium chloride.

The second component of the kit of compositions of the invention is preferably a composition for the preparation of a solution of the first or second aspect of the invention as described hereinabove in sections 3 or 5.

Accordingly, the kit may comprise:
A) a first component, being a composition optionally presented in two or more parts for the preparation of a first colon cleansing solution comprising:
(i) 87.5 to 110 g PEG having an average molecular weight of 2500 to 4500 Da.
(ii) 7.5 to 10 g of one or more alkali metal sulphates, alkaline earth metal sulphates or a mixture thereof
(iii) 1.5 to 2.5 g sodium chloride and 0.75 to 1.25 g potassium chloride;
(iv) optionally one or more flavouring agents; and
(v) optionally one or more sweeteners, and B) a second component, being a composition optionally presented in two or more parts for the preparation of a second colon cleansing solution, comprising
a)
(i) 6.0 to 10 g ascorbic acid and
(ii) 40 to 60 g sodium ascorbate
the components (i) and (ii) being present in a weight ratio of from 1:5063 to 1:7.875;
b) 30 to 50 g PEG having an average molecular weight of 3000 to 4000 Da;
c) 1.5 to 4 g sodium chloride and 0.5 to 3.5 g potassium chloride;
e) one or more flavouring agents; and
f) one or more sweeteners.

In an embodiment of a kit of the invention, in component B) the ascorbate component a) is packaged separately from the PEG component b). The remaining elements of component B) may be packaged together with the PEG component.

For example, a kit may comprise:
A) a first component, being a composition optionally presented in two or more parts for the preparation of a first colon cleansing solution comprising:
(i) 100 g PEG having an average molecular weight of 3000 to 4000 Da.
(ii) 9.0 g sodium sulphate
(iii) 2.0 g sodium chloride and 1.0 g potassium chloride;
(iv) optionally one or more flavouring agents; and
(v) optionally one or more sweeteners, and B) a second component for the preparation of a second colon cleansing solution, comprising
a)
(i) 7.54 g ascorbic acid and
(ii) 48.11 g sodium ascorbate
b) 40 g PEG having an average molecular weight of 3000 to 4000 Da;
c) 3.20 g sodium chloride and 1.20 g potassium chloride;
e) one or more flavouring agents; and
f) one or more sweeteners;
whereby component a) is packaged in a first compartment and components b), c) e) and f) are packaged in a second compartment.

For example, the flavouring and sweetener in the first component may be 0.469 g fruit punch flavouring, 0.476 g sucralose and 0.792 g citric acid. For example, the flavouring and sweetener may be 0.500 g fruit punch flavouring, 0.40 g sucralose and 0.75 g citric acid. For example, the flavouring and sweetener may be 1.43 g mango flavouring, 0.79 g sucralose and 1.74 g citric acid. For example, the flavouring and sweetener may be 1.59 g fruit punch flavouring, 0.79 g sucralose and 1.74 g citric acid. Citric acid may optionally be packaged separately from the other components.

For example, the flavouring and sweetener in the second component may be 0.60 g orange flavour and 1.93 g aspartame. For example, the flavouring and sweetener may be 1.60 g citrus flavour and 0.875 g aspartame. For example, the flavouring and sweetener may be 2.10 g orange grapefruit flavour and 0.875 g aspartame.

Alternatively, the kit may comprise:
A) a first component, being a composition optionally presented in two or more parts for the preparation of a first colon cleansing solution comprising:
  (i) 87.5 to 110 g PEG having an average molecular weight of 2500 to 4500 Da.
  (ii) 7.5 to 10 g of one or more alkali metal sulphates, alkaline earth metal sulphates or a mixture thereof
  (iii) 1.5 to 2.5 g sodium chloride and 0.75 to 1.25 g potassium chloride;
  (iv) optionally one or more flavouring agents; and
  (v) optionally one or more sweeteners,
and
B) a second component, being a composition optionally presented in two or more parts for the preparation of a second colon cleansing solution, comprising
  a) 35.65 to 43.55 g sodium ascorbate
  b) 30 to 50 g PEG having an average molecular weight of 3000 to 4000 Da;
  c) 1.5 to 4 g sodium chloride and 0.5 to 3.5 g potassium chloride;
  e) one or more flavouring agents; and
  f) one or more sweeteners.

In an embodiment of a kit of the invention, in component B) the ascorbate component a) is packaged separately from the PEG component b). The remaining elements of component B) may be packaged together with the PEG component.

For example, a kit may comprise:
A) a first component, being a composition optionally presented in two or more parts for the preparation of a first colon cleansing solution comprising:
  (i) 100 g PEG having an average molecular weight of 3000 to 4000 Da.
  (ii) 9.0 g sodium sulphate
  (iii) 2.0 g sodium chloride and 1.0 g potassium chloride;
  (iv) optionally one or more flavouring agents; and
  (v) optionally one or more sweeteners,
and
B) a second component for the preparation of a second colon cleansing solution, comprising
  a) 40 g sodium ascorbate
  b) 40 g PEG having an average molecular weight of 3000 to 4000 Da;
  c) 2.50 g sodium chloride and 0.90 g potassium chloride;
  e) one or more flavouring agents; and
  f) one or more sweeteners;
whereby component a) is packaged in a first compartment and components b), c) e) and f) are packaged in a second compartment.

For example, the flavouring and sweetener in the first component may be 0.469 g fruit punch flavouring, 0.476 g sucralose and 0.792 g citric acid. For example, the flavouring and sweetener may be 0.500 g fruit punch flavouring, 0.40 g sucralose and 0.75 g citric acid. For example, the flavouring and sweetener may be 1.43 g mango flavouring, 0.79 g sucralose and 1.74 g citric acid. For example, the flavouring and sweetener may be 1.59 g fruit punch flavouring, 0.79 g sucralose and 1.74 g citric acid. Citric acid may optionally be packaged separately from the other components.

For example, the flavouring and sweetener in the second component may be 0.80 g orange flavour and 1.10 g aspartame. For example, the flavouring and sweetener may be 1.60 g lemon/lime flavour and 1.625 g aspartame. For example, the flavouring and sweetener may be 2.15 g orange grapefruit flavour and 1.625 g aspartame.

Preferably, the kit further comprises instructions for use. In an embodiment, a kit of the invention has instructions that instruct the user of the volume to which each component is to be made up with water. For example, the specified volume of water for each solution is less than one litre. For example, the specified volume for the first component may be 300 ml to 1200 ml, for example 600 ml to 900 ml, for example 750 ml; for example it may be a volume of 25 or 26 US fluid ounces, for example 400 to 600 ml, for example 500 ml. For example it may be a volume of 16 or 17 US fluid ounces. For example, the specified volume for the second component may be from 250 ml to 1000 ml, for example 400 ml to 700 ml, for example 500 ml. For example it may be a volume of 16 or 17 US fluid ounces. Further volumes that may be specified in the instructions are the volumes set out hereinabove in relation to the methods of the invention.

In general, the instructions specify that the first and second solutions are to be ingested in succession with a time interval between them. In an embodiment, the instructions specify that the first cleansing solution is ingested first followed, after a time interval (for example the time between an evening and the following morning) by ingestion of the second cleansing solution. The time interval is preferably as described above in relation to the methods of the invention. The instructions may specify that the components in the kit be made up into solutions and then taken in accordance with the description set out above in section 6 for the first solution and sections 3c) and 5c) for the second solution.

For example, components A) and B) may be in dry powder, granular or other dry form. They may alternatively be in the form of concentrates or slurries. Components A) and B) may be in the same or different physical forms. Components within A) and B) may be in the same or different physical forms. For example, one or both of components A) and B) are dry powders. A portion of either or each of components A) and B) may be in the form of one or more solid tablets or capsules.

It is convenient for the patient for a kit of the invention to be provided in the form of, for example, a box. In a kit of the invention the first and/or second components may each contained in one or more containers. In particular, the second component may be contained in more than one container. For example, if the second component comprises both ascorbic acid and PEG then the ascorbic acid and PEG may be contained in separate containers. The other constituents of the second component (for example one or more of sodium chloride, potassium chloride and sodium sulphate) may be in either of the separate containers. For example, they may be in the container containing the PEG.

If a flavouring component is present in the first or second solution, then in a kit of the invention, the flavouring component for the relevant solution may be provided in a separate container from the other constituents of that solution.

Examples of suitable containers include tubs, bags and sachets. A preferred container is a sachet.

In one embodiment, the composition of the invention can be provided in a multi-chambered container, for example of the type disclosed in WO2012/105524, as described above in section 8a).

In one embodiment, a kit comprises:
A) a first sachet comprising a first composition for the preparation of the first cleansing solution;
B1) a second sachet;
B2) a third sachet;
wherein the second and third sachets together provide a composition for the preparation of the second cleansing solution.

For example, in a kit of the invention as mentioned immediately above:
A) the first sachet comprises polyethylene glycol and/or sodium sulphate;
B1) the second sachet comprises one or more components selected from polyethylene glycol, one or more alkali metal sulphates, alkaline earth metal sulphates or a mixture thereof and electrolytes; and
B2) the third sachet comprises one or more salts of ascorbic acid and, if appropriate, ascorbic acid;
the contents of sachets (B1) and (B2) together providing the components for the second cleansing solution.

For example, in a further embodiment of a kit of the invention, rather than being provided within a first sachet (A) with the PEG, some or all of the sulphate(s), electrolytes, flavouring agents and sweeteners are provided in the form of a tablet or capsule. In a further embodiment of a kit of the invention, rather than being provided within a second or third sachet (B1 or B2) with the PEG, ascorbic acid or ascorbate component, some or all of the sulphate(s), electrolytes, flavouring agents and sweeteners are provided in the form of a tablet or capsule.

A kit may contain one treatment, for example a cleansing treatment, or several treatments. A treatment generally comprises one dose of the first cleansing solution (or components for preparing the first cleansing solution) and one dose of the second cleansing solution (or components for preparing the first cleansing solution). In a kit of the invention, preferably the first component comprises one dose of the first cleansing solution, and the second component comprises one dose of the second cleansing solution.

A kit of the invention may be for use in a method of cleansing the colon comprising:
the subject taking an effective amount of a first colon cleansing solution as described herein; and then
the subject taking an effective amount of a second colon cleansing solution as described herein.

9. ALTERNATIVE COLON CLEANSING REGIMENS a) General

The solutions and compositions of the first and second aspects of the invention described above in sections 2 to 5 find further use in split dose colon cleansing treatments in which the subject takes two different solutions (a first colon cleansing solution, followed by a second colon cleansing solution) in which the solution of the first or second aspect of the invention is the first colon cleansing solution. In a fifth aspect, the invention thus provides a method of cleansing the colon of a mammal comprising:
the subject taking an effective amount of a first colon cleansing solution; and then
the subject taking an effective amount of a second colon cleansing solution,
the first colon cleansing solution being a solution of the first or second aspect of the invention described above in sections 2 to 5.

The invention also provides a method of cleansing the colon of a mammal comprising:
the subject taking an effective amount of a first colon cleansing solution; and then
the subject taking an effective amount of a second colon cleansing solution,
the first colon cleansing solution being a solution comprising
a) 300 to 800 mmol per litre ascorbate anion provided by a mixture of:
(i) ascorbic acid and
(ii) one or more salts of ascorbic acid
the components (i) and (ii) being present in a molar ratio of from 1:4.5 to 1:7.0; and
b) optionally 10 to 200 g per litre polyethylene glycol.

The invention also provides a method of cleansing the colon of a mammal comprising:
the subject taking an effective amount of a first colon cleansing solution; and then
the subject taking an effective amount of a second colon cleansing solution,
the first colon cleansing solution being a solution comprising
a) 360 to 440 mmol per litre ascorbate anion provided by one or more salts of ascorbic acid; and
b) optionally 10 to 200 g per litre polyethylene glycol;
the solution being essentially free from ascorbic acid.

The solutions and methods of the fifth aspect of the invention may have the features described above in relation to the solutions and methods of the third aspect of the invention as set out in section 6 above.

b) Alternative:

The invention also provides a method of cleansing the colon of a subject comprising:
administering to the subject an effective amount of a first cleansing solution; and then after a time interval
administering to the subject an effective amount of a second cleansing solution,
wherein the first cleansing solution is hyper-osmotic and contains ascorbic acid, one or more salts of ascorbic acid, or a mixture thereof (for example ascorbic acid and sodium ascorbate, for example sodium ascorbate); and wherein the second cleansing solution is either substantially free from ascorbic acid and salts thereof, or contains ascorbic acid, one or more salts of ascorbic acid, or a mixture thereof, in an amount providing a lower concentration of ascorbate anion than is present in the first cleansing solution. The first cleansing solution may comprise PEG and electrolytes (for example sodium chloride and potassium chloride). The second solution may comprise PEG; it may comprise an alkali metal or alkaline earth metal sulphate (for example sodium sulphate); it may comprise electrolytes (for example sodium chloride and potassium chloride). There are also provided kits comprising a first and a second solution according to the invention, and kits comprising compositions for preparing the first and second solutions.

The first cleansing solution contains a higher concentration of ascorbate anion than is present in the second cleansing solution. For example, the first cleansing solution contains twice the concentration of the ascorbate anion than the second cleansing solution or more. For example, the first solution contains three times or more, four times or more, or five times or more the concentration of the ascorbate anion than the second cleansing solution. For example, the first cleansing solution contains a concentration of the ascorbate anion that is at least 50 mmol per litre greater than that of the second cleansing solution. That is to say that the first solution contains a concentration of ascorbate anion that is at least 50 mmol per litre greater than that of the second solution. For example, the first solution contains a concentration of the ascorbate anion that is greater by at least 100 mmol per litre, for example at least 200 mmol per litre, at least 300 mmol per litre.

For example, the second cleansing solution may be substantially free from an ascorbate component.

For example, the first cleansing solution may comprise:
56.6 g sodium ascorbate, or
33.9 g sodium ascorbate and 20.1 g ascorbic acid, or
33.9 g sodium ascorbate, or
33.9 g sodium ascorbate and 21.4 g magnesium ascorbate.

The first cleansing solution may further comprise polyethylene glycol. The polyethylene glycol (PEG) may, for example, have an average molecular weight of 2500 to 4500 Da, for example 3000 to 4000 Da. For example, the PEG may be PEG 3350 or PEG 4000 as defined in national pharmacopeias. Further examples of suitable PEGs recognized in some national pharmacopeias include Macrogols, for example Macrogol 4000.

For example, the first cleansing solution may comprise 20 g or 40 g PEG 3350. For example, the first cleansing solution may have a volume of 500 ml. For example it may have a volume of 16 or 17 US fluid ounces.

The second cleansing solution may comprise polyethylene glycol and/or an alkali metal sulphate, an alkaline earth metal sulphate, or a mixture thereof.

The polyethylene glycol (PEG) in the second cleansing solution may be as described immediately above for the first cleansing solution. The PEG in the second cleansing solution can be a different PEG from the PEG in the second cleansing solution. For example, one PEG may be PEG3350 and the other PEG may be PEG4000. For example, the second cleansing solution may comprise 100 g PEG 3350. For example, the second cleansing solution may have a volume of 750 ml. For example it may have a volume of 25 or 26 US fluid ounces.

The second cleansing solution preferably comprises an alkali metal sulphate, an alkaline earth metal sulphate or a mixture thereof. An alkali metal or alkaline earth metal sulphate may, for example, be selected from sodium sulphate, potassium sulphate and magnesium sulphate. The solution may comprise more than one of sodium sulphate, potassium sulphate and magnesium sulphate, for example all three. Preferably, the alkali metal sulphate, an alkaline earth metal sulphate or the mixture thereof is or includes sodium sulphate. Preferably, an alkali metal sulphate or alkaline earth metal sulphate (for example sodium sulphate) is anhydrous.

For example, the second cleansing solution may have a volume of 750 ml and comprise 3 g, 6 g or 9 g of sodium sulphate.

The first and/or second cleansing solution(s) may further comprise one or more of:
a) one or more electrolytes;
b) one or more flavouring agents;
c) one or more sweeteners.

Electrolytes include salts of sodium, potassium, calcium and magnesium, particularly sodium and potassium; and salts of chloride, iodide, bicarbonate and carbonate, particularly chloride. Preferred electrolytes are sodium chloride and potassium chloride. In an embodiment, the first and/or second solution is substantially free from sodium bicarbonate.

For example, the second cleansing solution may have a volume of 750 ml and comprise 1.4 g sodium chloride and 0.3 g potassium chloride; or 1.6 g sodium chloride and 0.7 g potassium chloride; or 2.0 g sodium chloride and 1.0 g potassium chloride.

For example, the first cleansing solution may have a volume of 500 ml and comprise 3.5 g sodium chloride and 2.2 g potassium chloride; or 2.7 g sodium chloride and 1.3 g potassium chloride; or 2.8 g sodium chloride and 1.3 g potassium chloride; or 2.8 g sodium chloride and 2.0 g potassium chloride; or 3.1 g sodium chloride and 1.3 g potassium chloride. For example the first cleansing solution is substantially free from sodium bicarbonate.

The first and/or second cleansing solution(s) preferably include a flavouring agent. Flavouring for use in compositions of the invention should preferably mask saltiness, be relatively sweet but not excessively so, and be stable in the composition. Flavouring makes the solutions more palatable and thus aids patient compliance. Preferred flavourings include lemon e.g. Ungerer Lemon (available from Ungerer Limited, Sealand Road, Chester, England CH1 4LP) strawberry e.g. Ungerer Strawberry, grapefruit e.g. Ungerer Grapefruit flavouring powder, blackcurrant e.g. Ungerer Blackcurrant, pineapple e.g. IFF (International Flavours and Fragrances) Pineapple flavouring powder, orange eg Firmenich Orange, vanilla/lemon and lime e.g. IFF Vanilla and Givaudin Roure Lemon and Lime Flav-o-lok, fruit punch eg Ungerer fruit punch, citrus punch, mango, and berry. Those and further suitable flavourings are available from International Flavours and Fragrances Inc. (Duddery Hill, Haverhill, Suffolk, CB9 8LG, England), Ungerer & Company (Sealand Road, Chester, England CH1 4LP) or Firmenich (Firmenich UK Ltd., Hayes Road, Southall, Middlesex UB2 5NN). More preferred flavourings are lemon, kiwi, strawberry, grapefruit, orange, fruit punch and mango.

Fruit punch and mango are especially preferred flavourings for the first solution. The most preferred flavourings for the second solution are lemon flavour and orange flavour.

The first and/or second cleansing solution(s) preferably include a sweetener. Sugar-based sweeteners are generally not suited for colon cleansing compositions because the delivery of unabsorbed sugars to the colon provides a substrate for bacteria. Such sugars may be metabolised by the bacteria to form explosive gases such as hydrogen and methane. The presence of explosive gases in the colon can be highly dangerous when electrical apparatus is to be used during colonoscopy or other procedures. Preferred sweeteners include aspartame, acesulfame potassium (acesulfame K), sucralose and saccharine, and/or combinations thereof. For example, compositions of the invention may comprise one or both of aspartame and acesulfame potassium (acesulfame K). For example, compositions of the invention may comprise one or both of sucralose and acesulfame potassium (acesulfame K). Alternatively, compositions of the invention can be substantially free from added sweeteners, for example to minimize the number of different components in the compositions. Citric acid may also be present as a taste enhancer.

EXAMPLES

General Description of Sample Evaluation Protocol

The same sample evaluation protocol was used for the taste tests of all of the solutions described below that were taste tested. The protocol was as follows:
1. The solution was sipped from 1 oz cups, swished in the mouth, and expectorated.

2. Initial flavour was immediately evaluated (t=0).
3. The aftertaste was evaluated at periodic time intervals: 1, 3 and 5 minutes.
4. Upon completing the evaluation, the panellists cleansed their palates using spring water and unsalted crackers.

The Panelists were asked to provide a score of their perception of the intensity of the saltiness of the solutions, using the scale:

Intensity Scale: 0=None
1=Slight
2=Moderate
3=Strong

In general the panel consisted of from 2 to 8 tasters. The average saltiness intensity score was plotted against time.

Example 1: Sodium Ascorbate/Ascorbic Acid Solutions

In an initial set of solutions containing PEG3350 (40 g), sodium chloride (2.8 g), potassium chloride (1.3 g) and sodium ascorbate (56.6 g), it was found that the sweeteners sucralose and aspartame were most effective in reducing the perceived saltiness of the solution. Acesulfame-K and sodium saccharin were less effective.

Figure 2:
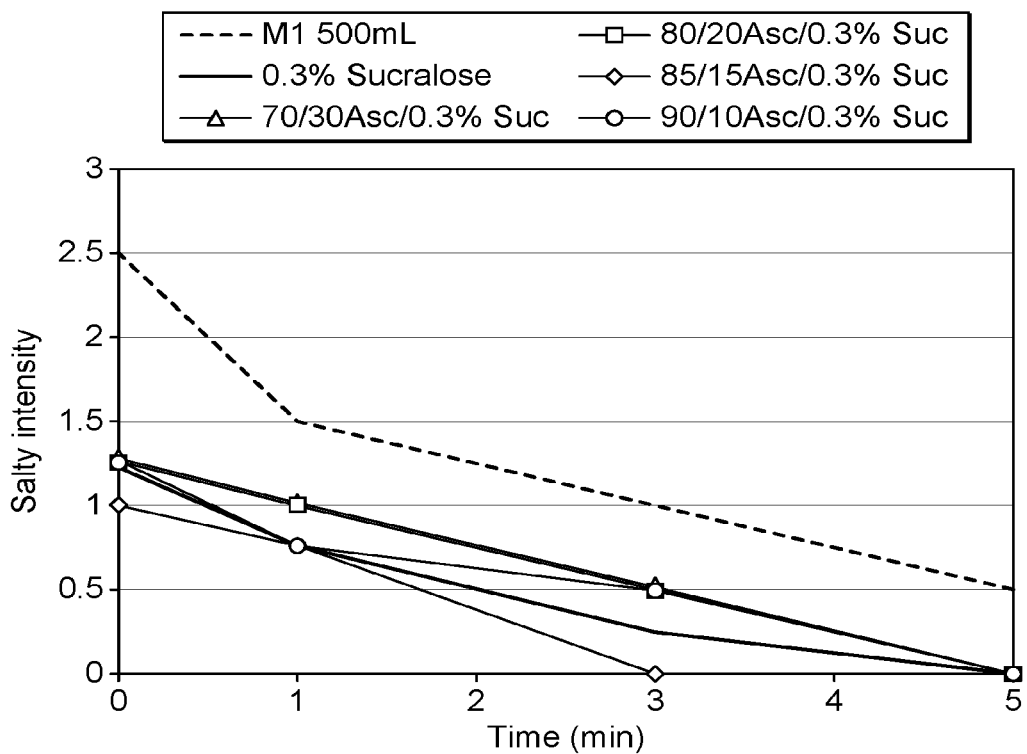
FIG. 2 is a graph showing the results of the taste testing of the solutions set forth in Table 2 herein.

The solutions in Tables 1 and 2 were prepared and taste tested. The results of the taste testing are shown in FIGS. 1 and 2.

TABLE 1

| | | | | Aspartame-containing solutions | | | |
|---|---|---|---|---|---|---|---|
| Sol'n | PEG3350/g | NaCl/g | KCl/g | Aspartame/g | Sodium Ascorbate/g | Ascorbic Acid/g | Molar ratio | Water to Vol/ml |
| F1 | 40 | 2.8 | 1.3 | 0 | 56.60 | 0 | 100:0 | 500 |
| F2 | 40 | 2.8 | 1.3 | 2.0 | 56.60 | 0 | 100:0 | 500 |
| F3 | 40 | 2.8 | 1.3 | 2.0 | 39.62 | 15.10 | 70:30 | 500 |
| F4 | 40 | 2.8 | 1.3 | 2.0 | 45.28 | 10.06 | 80:20 | 500 |
| F5 | 40 | 2.8 | 1.3 | 2.0 | 48.11 | 7.55 | 85:15 | 500 |
| F6 | 40 | 2.8 | 1.3 | 2.0 | 50.94 | 5.03 | 90:10 | 500 |

TABLE 2

| | | | | Sucralose-containing solutions | | | |
|---|---|---|---|---|---|---|---|
| Sol'n | PEG3350/g | NaCl/g | KCl/g | Sucralose/g | Sodium Ascorbate/g | Ascorbic Acid/g | Molar ratio | Water to Vol/ml |
| G1 | 40 | 2.8 | 1.3 | 0 | 56.60 | 0 | 100:0 | 500 |
| G2 | 40 | 2.8 | 1.3 | 1.5 | 56.60 | 0 | 100:0 | 500 |
| G3 | 40 | 2.8 | 1.3 | 1.5 | 39.62 | 15.10 | 70:30 | 500 |
| G4 | 40 | 2.8 | 1.3 | 1.5 | 45.28 | 10.06 | 80:20 | 500 |
| G5 | 40 | 2.8 | 1.3 | 1.5 | 48.11 | 7.55 | 85:15 | 500 |
| G6 | 40 | 2.8 | 1.3 | 1.5 | 50.94 | 5.03 | 90:10 | 500 |

In FIGS. 1 and 2, it is seen that the saltiness intensity is reduced most in the solution containing sodium ascorbate and ascorbic acid in the ratio 85:15, i.e. solutions F5 and G5.

Example 2: Sodium Ascorbate Solutions and Taste Testing

The solutions in Table 3 were prepared and taste tested. The results of the taste testing are shown in FIG. 3.

TABLE 3

| | | | | Sodium ascorbate solutions | | |
|---|---|---|---|---|---|---|
| Sol'n | PEG3350/g | NaCl/g | KCl/g | Aspartame/g | Sodium Ascorbate/g | Water to Vol/ml |
| H1 | 40 | 2.8 | 1.3 | 0 | 56.6 | 500 |
| H2 | 40 | 2.8 | 1.3 | 0 | 40 | 500 |
| H3 | 40 | 2.8 | 1.3 | 1.00 | 40 | 500 |
| H4 | 40 | 2.8 | 1.3 | 1.25 | 40 | 500 |
| H5 | 40 | 2.8 | 1.3 | 1.50 | 40 | 500 |

Figure 3:
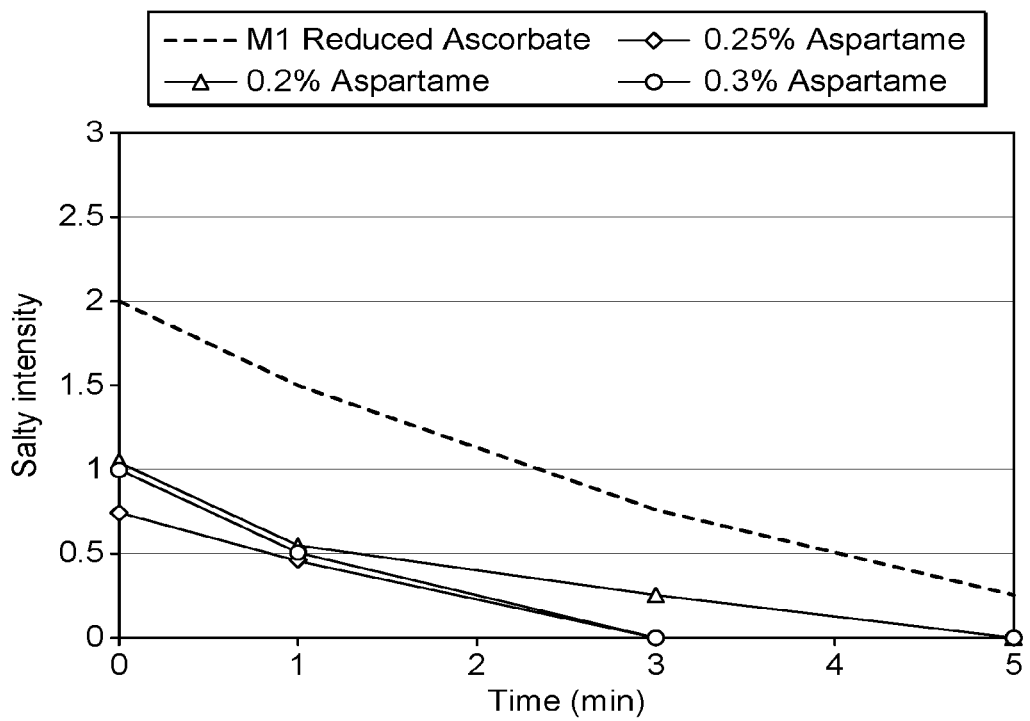
FIG. 3 is a graph showing the results of the taste testing of the solutions set forth in Table 3 herein.

In FIG. 3, it is seen that the saltiness intensity is reduced by decreasing the amount of sodium ascorbate in the solution (compare H1 vs H2). It is further seen that the saltiness is reduced most by 1.25 g/500 ml of aspartame.

Example 3: PEG-Electrolyte Solutions and Taste Testing

In an initial set of solutions containing PEG3350 (100 g), sodium sulphate (9.0 g), sodium chloride (1.4 g), potassium chloride (0.3 g), it was found that the sweeteners sucralose (0.1%), aspartame (0.4%) or a mixture of the two (sucralose 0.07%/aspartame 0.12%) were most effective in reducing the perceived saltiness of the solution. Acesulfame-K, sodium saccharin and other mixtures were less effective.

Figure 4:
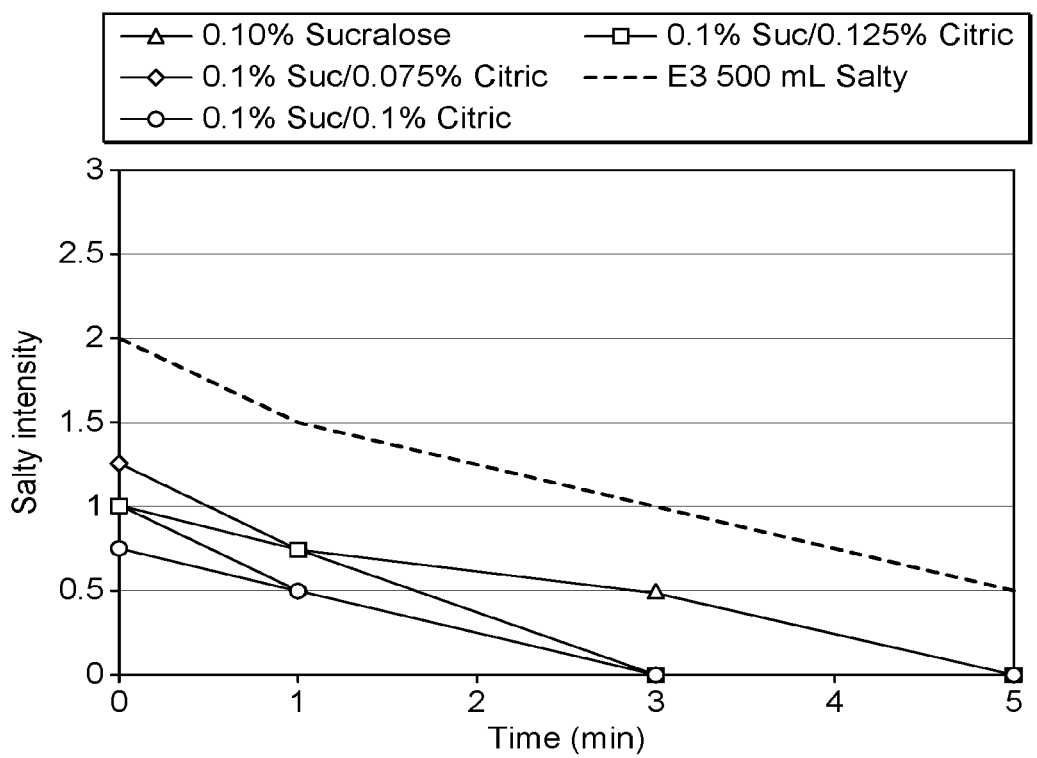
FIG. 4 is a graph showing the results of the taste testing of the solutions set forth in Table 4 herein.

The solutions in Table 4 were prepared and taste tested. The results of the taste testing are shown in FIG. 4.

TABLE 4

| | | | | PEG-electrolyte solutions | | |
|---|---|---|---|---|---|---|
| Sol'n | PEG3350/g | Na$_2$SO$_4$/g | NaCl/g | KCl/g | Sucralose/g | Citric Acid/g | Water to Vol/ml |
| I1 | 100.0 | 9.0 | 1.4 | 0.3 | 0 | 0 | 500 |
| I2 | 100.0 | 9.0 | 1.4 | 0.3 | 0.50 | 0 | 500 |
| I3 | 100.0 | 9.0 | 1.4 | 0.3 | 0.50 | 0.375 | 500 |

TABLE 4-continued

PEG-electrolyte solutions

| Sol'n | PEG3350/g | Na₂SO₄/g | NaCl/g | KCl/g | Sucralose/g | Citric Acid/g | Water to Vol/ml |
|---|---|---|---|---|---|---|---|
| I4 | 100.0 | 9.0 | 1.4 | 0.3 | 0.50 | 0.50 | 500 |
| I5 | 100.0 | 9.0 | 1.4 | 0.3 | 0.50 | 0.625 | 500 |

The results of the taste testing are shown in FIG. 4. It is seen that the solutions containing citric acid were perceived as less salty than the solutions without citric acid.

Example 4: Bowel Cleansing Solutions

The following bowel cleansing solutions of the invention were prepared. For solution S1, the components shown in Table 5 were combined in dry powder form and sealed in respective sachets A and B as indicated in the table. The solution was then prepared by dissolving the contents in water to the volume stated in the penultimate column. Solution S2 was prepared in an analogous manner.

TABLE 5

| | Sachet A | | | | | Sachet B | | |
|---|---|---|---|---|---|---|---|---|
| Sol'n | PEG3350/g | Na₂SO₄ (anhyd)/g | NaCl/g | KCl/g | Sucralose/g | Fruit Punch Flavouring/g | Citric Acid/g | Water to Vol/ml | V(350)/ml |
| S1 | 100.00 | 9.00 | 2.00 | 1.00 | 0.476 | 0.469 | 0.792 | 750 | 1180 |
| S2 | 100.00 | 9.00 | 2.00 | 1.00 | 0.40 | 0.500 | 0.75 | 500 | 1210 |

For solution T1, the components shown in Table 6 were combined in dry powder form and sealed in respective sachets C and D as indicated in the table. The solution was then prepared by mixing the contents of the two sachets together and then dissolving them in water to the volume stated in the penultimate column Solution T2 was prepared in an analogous manner

TABLE 6

| | Sachet C | | | | | Sachet D | | | |
|---|---|---|---|---|---|---|---|---|---|
| Sol'n | PEG3350/g | NaCl/g | KCl/g | Aspartame/g | Orange Flavour/g | Sodium Ascorbate/g | Ascorbic Acid/g | Water to Vol/ml | V(350)/ml |
| T1 | 40.00 | 3.20 | 1.20 | 1.93 | 0.60 | 48.11 | 7.54 | 500 | 1850 |
| T2 | 40.00 | 2.50 | 0.90 | 1.10 | 0.80 | 40.00 | 0 | 500 | 1500 |

Example 4a—V(350) Osmolality Measurements

In order to assess the osmotic strength of the solutions, it was determined how much water was required to provide a solution with measured osmolality of 350 mOsmol/kg from the amounts of the components in Tables 5 and 6.

To each solution prepared by dissolving the components in Tables 5 and 6 above in 500 ml of deionised water was added further deionised water until it reached an osmolality of 350 mOsmol/kg. The total volumes (including the initial 500 ml) required to reach an osmolality of 350 mOsmol/kg are recorded in Tables 5 and 6 in the final columns. Osmolalities were measured using an Advanced Instruments, Inc Model 3250 osmometer. The osmometer was operated following standard instructions: after the device passes a calibration check, the "Low Range" osmolality range (0 to 2000 mOsmol/kg) is selected, and a sample tube containing 2500 of sample solution is placed in the freezing chamber. The "start" button is then pressed. When the measurement is completed, the device displays the measurement result and that is recorded.

Example 4b—Bowel Cleansing

In a bowel cleansing study, subjects are given solutions S1 or S2 in an evening followed by T1 or T2 the following morning. In a variant, subjects are given solution T1 or T2 in an evening followed by S1 or S2 the following morning.

Each subject receives the solution regimen in the split dose intake:
Evening dose: Day 1; start intake between 17:00 and 18:00 for an intake period of up to 2 hours after fasting from 14:00 hours.
Morning dose: Day 2; start intake between 07:00 and 08:00 for an intake period of 2 hours.

Following each dose additional clear liquid will be consumed to make the total dose and additional clear fluid ingested equal to at least 3 L in the case of Arms 1 to 6, 8 and 9, and at least 2 L in the case of Arm 7.

Each dose of cleansing solution is reconstituted with water from the appropriate pair of sachets containing powder for oral solution. The cleansing solution can be cooled in the fridge based on subject preference. Evening cleansing solution dose is drunk within 2 hours after the start of the intake on the evening of Day 1. At least the indicated additional clear fluid is also consumed, preferably within 1 hour after the end of intake of cleansing solution in the evening.

In the morning of Day 2, the second dose is drunk within 2 hours after the start of intake. At least the indicated additional clear fluid is also consumed, preferably within 1 hour after the end of intake of cleansing solution in the morning. The total duration of each intake of cleansing solution and clear fluid intake should normally not exceed 3 hours. Each subject is instructed to drink the assigned cleansing solutions as 100 mL fractions every 10 minutes. The mandatory additional clear liquid intake (water) after the cleansing solution intake can be taken by the subject as prefers, usually within 1 hour after completion of each cleansing solution intake. The start time and finish time of intake is recorded. The volume of any cleansing solution or additional clear fluid left in the respective containers is measured. In arms 6 to 9 the volume of fluid consumed ad libitum is monitored and recorded.

TABLE 7

| Arm | Arm 1 | Arm 2 | Arm 3 | Arm 4 | Arm 5 |
|---|---|---|---|---|---|
| Evening | S1 (750 ml) 875 ml additional clear fluid | T1 (500 ml) 875 ml additional clear fluid | S2 (500 ml) 1000 ml additional clear fluid | MOVIPREP (1000 ml) 500 ml additional clear fluid | T1 (500 ml) 1000 ml additional clear fluid |
| Morning | T1 (500 ml) 875 ml | S1 (750 ml) 875 ml | T1 (500 ml) 1000 ml | MOVIPREP (1000 ml) 500 ml | S2 (500 ml) 1000 ml |

TABLE 7-continued

| Arm | Arm 1 | Arm 2 | Arm 3 | Arm 4 | Arm 5 |
|---|---|---|---|---|---|
|  | additional clear fluid | additional clear fluid | additional clear fluid | additional clear fluid | additional clear fluid |

TABLE 8

| Arm | Arm 6 | Arm 7 | Arm 8 | Arm 9 |
|---|---|---|---|---|
| Evening | S2 (500 ml) Additional clear fluid: minimum 1000 ml or more ad lib. | S2 (500 ml) Additional clear fluid: minimum 500 ml, or more ad lib | S2 (500 ml) Additional clear fluid: minimum 1000 ml or more ad lib | MOVIPREP (1000 ml) additional clear fluid minimum 500 ml or more ad lib |
| Morning | T1 (500 ml) Additional clear fluid: minimum 1000 ml or more ad lib | T1 (500 ml) Additional clear fluid: minimum 500 ml, or more ad lib | T2 (500 ml) Additional clear fluid: minimum 1000 ml or more ad lib | MOVIPREP (1000 ml) additional clear fluid: minimum 500 ml or more ad lib |

Stool output is measured from the start of the intake on the evening of Day 1 and over the following 24 hours. "Stool" is the term used to refer to all bowel effluent. Mostly, it is liquid. The following are also assessed Tolerability (vomiting rate).

Time and volume of cleansing solution to reach a clear effluent.

In certain subjects, the following are also assessed:

Colon cleansing success.

The segmental cleansing scores for each of the five colon segments.

Pharmacokinetic evaluation of key active ingredients: Ascorbate components and their metabolite (oxalic acid) in blood, urine and faeces and PEG3350 and electrolytes in faeces at defined time points, to demonstrate biological activities. Electrolytes in blood and urine are quantified using standard clinical chemistry methods.

The study described above was carried out in two parts: Parts A and B.

Part A: In the part A, 120 subjects (70 male, 50 female) were allocated to the four study Arms, Arms 1 to 4. They were given the solutions as set out in Table 7. At the time of filing, the full statistical analysis of the results is not complete. The interim results based on a preliminary analysis of the data and available at the time of filing are shown in Table 9.

TABLE 9

| Arm | Arm 1 | Arm 2 | Arm 3 | Arm 4 |
|---|---|---|---|---|
| Number of subjects | 30 | 30/29* | 30 | 30/29* |
| Mean Stool Weight (g) | 2951 g | 3219 g | 3399 g | 2491 g |
| Stool Weight 90% confidence interval (g) | 2680 g-3222 g | 2963 g-3475 g | 3221 g-3578 g | 2213 g-2769 g |
| Protocol total IMP volume | 1250 ml | 1250 ml | 1000 ml | 2000 ml |
| Protocol total additional clear fluid volume | 1750 ml | 1750 ml | 2000 ml | 1000 ml |
| Vomiting rate | 1 (3.33%) | 3 (10%) | 1 (3.33%) | 1 (3.33%) |

Overall, the compliance level was good. However, in each of Arms 2 and 4, 30 subjects began the study, but one subject left the study after consuming the first solution, and before any stool sample could be collected (thus 29 subjects are indicated (*)). The stool weight data are based on the set of 30 subjects for Arms 1 and 3, and on the set of 29 subjects for Arms 2 and 4. Both of those subjects who left the study had the symptom of vomiting. They are included in the vomiting rate results.

It is seen that in each of Arms 1, 2 and 3 the subjects achieved a higher mean stool output weight than in Arm 4, which represents a prior art colon cleansing solution. This was achieved with the subjects in each of Arms 1, 2 and 3 consuming a lower total volume of bowel cleansing solution (investigational medicinal product "IMP") than in Arm 4. The vomiting rate for Arm 2 was higher than for the other arms. The vomiting rate for each of the solutions was within expected limits for a bowel cleansing solution.

Part B: In part B, 120 subjects (54 male, 66 female) were allocated to the four study Arms, Arms 6 to 9. They were given the solutions as set out in Table 8. Mean stool output was highest in Arm 7 and slightly lower in Arm 6. Arm 8 gave a lower mean stool output, but all of Arms 6, 7 and 8 gave a higher mean stool output than Arm 9, which represents a prior art colon cleansing solution. Mean stool output exceeded 2400 g in all arms. Mean stool output in Arms 6 and 7 exceeded 3000 g.

The subjects in part B underwent colonoscopy and the quality of cleansing was graded by the colonoscopist, who was not aware of which cleansing treatment had been administered. Grading used the Harefield Cleansing Scale. For details of the Harefield Cleansing Scale, see Halphen et al., *Gastrointestinal Endoscopy,* 2013, 78, 121-131. The Harefield Cleansing Scale grades colon cleansing as Grade A, B, C or D, A being the best. Grades A and B are considered a successful cleansing; Grades C and D are considered an unsuccessful cleansing. At the time of filing, the full statistical analysis of the results is not complete. The interim results based on a preliminary analysis of the data and available at the time of filing are shown in Table 10.

TABLE 10

| Arm | Arm 6 | Arm 7 | Arm 8 | Arm 9 |
|---|---|---|---|---|
| Number of subjects | 30 | 30 | 30 | 30 |
| Protocol total IMP volume | 1000 ml | 1000 ml | 1000 ml | 2000 ml |
| Protocol minimum total additional clear fluid volume | 2000 ml | 1000 ml | 2000 ml | 1000 ml |
| Grade A | 22 | 28 | 20 | 6 |
| Grade B | 8 | 2 | 7 | 21 |
| Grade C | 0 | 0 | 3 | 2 |
| Grade D | 0 | 0 | 0 | 1 |

It is seen in Table 10 that there was a higher proportion of Grade A cleansing in each of Arms 6, 7 and 8 than in Arm 9. This was achieved with the subjects in each of Arms 6, 7 and 8 consuming a lower total volume of bowel cleansing solution (investigational medicinal product "IMP") than in Arm 9.

Example 5: Bowel Cleansing Solutions

The following bowel cleansing solutions of the invention are prepared. For solution S3, the components shown in Table 11 are combined in dry powder form and sealed in respective sachets A and B as indicated in the table. The solution is then prepared by dissolving the contents in water to the volume stated in the far right-hand column. Solution S4 is prepared in an analogous manner

TABLE 11

| | Sachet A | | | | | | Sachet B | |
|---|---|---|---|---|---|---|---|---|
| Sol'n | PEG3350/g | $Na_2SO_4$ (anhyd)/g | NaCl/g | KCl/g | Sucralose/g | Mango Flavouring/g | Fruit Punch Flavouring/g | Citric Acid #/g | Water to Vol/ml |
| S3 | 100.00 | 9.00 | 2.00 | 1.00 | 0.79 | 1.43 | — | 1.74 | 500 |
| S4 | 100.00 | 9.00 | 2.00 | 1.00 | 0.79 | — | 1.59 | 1.74 | 500 | citric acid encapsulated with water souble coating

For solution T3, the components shown in Table 12 are combined in dry powder form and sealed in respective sachets C and D as indicated in the table. The solution is then prepared by mixing the contents of the two sachets together and then dissolving them in water to the volume stated in the far right-hand column Solutions T4, T5 and T6 are prepared in an analogous manner

TABLE 12

| | Sachet C | | | | | Orange | Sachet D | | |
|---|---|---|---|---|---|---|---|---|---|
| Sol'n | PEG3350/g | NaCl/g | KCl/g | Aspartame/g | Citrus flavour/g | GR'fruit Flavour | Sodium Ascorbate/g | Ascorbic Acid/g | Water to Vol/ml |
| T3 | 40.00 | 3.20 | 1.20 | 0.875 | 1.6 | — | 48.11 | 7.54 | 500 |
| T4 | 40.00 | 3.20 | 1.20 | 0.875 | — | 2.1 | 48.11 | 7.54 | 500 |

TABLE 13

| | Sachet C | | | | | | Sachet D | | |
|---|---|---|---|---|---|---|---|---|---|
| Sol'n | PEG3350/g | NaCl/g | KCl/g | Aspartame/g | Lemon/Lime Flavour/g | orange flavour | Sodium Ascorbate/g | Ascorbic Acid/g | Water to Vol/ml |
| T5 | 40.00 | 2.50 | 0.90 | 1.625 | 1.6 | — | 40.00 | — | 500 |
| T6 | 40.00 | 2.50 | 0.90 | 1.625 | — | 2.15 | 40.00 | — | 500 |

We claim:

1. A colon cleansing solution comprising:
   (i) 175 to 220 g per litre PEG having an average molecular weight of 2500 to 4500 Da;
   (ii) 15 to 20 g per litre of one or more alkali metal sulphates, alkaline earth metal sulphates or a mixture thereof;
   (iii) 3.0 to 5.0 g per litre sodium chloride, and 1.5 to 2.5 g per litre potassium chloride;
   (iv) optionally one or more flavouring agents; and
   (v) optionally one or more sweeteners,
   wherein the solution has a volume of 400-600 ml.

2. The colon cleansing solution as claimed in claim 1, wherein the solution is substantially free of an ascorbate component.

3. The solution as claimed in claim 1, wherein the alkali metal sulphates, alkaline earth metal sulphates or a mixture thereof are selected from sodium sulphate, potassium sulphate and magnesium sulphate.

4. The colon cleansing solution as claimed in claim 1, comprising a sweetener and further comprising a souring agent.

5. The colon cleansing solution as claimed in claim 4, wherein the souring agent is citric acid or encapsulated citric acid.

6. The colon cleansing solution as claimed in claim 1, wherein the sweetener is sucralose.

7. The colon cleansing solution as claimed in claim 1, wherein the solution comprises 200 g per litre PEG.

8. The colon cleansing solution as claimed in claim 1, wherein the solution comprises 17 to 19 g per litre of one or more alkali metal sulphates, alkaline earth metal sulphates or a mixture thereof.

9. The colon cleansing solution as claimed in claim 1 comprising:
   (i) 200 g per litre PEG having an average molecular weight of 2500 to 4500 Da;
   (ii) 18 g per litre of sodium sulphate;
   (iii) 4.0 g per litre sodium chloride, and 2.0 g per litre potassium chloride;
   (iv) optionally one or more flavouring agents; and
   (v) optionally one or more sweeteners;
   wherein the solution is substantially free of an ascorbate component.

10. A kit comprising:
    a first colon cleansing solution, and
    a second colon cleansing solution,
    wherein the first colon cleansing solution is as claimed in claim 2.

11. The kit as claimed in claim 10, wherein the second colon cleansing solution comprises:
    a) 300 to 800 mmol per litre ascorbate anion provided by a mixture of:
       (i) ascorbic acid and
       (ii) one or more salts of ascorbic acid,
       the components (i) and (ii) being present in a molar ratio of from 1:4.5 to 1:7.0;
    b) 10 to 200 g per litre polyethylene glycol;
    c) optionally one or more electrolytes;
    d) optionally one or more alkali metal or alkaline earth metal sulphates;
    e) optionally one or more flavouring agents; and
    f) optionally one or more sweeteners.

12. The kit as claimed in claim 10, wherein the second cleansing solution comprises one or more of the following:
    (a) the one or more salts of ascorbic acid are selected from sodium ascorbate, potassium ascorbate, magnesium ascorbate and calcium ascorbate, or a mixture thereof;
    (b) the ascorbate anion in a concentration of 300-700 mmol per litre;
    (c) the molar ratio of the components (i) and (ii) is from 1:4.75 to 1:6.75;
    (d) the solution comprises 60 to 140 g/litre of ascorbate component, and/or
    (e) 12 to 20 g/litre of ascorbic acid and 80 to 120 g/litre of sodium ascorbate.

13. The kit as claimed in claim 10, wherein the second cleansing solution comprises one or more of the following:
    (a) essentially free from alkali metal sulphates and alkaline earth metal sulphates;
    (b) a flavouring agent;
    (c) a sweetener;
    (d) aspartame and orange flavouring; and/or
    (e) aspartame at 0.5 to 4 g per litre and orange flavouring at 0.2 to 1.8 g per litre.

14. A kit comprising compositions used for admixture with water, wherein the compositions are used to make the first solution as claimed in claim 1 and second solution as claimed in claim 11.

15. The kit as claimed in claim 14, wherein the composition used to make the first solution comprises:
    (i) 100 g PEG having an average molecular weight of 3000 to 4000 Da.;
    (ii) 9.0 g sodium sulphate;
    (iii) 2.0 g sodium chloride and 1.0 g potassium chloride;
    (iv) optionally one or more flavouring agents; and
    (v) optionally one or more sweeteners;
    wherein the composition is substantially free of an ascorbate component.

16. The kit as claimed in claim 14, wherein the composition used to make the second solution comprises:
    a)
       (i) 7.54 g ascorbic acid and
       (ii) 48.11 g sodium ascorbate;
    b) 40 g PEG having an average molecular weight of 3000 to 4000 Da;
    c) 3.20 g sodium chloride and 1.20 g potassium chloride;
    d) one or more flavouring agents; and
    e) one or more sweeteners.

17. The kit as claimed in claim 14, wherein the composition used to make the first solution comprises:
    (i) 100 g PEG having an average molecular weight of 3000 to 4000 Da.;
    (ii) 9.0 g sodium sulphate;
    (iii) 2.0 g sodium chloride and 1.0 g potassium chloride;
    (iv) optionally one or more flavouring agents; and
    (v) optionally one or more sweeteners;
    wherein the composition is substantially free of an ascorbate component; and
    the composition used to make the second composition comprises:
    a)
       (i) 7.54 g ascorbic acid and
       (ii) 48.11 g sodium ascorbate;
    b) 40 g PEG having an average molecular weight of 3000 to 4000 Da;
    c) 3.20 g sodium chloride and 1.20 g potassium chloride;
    d) one or more flavouring agents; and
    e) one or more sweeteners.

18. The kit as claimed in claim 17, wherein each composition is provided to be made up in 400-600 ml water.

19. A method of cleansing the colon of a subject comprising administering to the subject an effective amount of a colon cleansing solution as claimed in claim 1.

20. A method of cleansing the colon of a subject comprising administering to the subject an effective amount of a colon cleansing solution as claimed in claim 9.

* * * * *